US007235372B2

(12) United States Patent
Korneluk et al.

(10) Patent No.: US 7,235,372 B2
(45) Date of Patent: Jun. 26, 2007

(54) USE OF NEURONAL APOPTOSIS INHIBITOR PROTEIN (NAIP)

(75) Inventors: Robert G. Korneluk, Ottawa (CA); Alexander E. MacKenzie, Ottawa (CA); Natalie Roy, LaJolla, CA (US); George Robertson, Ottawa (CA); Katsu Tamai, Ina (JP)

(73) Assignee: University of Ottawa, Ottawa, Ontario (CA)

( * ) Notice: Subject to any disclaimer, the term of this patent is extended or adjusted under 35 U.S.C. 154(b) by 0 days.

(21) Appl. No.: 11/329,884

(22) Filed: Jan. 10, 2006

(65) Prior Publication Data

US 2006/0172348 A1 Aug. 3, 2006

Related U.S. Application Data

(63) Continuation of application No. 08/913,322, filed as application No. PCT/IB97/00142 on Jan. 17, 1997, now Pat. No. 6,994,957.

(30) Foreign Application Priority Data

Jan. 19, 1996 (GB) .................................. 9601108.5

(51) Int. Cl.
*C07K 16/00* (2006.01)
*C07K 16/38* (2006.01)
*C12P 21/08* (2006.01)
*G01N 33/53* (2006.01)

(52) U.S. Cl. .................... 435/7.1; 435/7.21; 530/387.1; 530/387.3; 530/388.1; 530/388.15; 530/388.2

(58) Field of Classification Search ...................... None
See application file for complete search history.

(56) References Cited

U.S. PATENT DOCUMENTS

| 5,919,912 | A | 7/1999 | Korneluk et al. |
| 6,020,127 | A | 2/2000 | MacKenzie et al. |
| 6,107,041 | A | 8/2000 | Korneluk et al. |
| 6,156,535 | A | 12/2000 | Korneluk et al. |
| 6,541,457 | B2 | 4/2003 | Korneluk et al. |
| 6,656,704 | B1 | 12/2003 | Korneluk et al. |
| 6,689,562 | B1 | 2/2004 | Korneluk et al. |
| 6,977,158 | B1 | 12/2005 | Korneluk et al. |
| 2002/0137028 | A1 | 9/2002 | Korneluk et al. |

FOREIGN PATENT DOCUMENTS

| WO | WO 94/06814 | 3/1994 |
| WO | WO 95/19431 | 7/1995 |
| WO | WO 96/12016 | 4/1996 |
| WO | WO 97/06255 | 2/1997 |

OTHER PUBLICATIONS

Birnbaum et al., "An Apoptosis-Inhibiting Gene from a Nuclear Polyhedrosis Virus Encoding a Polypeptide with Cys/His Sequence Motifs," *J. Virol.* 68:2521-2528 (1994).

Campbell, "Monoclonal Antibody Technology," Elsevier Science Publishers B.V. N.Y. NY. (1984).

Clem and Miller, "Induction and Inhibition of Apoptosis by Insect Viruses," in "Apoptosis II: The Molecular Basis of Apoptosis in Disease," Tomei and Cope (eds.), pp. 89-110 Cold Spring Harbor Press New York, NY, p. 89 (1994).

Clem et al., "Prevention of Apoptosis by a Baculovirus Gene During Infection of Insect Cells," *Science* 254:1388-1390 (1991).

Clem and Miller, "Control of Programmed Cell Death by the Baculovirus Genes P35 and Iap," *Mol. Cell. Biol.* 14:5212-5222 (1994).

Clem et al., "Anti-Apoptotic Genes of Baculovirus," *Cell Death* 3:9 (1996).

Crook et al., "An Apoptosis-Inhibiting Baculovirus Gene with a Zinc Finger-Like Motif," *J. Virol.* 67:2168-2174 (1993).

Dhein et al., "Autocrine T-Cells Suicide Mediated by APO-1/(Fas/CD95)," *Nature* 373:438-441 (1995). [Abstract].

Duckett et al., "A Conserved Family of Cellular Genes Related to the Baculovirus Iap Gene and Encoding Apoptosis Inhibitors," *EMBO J.* 15:2685-2694 (1996).

Fernandez et al., "Differential Sensitivity of Normal and Ha-Ras-Transformed C3H Mouse Embryo Fibroblasts to Tumor Necrosis Factor: Induction of Bcl-2, C-Myc, and Manganese Superoxide Dismutase in Resistant Cells," *Oncogene* 9:2009-2017 (1994). [Abstract].

Ferrari et al., "N-Acetylcysteine (D- and L-Stereoisomers) Prevents Apoptotic Death of Neuronal Cells," *J. Neurosci.* 15:2857-2866 (1995). [Abstract].

Fisher et al., "Dominant Interfering Fas Gene Mutations Impair Apoptosis in a Human Autoimmune Lymphoproliferative Syndrome," *Cell* 81:935-946 (1995).

Gibellini et al., "Tat-Expressing Jurkat Cells Show an Increased Resistance to Different Apoptotic Stimuli, Including Acute Human Immunodeficiency Virus-Type 1 (HIV-1) Infection," *Br. J. Haematol.* 89:24-33 (1995). [Abstract].

Gilliam, "Is the Spinal Muscular Atrophy Gene Found?," *Nat. Med.* 1:124-127 (1995).

Golstein et al., "Homology Between Reaper and the Cell Death Domains of Fas and TNFR1," *Cell* 81:185-186 (1995).

Goruppi et al., "Dissection of C-Myc Domains Involved in S Phase Induction of NIH373 Fibroblasts," *Oncogene* 9:1537-1544 (1994). [Abstract].

Harrington et al., "c-Myc-Induced Apoptosis in Fibroblasts is Inherited by Specific Cytokines," *EMBO J.* 13:3286-3295 (1994). [Abstract].

Itoh and Nagata, "A Novel Protein Required fpr Apoptosis Mutational Analysis of Human Fas Antigen," *J. Biol. Chem.* 268:10932-10937 (1993). [Abstract].

(Continued)

*Primary Examiner*—Christina Chan
*Assistant Examiner*—Phuong Huynh
(74) *Attorney, Agent, or Firm*—Philip A. Swain; Gowling Lafleur Henderson LLP

(57) ABSTRACT

The invention provides a novel NAIP nucleic and sequences. Also provided are anti-NAIP antibodies and methods for modulating apoptosis and detecting compounds which modulate apoptosis.

8 Claims, 42 Drawing Sheets

OTHER PUBLICATIONS

Katsikis et al., "Fas Antigen Stimulation Induces Marked Apoptosis of T Lymphocytes in Human Immunodeficiency Virus-Infected Individuals," *J. Exp. Med.* 181:2029-2036 (1995). [Abstract].

Kerr, "Neglected Opportunities in Apoptosis Research," *Trends Cell Biol.* 5:55-57 (1995).

Korsmeyer, "Regulators of Cell Death," *Trends Genet.* 11:101-105 (1995).

Lerner, "Tapping the Immunological Repertoire to Produce Antibodies of Predetermined Specificity," *Nature* 299:592-596 (1982).

Lewin, "Genes for SMA: Multum in parvo," *Cell* 80:1-5 (1995).

Li et al., "Induction of Apoptosis in Uninfected Lymphocytes by HIV-1 Tat Protein," *Science* 268:429-431 (1995). [Abstract].

Liston et al., "Suppression of Apoptosis in Mammalian Cells by NAIP and a Related Family of IAP Genes," *Nature* 379:349-353 (1996).

Mahadevan et al., "SMA Genes: Deleted and Duplicated," *Nat. Genet.* 9:112-113 (1995).

Martin et al., "HIV-1 Infection of Human CD4+ T Cells In Vitro. Differential Induction of Apoptosis in These Cells," *J. Immunol.* 152:330-342 (1994). [Abstract].

Melino et al., "Tissue Transglutaminase and Apoptosis: Sense and Antisense Transfection Studies with Human Neuroblastoma Cells," *Mol. Cell. Biol.* 14:6584-6596 (1994). [Abstract].

Muro-Cacho et al., "Analysis of Apoptosis in Lymph Nodes of HIV-Infected Persons. Intensity of Apoptosis Correlates with the General State of Activation of the Lymphoid Tissue and not with Stage of Disease or Viral Burden," *J. Immunol.* 154:5555-5566 (1995). [Abstract].

Ngo et al., in "The Protein Folding Problem and Tertiary Structure Prediction," Merz et al., (eds.) Birkhauser Boston: Boston, MA, pp. 433 and 492-495 (1994).

Nunez and Clarke, "The Bcl-2 Family of Proteins: Regulators of Cell Death and Survival," *Trends Cell Biol.* 4:399-403 (1994).

Osborne and Schwartz, "Essential Genes that Regulate Apoptosis," *Trends Cell Biol.* 4:394-399 (1994).

Rabizadeh et al., "Expression of the Baculovirus P35 Gene Inhibits Mammalian Neural Cell Death," *J. Neurochem.* 61:2318-2321 (1993). [Abstract].

Rieux-Laucat et al., "Mutations in Fas Associated with Human Lymphoproliferative Syndrome and Autoimmunity," *Science* 268:1347-1349 (1995).

Rosenbaum et al., "Evidence for Hypoxia-Induced, Programmed Cell Death of Cultured Neurons," *Ann. Neurol.* 36:864-870 (1994). [Abstract].

Rothe et al., "The TNFR2-TRAF Signaling Complex Contains Two Novel Proteins Related to Baculoviral Inhibitor of Apoptosis Proteins," *Cell* 83:1243-1252 (1995).

Roy et al., "The Gene for Neuronal Apoptosis Inhibitory Protein is Partially Deleted in Individuals with Spinal Muscular Atrophy," *Cell* 80:167-178 (1995).

Sambrook et al., In "Molecular Cloning: A Laboratory Manual," 2nd Edn. Cold Spring Harbor Laboratory Press, Cold Spring Harbor, NY (1989).

Sato et al., "Neuronal Differentiation of PC12 Cells as A Result of Prevention of Cell Death by Bcl-2," *J. Neurobiol.* 25:1227-1234 (1994). [Abstract].

Scharf et al., "The Mouse Region Syntenic for Human Spinal Muscular Atrophy Lies Within the Lgn1 Critical Interval and Contains Multiple Copies of Naip Exon 5," *Genomics* 38:405-417 (1996).

Skolnick and Fetrow, "From Genes to Protein Structure and Function: Novel Applications of Computational Approaches in the Genomic Era," *Trends Biotechnol.* 18:34-39 (2000).

Steller, "Mechanisms and Genes of Cellular Suicide," *Science* 267:1445-1449 (1995).

Talley et al., "Tumor Necrosis Factor α-Induced Apoptosis in Human Neuronal Cells: Protection by the Antioxidant N-Acetylcysteine and the Genes Bcl-2 and CrmA," *Mol. Cell. Biol.* 15:2359-2366 (1995). [Abstract].

Terai et al., "Apoptosis as a Mechanism of Cell Death in Cultured T Lymphoblasts Acutely Infected with HIV-1," *J. Clin. Invest.* 87:1710-1715 (1991). [Abstract].

Vossbeck et al., "Direct Transforming Activity of TGF-β on Rat Fibroblasts," *Int. J. Cancer* 61:92-97 (1995). [Abstract].

Walkinshaw et al., "Induction of Apoptosis in Catecholaminergic PC12 Cells by L-DOPA. Implications for the Treatment of Parkinson's Disease," *J. Clin. Invest.* 95:2458-2464 (1995). [Abstract].

Wallace and Miyada, "Oligonucleotide Probes for the Screening of Recombinant DNA Libraries," *Methods Enzymol.* 152:432-442 (1987).

Westendorp et al., "Sensitization of T Cells to CD95-Mediated Apoptosis by HIV-1 Tat and gp120," *Nature* 375:497-500 (1995).

White et al., "Genetic Control of Programmed Cell Death in Drosophila," *Science* 264:677-683 (1994).

Williams et al., "Apoptosis: Final Control Point in Cell Biology," *Trends Cell Biol.* 2:263-267 (1992).

Wyllie, "Death Gets a Brake," *Nature* 369:272-273 (1994).

Yaraghi et al. "Cloning and Characterization of the Mouse Homologue of a Candidate Gene for Spinal Muscular Atrophy, NAIP (Neuronal Apoptosis Inhibitory Protein)," Abstract No. 875, 45th Annual Meeting of the American Society of Human Genetics, Minneapolis, Minnesota, USA, Oct. 24-28 (1995).

Yaraghi et al. "Cloning and Characterization of the Multiple Murine Homologues of NAIP (Neuronal Apoptosis Inhibitory Protein)," *Genomics* 51:107-113 (1998).

International Search Report for PCT/IB97/00142.

```
>HSU19251, 5502 bases, 79F5B1F2 checksum.        5502 nt vs.
>naip.seq, 6133 bases, FD809D8 checksum.         6133 nt
77.8% identity; Optimized score: 13374

10        20        30        40        50        60
SEQ ID. NO:1 naip-o TTCCGGCTGGACGTTGCCCTGTGTACCTCTTCGACTGCCTGTTCATCTACGACGAACCCC
                   :
SEQ ID. NO:2 naip.s T-----------------------------------------------------------

70        80        90       100       110       120
        naip-o  GGGTATTGACCCCAGACAACAATGCCACTTCATATTGCATGAAGACAAAAGGTCCTGTGC
                                                  ::::::::::::::::::::::::::
        naip.s  ------------------------------GCATGAAGACAAAAGGTCCTGTGC
                                                        10        20

130       140       150       160       170       180
        naip-o  TCACCTGGGACCCTTCTGGACGTTGCCCTGTGTTCCTCTTCGCCTGCCTGTTCATCTACG
                ::::::::::::::::::::::::::::::::::  ::::::: :::::::::::::::
        naip.s  TCACCTGGGACCCTTCTGGACGTTGCCCTGTGTACCTCTTCGACTGCCTGTTCATCTACG
                      30        40        50        60        70        80

190       200       210       220       230       240
        naip-o  ACGAACCCCGGGTATTGACCCCAGACAACAATGCCACTTCATATTGGGGACTTCGTCTGG
                ::::::::::::::::::::::::::::::::::::::::::::::::::::::::::::
        naip.s  ACGAACCCCGGGTATTGACCCCAGACAACAATGCCACTTCATATTGGGGACTTCGTCTGG
                      90       100       110       120       130       140

250       260       270       280       290       300
        naip-o  GATTCCAAGGTGCATTCATTGCAAAGTTCCTTAAATATTTTCTCACTGCTTCCTACTAAA
                ::::::::::::::::::::::::::::::::::::::::::::::::::::::::::::
        naip.s  GATTCCAAGGTGCATTCATTGCAAAGTTCCTTAAATATTTTCTCACTGCTTCCTACTAAA
                     150       160       170       180       190       200

310       320       330       340       350       360
        naip-o  GGACGGACAGAGCATTTGTTCTTCAGCCACATACTTTCCTTCCACTGGCCAGCATTCTCC
                ::::::::::::::::::::::::::::::::::::::::::::::::::::::::::::
        naip.s  GGACGGACAGAGCATTTGTTCTTCAGCCACATACTTTCCTTCCACTGGCCAGCATTCTCC
                     210       220       230       240       250       260

370       380       390       400       410       420
        naip-o  TCTATTAGACTAGAACTGTGGATAAACCTCAGAAAATGGCCACCCAGCAGAAAGCCTCTG
                ::::::::::::::::::::::::::::::::::::::::::::::::::::::::::::
        naip.s  TCTATTAGACTAGAACTGTGGATAAACCTCAGAAAATGGCCACCCAGCAGAAAGCCTCTG
                     270       280       290       300       310       320

430       440       450       460       470       480
        naip-o  ACGAGAGGATCTCCCAGTTTGATCACAATTTGCTGCCAGAGCTGTCTGCTCTTCTGGGCC
                ::::::::::::::::::::::::::::::::::::::::::::::::::::::::::::
        naip.s  ACGAGAGGATCTCCCAGTTTGATCACAATTTGCTGCCAGAGCTGTCTGCTCTTCTGGGCC
                     330       340       350       360       370       380
```

Fig. 5A

```
              490        500        510        520        530        540
naip-o TAGATGCAGTTCAGTTGGCAAAGGAACTAGAAGAAGAGGAGCAGAAGGAGCGAGCAAAAA
       :::::::::::::::::::::::::::::::::::::::::::::::::::::::::::
naip.s TAGATGCAGTTCAGTTGGCAAAGGAACTAGAAGAAGAGGAGCAGAAGGAGCGAGCAAAAA
          390        400        410        420        430        440

550        560        570        580        590        600
naip-o TGCAGAAAGGCTACAACTCTCAAATGCGCAGTGAAGCAAAAAGGTTAAAGACTTTTGTGA
       :::::::::::::::::::::::::::::::::::::::::::::::::::::::::::
naip.s TGCAGAAAGGCTACAACTCTCAAATGCGCAGTGAAGCAAAAAGGTTAAAGACTTTTGTGA
          450        460        470        480        490        500

610        620        630        640        650        660
naip-o CTTATGAGCCGTACAGCTCATGGATACCACAGGAGATGGCGGCCGCTGGGTTTTACTTCA
       :::::::::::::::::::::::::::::::::::::::::::::::::::::::::::
naip.s CTTATGAGCCGTACAGCTCATGGATACCACAGGAGATGGCGGCCGCTGGGTTTTACTTCA
          510        520        530        540        550        560

670        680        690        700        710        720
naip-o CTGGGGTAAAATCTGGGATTCAGTGCTTCTGCTGTAGCCTAATCCTCTTTGGTGCCGGCC
       :::::::::::::::::::::::::::::::::::::::::::::::::::::::::::
naip.s CTGGGGTAAAATCTGGGATTCAGTGCTTCTGCTGTAGCCTAATCCTCTTTGGTGCCGGCC
          570        580        590        600        610        620

730        740        750        760        770        780
naip-o TCACGAGACTCCCCATAGAAGACCACAAGAGGTTTCATCCAGATTGTGGGTTCCTTTTGA
       :::::::::::::::::::::::::::::::::::::::::::::::::::::::::::
naip.s TCACGAGACTCCCCATAGAAGACCACAAGAGGTTTCATCCAGATTGTGGGTTCCTTTTGA
          630        640        650        660        670        680

790        800        810        820        830        840
naip-o ACAAGGATGTTGGTAACATTGCCAAGTACGACATAAGGGTGAAGAATCTGAAGAGCAGGC
       :::::::::::::::::::::::::::::::::::::::::::::::::::::::::::
naip.s ACAAGGATGTTGGTAACATTGCCAAGTACGACATAAGGGTGAAGAATCTGAAGAGCAGGC
          690        700        710        720        730        740

850        860        870        880        890        900
naip-o TGAGAGGAGGTAAAATGAGGTACCAAGAAGAGGAGGCTAGACTTGCATCCTTCAGGAACT
       :::::::::::::::::::::::::::::::::::::::: ::::::: ::::::::::
naip.s TGAGAGGAGGTAAAATGAGGTACCAAGAAGAGGAGGCTAGACTTGCGTCCTTCAGGAACT
          750        760        770        780        790        800

910        920        930        940        950        960
naip-o GGCCATTTTATGTCCAAGGGATATCCCCTTGTGTGCTCTCAGAGGCTGGCTTTGTCTTTA
       :::::::::::::::::::::::::::::::::::::::::::::::::::::::::::
naip.s GGCCATTTTATGTCCAAGGGATATCCCCTTGTGTGCTCTCAGAGGCTGGCTTTGTCTTTA
          810        820        830        840        850        860

970        980        990       1000       1010       1020
naip-o CAGGTAAACAGGACACGGTACAGTGTTTTTCCTGTGGTGGATGTTTAGGAAATTGGGAAG
       :::::::::::::::::::::::::::::::::::::::::::::::::::::::::::
naip.s CAGGTAAACAGGACACGGTACAGTGTTTTTCCTGTGGTGGATGTTTAGGAAATTGGGAAG
          870        880        890        900        910        920
```

Fig. 5B

```
              1030       1040       1050       1060       1070       1080
naip-o AAGGAGATGATCCTTGGAAGGAACATGCCAAATGGTTCCCCAAATGTGAATTTCTTCGGA
       ::::::::::::::::::::::::::::::::::::::::::::::::::::::::::::
naip.s AAGGAGATGATCCTTGGAAGGAACATGCCAAATGGTTCCCCAAATGTGAATTTCTTCGGA
              930        940        950        960        970        980

1090       1100       1110       1120       1130       1140
naip-o GTAAGAAATCCTCAGAGGAAATTACCCAGTATATTCAAAGCTACAAGGGATTTGTTGACA
       ::::::::::::::::::::::::::::::::::::::::::::::::::::::::::::
naip.s GTAAGAAATCCTCAGAGGAAATTACCCAGTATATTCAAAGCTACAAGGGATTTGTTGACA
              990        1000       1010       1020       1030       1040

1150       1160       1170       1180       1190       1200
naip-o TAACGGGAGAACATTTTGTGAATTCCTGGGTCCAGAGAGAATTACCTATGGCATCAGCTT
       ::::::::::::::::::::::::::::::::::::::::::::::::::::::::::::
naip.s TAACGGGAGAACATTTTGTGAATTCCTGGGTCCAGAGAGAATTACCTATGGCATCAGCTT
              1050       1060       1070       1080       1090       1100

1210       1220       1230       1240       1250       1260
naip-o ATTGCAATGACAGCATCTTTGCTTACGAAGAACTACGGCTGGACTCTTTTAAGGACTGGC
       ::::::::::::::::::::::::::::::::::::::::::::::::::::::::::::
naip.s ATTGCAATGACAGCATCTTTGCTTACGAAGAACTACGGCTGGACTCTTTTAAGGACTGGC
              1110       1120       1130       1140       1150       1160

1270       1280       1290       1300       1310       1320
naip-o CCCGGGAATCAGCTGTGGGAGTTGCAGCACTGGCCAAAGCAGGTCTTTTCTACACAGGTA
       ::::::::::::::::::::::::::::::::::::::::::::::::::::::::::::
naip.s CCCGGGAATCAGCTGTGGGAGTTGCAGCACTGGCCAAAGCAGGTCTTTTCTACACAGGTA
              1170       1180       1190       1200       1210       1220

1330       1340       1350       1360       1370       1380
naip-o TAAAGGACATCGTCCAGTGCTTTTCCTGTGGAGGGTGTTTAGAGAAATGGCAGGAAGGTG
       ::::::::::::::::::::::::::::::::::::::::::::::::::::::::::::
naip.s TAAAGGACATCGTCCAGTGCTTTTCCTGTGGAGGGTGTTTAGAGAAATGGCAGGAAGGTG
              1230       1240       1250       1260       1270       1280

1390       1400       1410       1420       1430       1440
naip-o ATGACCCATTAGACGATCACACCAGATGTTTTCCCAATTGTCCATTTCTCCAAAATATGA
       ::::::::::::::::::::::::::::::::::::::::::::::::::::::::::::
naip.s ATGACCCATTAGACGATCACACCAGATGTTTTCCCAATTGTCCATTTCTCCAAAATATGA
              1290       1300       1310       1320       1330       1340

1450       1460       1470       1480       1490       1500
naip-o AGTCCTCTGCGGAAGTGACTCCAGACCTTCAGAGCCGTGGTGAACTTTGTGAATTACTGG
       ::::::::::::::::::::::::::::::::::::::::::::::::::::::::::::
naip.s AGTCCTCTGCGGAAGTGACTCCAGACCTTCAGAGCCGTGGTGAACTTTGTGAATTACTGG
              1350       1360       1370       1380       1390       1400

1510       1520       1530       1540       1550       1560
naip-o AAACCACAAGTGAAAGCAATCTTGAAGATTCAATAGCAGTTGGTCCTATAGTGCCAGAAA
       ::::::::::::::::::::::::::::::::::::::::::::::::::::::::::::
naip.s AAACCACAAGTGAAAGCAATCTTGAAGATTCAATAGCAGTTGGTCCTATAGTGCCAGAAA
              1410       1420       1430       1440       1450       1460
```

Fig. 5C

```
            1570      1580      1590      1600      1610      1620
naip-o  TGGCACAGGGTGAAGCCCAGTGGTTTCAAGAGGCAAAGAATCTGAATGAGCAGCTGAGAG
        ::::::::::::::::::::::::::::::::::::::::::::::::::::::::::::
naip.s  TGGCACAGGGTGAAGCCCAGTGGTTTCAAGAGGCAAAGAATCTGAATGAGCAGCTGAGAG
            1470      1480      1490      1500      1510      1520

1630      1640      1650      1660      1670      1680
naip-o  CAGCTTATACCAGCGCCAGTTTCCGCCACATGTCTTTGCTTGATATCTCTTCCGATCTGG
        ::::::::::::::::::::::::::::::::::::::::::::::::::::::::::::
naip.s  CAGCTTATACCAGCGCCAGTTTCCGCCACATGTCTTTGCTTGATATCTCTTCCGATCTGG
            1530      1540      1550      1560      1570      1580

1690      1700      1710      1720      1730      1740
naip-o  CCACGGACCACTTGCTGGGCTGTGATCTGTCTATTGCTTCAAAACACATCAGCAAACCTG
        ::::::::::::::::::::::::::::::::::::::::::::::::::::::::::::
naip.s  CCACGGACCACTTGCTGGGCTGTGATCTGTCTATTGCTTCAAAACACATCAGCAAACCTG
            1590      1600      1610      1620      1630      1640

1750      1760      1770      1780      1790      1800
naip-o  TGCAAGAACCTCTGGTGCTGCCTGAGGTCTTTGGCAACTTGAACTCTGTCATGTGTGTGG
        ::::::::::::::::::::::::::::::::::::::::::::::::::::::::::::
naip.s  TGCAAGAACCTCTGGTGCTGCCTGAGGTCTTTGGCAACTTGAACTCTGTCATGTGTGTGG
            1650      1660      1670      1680      1690      1700

1810      1820      1830      1840      1850      1860
naip-o  AGGGTGAAGCTGGAAGTGGAAAGACGGTCCTCCTGAAGAAAATAGCTTTTCTGTGGGCAT
        ::::::::::::::::::::::::::::::::::::::::::::::::::::::::::::
naip.s  AGGGTGAAGCTGGAAGTGGAAAGACGGTCCTCCTGAAGAAAATAGCTTTTCTGTGGGCAT
            1710      1720      1730      1740      1750      1760

1870      1880      1890      1900      1910      1920
naip-o  CTGGATGCTGTCCCCTGTTAAACAGGTTCCAGCTGGTTTTCTACCTCTCCCTTAGTTCCA
        ::::::::::::::::::::::::::::::::::::::::::::::::::::::::::::
naip.s  CTGGATGCTGTCCCCTGTTAAACAGGTTCCAGCTGGTTTTCTACCTCTCCCTTAGTTCCA
            1770      1780      1790      1800      1810      1820

1930      1940      1950      1960      1970      1980
naip-o  CCAGACCAGACGAGGGGCTGGCCAGTATCATCTGTGACCAGCTCCTAGAGAAAGAAGGAT
        ::::::::::::::::::::::::::::::::::::::::::::::::::::::::::::
naip.s  CCAGACCAGACGAGGGGCTGGCCAGTATCATCTGTGACCAGCTCCTAGAGAAAGAAGGAT
            1830      1840      1850      1860      1870      1880

1990      2000      2010      2020      2030      2040
naip-o  CTGTTACTGAAATGTGCATGAGGAACATTATCCAGCAGTTAAAGAATCAGGTCTTATTCC
        ::::::::::::::::::::::::::::::::::::::::::::::::::::::::::::
naip.s  CTGTTACTGAAATGTGCATGAGGAACATTATCCAGCAGTTAAAGAATCAGGTCTTATTCC
            1890      1900      1910      1920      1930      1940

2050      2060      2070      2080      2090      2100
naip-o  TTTTAGATGACTACAAAGAAATATGTTCAATCCCTCAAGTCATAGGAAAACTGATTCAAA
        ::::::::::::::::::::::::::::::::::::::::::::::::::::::::::::
naip.s  TTTTAGATGACTACAAAGAAATATGTTCAATCCCTCAAGTCATAGGAAAACTGATTCAAA
            1950      1960      1970      1980      1990      2000
```

Fig. 5D

```
         2110      2120      2130      2140      2150      2160
naip-o AAAACCACTTATCCCGGACCTGCCTATTGATTGCTGTCCGTACAAACAGGGCCAGGGACA
       ::::::::::::::::::::::::::::::::::::::::::::::::::::::::::::
naip.s AAAACCACTTATCCCGGACCTGCCTATTGATTGCTGTCCGTACAAACAGGGCCAGGGACA
         2010      2020      2030      2040      2050      2060

2170      2180      2190      2200      2210      2220
naip-o TCCGCCGATACCTAGAGACCATTCTAGAGATCCAAGCATTTCCCTTTTATAATACTGTCT
       ::::::::::::::::::::::::::::::::: :::::::::::::::::::::::::
naip.s TCCGCCGATACCTAGAGACCATTCTAGAGATCAAAGCATTTCCCTTTTATAATACTGTCT
         2070      2080      2090      2100      2110      2120

2230      2240      2250      2260      2270      2280
naip-o GTATATTACGGAAGCTCTTTTCACATAATATGACTCGTCTGCGAAAGTTTATGGTTTACT
       ::::::::::::::::::::::::::::::::::::::::::::::::::::::::::::
naip.s GTATATTACGGAAGCTCTTTTCACATAATATGACTCGTCTGCGAAAGTTTATGGTTTACT
         2130      2140      2150      2160      2170      2180

2290      2300      2310      2320      2330      2340
naip-o TTGGAAAGAACCAAAGTTTGCAGAAGATACAGAAAACTCCTCTCTTTGTGGCGGCGATCT
       ::::::::::::::::::::::::::::::::::::::::::::::::::::::::::::
naip.s TTGGAAAGAACCAAAGTTTGCAGAAGATACAGAAAACTCCTCTCTTTGTGGCGGCGATCT
         2190      2200      2210      2220      2230      2240

2350      2360      2370      2380      2390      2400
naip-o GTGCTCATTGGTTTCAGTATCCTTTTGACCCATCCTTTGATGATGTGGCTGTTTTCAAGT
       ::::::::::::::::::::::::::::::::::::::::::::::::::::::::::::
naip.s GTGCTCATTGGTTTCAGTATCCTTTTGACCCATCCTTTGATGATGTGGCTGTTTTCAAGT
         2250      2260      2270      2280      2290      2300

2410      2420      2430      2440      2450      2460
naip-o CCTATATGGAACGCCTTTCCTTAAGGAACAAAGCGACAGCTGAAATTCTCAAAGCAACTG
       ::::::::::::::::::::::::::::::::::::::::::::::::::::::::::::
naip.s CCTATATGGAACGCCTTTCCTTAAGGAACAAAGCGACAGCTGAAATTCTCAAAGCAACTG
         2310      2320      2330      2340      2350      2360

2470      2480      2490      2500      2510      2520
naip-o TGTCCTCCTGTGGTGAGCTGGCCTTGAAAGGGTTTTTTTCATGTTGCTTTGAGTTTAATG
       ::::::::::::::::::::::::::::::::::::::::::::::::::::::::::::
naip.s TGTCCTCCTGTGGTGAGCTGGCCTTGAAAGGGTTTTTTTCATGTTGCTTTGAGTTTAATG
         2370      2380      2390      2400      2410      2420

2530      2540      2550      2560      2570      2580
naip-o ATGATGATCTCGCAGAAGCAGGGGTTGATGAAGATGAAGATCTAACCATGTGCTTGATGA
       ::::::::::::::::::::::::::::::::::::::::::::::::::::::::::::
naip.s ATGATGATCTCGCAGAAGCAGGGGTTGATGAAGATGAAGATCTAACCATGTGCTTGATGA
         2430      2440      2450      2460      2470      2480

2590      2600      2610      2620      2630      2640
naip-o GCAAATTTACAGCCCAGAGACTAAGACCATTCTACCGGTTTTTAAGTCCTGCCTTCCAAG
       ::::::::::::::::::::::::::::::::::::::::::::::::::::::::::::
naip.s GCAAATTTACAGCCCAGAGACTAAGACCATTCTACCGGTTTTTAAGTCCTGCCTTCCAAG
         2490      2500      2510      2520      2530      2540
```

Fig. 5E

```
                   2650       2660       2670       2680       2690       2700
naip-o  AATTTCTTGCGGGGATGAGGCTGATTGAACTCCTGGATTCAGATAGGCAGGAACATCAAG
        ::::::::::::::::::::::::::::::::::::::::::::::::::::::::::::
naip.s  AATTTCTTGCGGGGATGAGGCTGATTGAACTCCTGGATTCAGATAGGCAGGAACATCAAG
           2550       2560       2570       2580       2590       2600

2710       2720       2730       2740       2750       2760
naip-o  ATTTGGGACTGTATCATTTGAAACAAATCAACTCACCCATGATGACTGTAAGCGCCTACA
        ::::::::::::::::::::::::::::::::::::::::::::::::::::::::::::
naip.s  ATTTGGGACTGTATCATTTGAAACAAATCAACTCACCCATGATGACTGTAAGCGCCTACA
           2610       2620       2630       2640       2650       2660

2770       2780       2790       2800       2810       2820
naip-o  ACAATTTTTTGAACTATGTCTCCAGCCTCCCTTCAACAAAAGCAGGGCCCAAAATTGTGT
        ::::::::::::::::::::::::::::::::::::::::::::::::::::::::::::
naip.s  ACAATTTTTTGAACTATGTCTCCAGCCTCCCTTCAACAAAAGCAGGGCCCAAAATTGTGT
           2670       2680       2690       2700       2710       2720

2830       2840       2850       2860       2870       2880
naip-o  CTCATTTGCTCCATTTAGTGGATAACAAAGAGTCATTGGAGAATATATCTGAAAATGATG
        ::::::::::::::::::::::::::::::::::::::::::::::::::::::::::::
naip.s  CTCATTTGCTCCATTTAGTGGATAACAAAGAGTCATTGGAGAATATATCTGAAAATGATG
           2730       2740       2750       2760       2770       2780

2890       2900       2910       2920       2930       2940
naip-o  ACTACTTAAAGCACCAGCCAGAAATTTCACTGCAGATGCAGTTACTTAGGGGATTGTGGC
        ::::::::::::::::::::::::::::::::::::::::::::::::::::::::::::
naip.s  ACTACTTAAAGCACCAGCCAGAAATTTCACTGCAGATGCAGTTACTTAGGGGATTGTGGC
           2790       2800       2810       2820       2830       2840

2950       2960       2970       2980       2990       3000
naip-o  AAATTTGTCCACAAGCTTACTTTTCAATGGTTTCAGAACATTTACTGGTTCTTGCCCTGA
        ::::::::::::::::::::::::::::::::::::::::::::::::::::::::::::
naip.s  AAATTTGTCCACAAGCTTACTTTTCAATGGTTTCAGAACATTTACTGGTTCTTGCCCTGA
           2850       2860       2870       2880       2890       2900

3010       3020       3030       3040       3050       3060
naip-o  AAACTGCTTATCAAAGCAACACTGTTGCTGCGTGTTCTCCATTTGTTTTGCAATTCCTTC
        ::::::::::::::::::::::::::::::::::::::::::::::::::::::::::::
naip.s  AAACTGCTTATCAAAGCAACACTGTTGCTGCGTGTTCTCCATTTGTTTTGCAATTCCTTC
           2910       2920       2930       2940       2950       2960

3070       3080       3090       3100       3110       3120
naip-o  AAGGGAGAACACTGACTTTGGGTGCGCTTAACTTACAGTACTTTTTCGACCACCCAGAAA
        ::::::::::::::::::::::::::::::::::::::::::::::::::::::::::::
naip.s  AAGGGAGAACACTGACTTTGGGTGCGCTTAACTTACAGTACTTTTTCGACCACCCAGAAA
           2970       2980       2990       3000       3010       3020

3130       3140       3150       3160       3170       3180
naip-o  GCTTGTCATTGTTGAGGAGCATCCACTTCTCAATACGAGGAAATAAGACATCACCCAGAG
        :::::::::::::::::::::::::::::::: :::::::::::::::::::::::::::
naip.s  GCTTGTCATTGTTGAGGAGCATCCACTTCCCAATACGAGGAAATAAGACATCACCCAGAG
           3030       3040       3050       3060       3070       3080
```

Fig. 5F

```
            3190       3200       3210       3220       3230       3240
naip-o CACATTTTTCAGTTCTGGAAACATGTTTTGACAAATCACAGGTGCCAACTATAGATCAGG
       ::::::::::::::::::::::::::::::::::::::::::::::::::::::::::::
naip.s CACATTTTTCAGTTCTGGAAACATGTTTTGACAAATCACAGGTGCCAACTATAGATCAGG
            3090       3100       3110       3120       3130       3140

3250       3260       3270       3280       3290       3300
naip-o ACTATGCTTCTGCCTTTGAACCTATGAATGAATGGGAGCGAAATTTAGCTGAAAAAGAGG
       ::::::::::::::::::::::::::::::::::::::::::::::::::::::::::::
naip.s ACTATGCTTCTGCCTTTGAACCTATGAATGAATGGGAGCGAAATTTAGCTGAAAAAGAGG
            3150       3160       3170       3180       3190       3200

3310       3320       3330       3340       3350       3360
naip-o ATAATGTAAAGAGCTATATGGATATGCAGCGCAGGGCATCACCAGACCTTAGTACTGGCT
       ::::::::::::::::::::::::::::::::::::::::::::::::::::::::::::
naip.s ATAATGTAAAGAGCTATATGGATATGCAGCGCAGGGCATCACCAGACCTTAGTACTGGCT
            3210       3220       3230       3240       3250       3260

3370       3380       3390       3400       3410       3420
naip-o ATTGGAAACTTTCTCCAAAGCAGTACAAGATTCCCTGTCTAGAAGTCGATGTGAATGATA
       ::::::::::::::::::::::::::::::::::::::::::::::::::::::::::::
naip.s ATTGGAAACTTTCTCCAAAGCAGTACAAGATTCCCTGTCTAGAAGTCGATGTGAATGATA
            3270       3280       3290       3300       3310       3320

3430       3440       3450       3460       3470       3480
naip-o TTGATGTTGTAGGCCAGGATATGCTTGAGATTCTAATGACAGTTTTCTCAGCTTCACAGC
       ::::::::::::::::::::::::::::::::::::::::::::::::::::::::::::
naip.s TTGATGTTGTAGGCCAGGATATGCTTGAGATTCTAATGACAGTTTTCTCAGCTTCACAGC
            3330       3340       3350       3360       3370       3380

3490       3500       3510       3520       3530       3540
naip-o GCATCGAACTCCATTTAAACCACAGCAGAGGCTTTATAGAAAGCATCCGCCCAGCTCTTG
       ::::::::::::::::::::::::::::::::::::::::::::::::::::::::::::
naip.s GCATCGAACTCCATTTAAACCACAGCAGAGGCTTTATAGAAAGCATCCGCCCAGCTCTTG
            3390       3400       3410       3420       3430       3440

3550       3560       3570       3580       3590       3600
naip-o AGCTGTCTAAGGCCTCTGTCACCAAGTGCTCCATAAGCAAGTTGGAACTCAGCGCAGCCG
       ::::::::::::::::::::::::::::::::::::::::::::::::::::::::::::
naip.s AGCTGTCTAAGGCCTCTGTCACCAAGTGCTCCATAAGCAAGTTGGAACTCAGCGCAGCCG
            3450       3460       3470       3480       3490       3500

3610       3620       3630       3640       3650       3660
naip-o AACAGGAACTGCTTCTCACCCTGCCTTCCCTGGAATCTCTTGAAGTCTCAGGGACAATCC
       ::::::::::::::::::::::::::::::::::::::::::::::::::::::::::::
naip.s AACAGGAACTGCTTCTCACCCTGCCTTCCCTGGAATCTCTTGAAGTCTCAGGGACAATCC
            3510       3520       3530       3540       3550       3560

3670       3680       3690       3700       3710       3720
naip-o AGTCACAAGACCAAATCTTTCCTAATCTGGATAAGTTCCTGTGCCCTGAAAGAACTGTCTG
       ::::::::::::::::::::::::::::::::::::::::::::::::::::::::::::
naip.s AGTCACAAGACCAAATCTTTCCTAATCTGGATAAGTTCCTGTGCCCTGAAAGAACTGTCTG
            3570       3580       3590       3600       3610       3620
```

Fig. 5G

```
            3730      3740      3750      3760      3770      3780
naip-o  TGGATCTGGAGGGCAATATAAATGTTTTTTCAGTCATTCCTGAAGAATTTCCAAACTTCC
        ::::::::::::::::::::::::::::::::::::::::::::::::::::::::::::
naip.s  TGGATCTGGAGGGCAATATAAATGTTTTTTCAGTCATTCCTGAAGAATTTCCAAACTTCC
            3630      3640      3650      3660      3670      3680

3790      3800      3810      3820      3830      3840
naip-o  ACCATATGGAGAAATTATTGATCCAAATTTCAGCTGAGTATGATCCTTCCAAACTAGTAA
        ::::::::::::::::::::::::::::::::::::::::::::::::::::::::::::
naip.s  ACCATATGGAGAAATTATTGATCCAAATTTCAGCTGAGTATGATCCTTCCAAACTAGTAA
            3690      3700      3710      3720      3730      3740 naip-o  ------------------------------------------------------------ naip.s  AATTAATTCAAAATTCTCCAAACCTTCATGTTTTCCATCTGAAGTGTAACTTCTTTTCGG
            3750      3760      3770      3780      3790      3800 naip-o  ------------------------------------------------------------ naip.s  ATTTTGGGTCTCTCATGACTATGCTTGTTTCCTGTAAGAAACTCACAGAAATTAAGTTTT
            3810      3820      3830      3840      3850      3860

3840      3850      3860
naip-o  ------------------------------------TGCCAGTTTGCCAAATTTTATTTCTCTGA
                                            ::::::::::::::::::::::::::::
naip.s  CGGATTCATTTTTTCAAGCCGTCCCATTTGTTGCCAGTTTGCCAAATTTTATTTCTCTGA
            3870      3880      3890      3900      3910      3920

3870      3880      3890      3900      3910      3920
naip-o  AGATATTAAATCTTGAAGGCCAGCAATTTCCTGATGAGGAAACATCAGAAAAATTTGCCT
        ::::::::::::::::::::::::::::::::::::::::::::::::::::::::::::
naip.s  AGATATTAAATCTTGAAGGCCAGCAATTTCCTGATGAGGAAACATCAGAAAAATTTGCCT
            3930      3940      3950      3960      3970      3980

3930      3940      3950      3960      3970      3980
naip-o  ACATTTTAGGTTCTCTTAGTAACCTGGAAGAATTGATCCTTCCTACTGGGGATGGAATTT
        ::::::::::::::::::::::::::::::::::::::::::::::::::::::::::::
naip.s  ACATTTTAGGTTCTCTTAGTAACCTGGAAGAATTGATCCTTCCTACTGGGGATGGAATTT
            3990      4000      4010      4020      4030      4040

3990      4000      4010      4020      4030      4040
naip-o  ATCGAGTGGCCAAACTGATCATCCAGCAGTGTCAGCAGCTTCATTGTCTCCGAGTCCTCT
        ::::::::::::::::::::::::::::::::::::::::::::::::::::::::::::
naip.s  ATCGAGTGGCCAAACTGATCATCCAGCAGTGTCAGCAGCTTCATTGTCTCCGAGTCCTCT
            4050      4060      4070      4080      4090      4100

4050      4060      4070      4080      4090      4100
naip-o  CATTTTTCAAGACTTTGAATGATGACAGCGTGGTGGAAATTGGTTAAA----AAT--GTG
        :::::::::::::::::::::::::::::::::::::::::::::::    :::  :::
naip.s  CATTTTTCAAGACTTTGAATGATGACAGCGTGGTGGAAATTGCCAAAGTAGCAATCAGTG
            4110      4120      4130      4140      4150      4160
```

Fig. 5H

```
            4110      4120       4130       4140       4150
naip-o ----TCTGCAGGCACAC-AGGACGT---GCCTTCACCCC--CATCTGACTAT-GTGGAAA
          : : ::   ::    :: ::  :    ::  ::::   :    ::    :: ::  :  ::::
naip.s GAGGTTTCCAGAAACTTGAGAACCTAAAGCTTTCAATCAATCACAAGATTACAGAGGAAG
         4170      4180      4190       4200       4210      4220

4160       4170       4180       4190           4200
naip-o GAGTT-GACAGTCCCATGGCATACTCTTCCA-ATGGCAAAGT-----GAAT--GACAAGC
        ::    ::  : : :   :       :::    : : :::  ::::: :       :: :   ::::
naip.s GATACAGAAATTTCTTTCAAGCACTGGACAACATGCCAAACTTGCAGGAGTTGGACATCT
         4230      4240       4250       4260       4270      4280

4210      4220       4230      4240
naip-o ---GGTTTTATCCAGAGTCTTCCTA---TAAATCCACGCCGGT----TCCTGAAGT----
         ::  ::    :::::: : :    :    :  ::::   : ::         ::   :   :::
naip.s CCAGGCATTTCACAGAGTGTATCAAAGCTCAGGCCACAACAGTCAAGTCTTTGAGTCAAT
         4290      4300       4310       4320       4330      4340

4250      4260           4270       4280        4290
naip-o --GGTTCAGGAGCTTCCA-------TTA-ACTTCGCCTGTGGA--TGACTTCAGGCAGCC
         :  :  ::  :: :::       :::  :::    :  :::    :    ::  ::    ::   ::
naip.s GTGTGTTACGA-CTACCAAGGCTCATTAGACTGAACATGTTAAGTTGGCTCTTGGATGCA
         4350      4360       4370       4380       4390      4400

4300       4310      4320       4330       434u
naip-o TC-GTTACAGCAGCG------GTGGTAACTTTGAGACACCTTCAAAAAGAGCAC------
        :  ::  :::  :         ::   : :       :::::  : ::::     ::  ::
naip.s GATGATATTGCATTGCTTAATGTCATGAAAGAAAGACATCCTCAATCTAAGTACTTAACT
         4410      4420       4430       4440       4450      4460

4350        4360      4370       4380          4390
naip-o ---CTGCA--AAGGGA-AGAGCAGGAAGGTCAAAGAGAACAGAGC---AAGAT-CA-CTA
        ::  ::   :: :::   :   :: :       ::  ::     ::::       :::::  ::  :::
naip.s ATTCTCCAGAAATGGATACTGCCGTTCTCTCCAATCATTCAGAAATAAAAGATTCAGCTA
         4470      4480       4490       4500       4510      4520

4400        4410      4420       4430       4440
naip-o TGAGA--CAGACTACACAACTGGCGGCGAGTCCTGT-GATGAGCTGGAGGAGGAC-TGGA
         ::  ::  : ::: :          : : : : :::  ::   :   :  :   :  : ::
naip.s AAAACTGCTGAATCAATAATTTGTCTTGGGGCATATTGAGGATGTAAAAAAAGTTGTTGA
         4530      4540       4550       4560       4570      4580

4450            4460       4470        4480
naip-o TCAGGG-----------AATATCCACC--TATCACTTCAGAT----CA-ACAAAGACAAC
        :   :  :                :  ::::::::      :::      :  : ::   :: ::::::       ::
naip.s TTAATGCTAAAAACCAAATTATCCAAAATTATTTTATTAAATATTGCATACAAAAGAAAA
         4590      4600       4610       4620       4630      4640

4490              4500       4510       4520       4530
naip-o TGT----------------ACAAGAGGAATTTTGACACTGGCCTACAGGAATACAAG--
        :::                  ::::  :  ::     ::::: : :::: ::       ::  :
naip.s TGTGTAAGGCTTGCTAAAAAACAAAACAAAACAAAACACAGTCCTGCATACTCACCACCA
         4650      4660       4670       4680       4690      4700
```

Fig. 51

```
              4540                4550                    4560
naip-o AGCTTAC------AATCAGAAC--------TTGA------TGAG--ATCAA------TA
       :::: :      ::::: ::         ::::      ::::  ::: :       ::
naip.s AGCTCAAGAAATAAATCATCACCAATACCTTTGAGGTCCCTGAGTAATCCACCCCAGCTA
         4710      4720      4730      4740      4750      4760

4570         4580       4590       4600
naip-o AAG---AACTCTCCCGTTTGG---ATAAAGAA-----TTGGATGACTATAGAGAA----G
       :::   ::: :::: ::  :   ::: :: :     :    :: : :: : ::      :
naip.s AAGGCAAACCCTTCAATCAAGTTTATACAGCAAACCCTCCATTGTCCATGGTCAACAGGG
         4770      4780      4790      4800      4810      4820

4610      4620      4630      4640         4650       4660
naip-o AAAGTGAAGAGTACATGGCTGCTGCTG-ATGAATA---CAATAGACTGAAGCA--AGTGA
       :: : :: ::: : ::: : :::: :  : ::      ::   : :   : ::::  : ::
naip.s AAGGGGTTGGGGACAGGTCTGCCAATCTATCTAAAAGCCACAATATGGAAGAAGTATTCA
         4830      4840      4850      4860      4870      4880

4670         4680       4690       4700
naip-o AGGGATCTGC-AGATTACAAAAGTAA--GAAGAATCA-TTGCAAGCA------------G
       :::::::::::::::::::::::::::::::::::::::::::::::::::::::::::
naip.s ATTTATATAATAAATGGCTAACTTAACGGTTGAATCACTTTCATACATGGATGAAACGGG
         4890      4900      4910      4920      4930      4940

4710      4720         4730          4740
naip-o TTAAACAGCAAATTGTCACACATC----------AAGAAGATGGT----------TGGA
       :: ::::    ::    ::   :::            ::::  ::::  :         :: :
naip.s TTTAACACAGGATCCACATGAATCTTCTGTGGGCCAAGA-GATGTTCCTTAATCCTTGTA
         4950      4960      4970      4980      4990      5000

4750      4760      4770
naip-o GA---------CTAT---GA--TAG-------ACAGAA-----AACATAGAAGGC--TGA
       ::         ::::   ::   :::        ::::::      ::: ::     :  : :
naip.s GAACCTGTTTTCTATATTGAACTAGCTTTGGTACAGTAGAGTTAACTTACTTTCCATTTA
         5010      5020      5030      5040      5050      5060

4780         4790         4800       4810         4820
naip.o T-----GCCAAGTTGTTTGAGAAA------TTAAGTATC--TGACATCTCTGCAAT--CT
       :     :::::  :    ::::        ::: : :    :::::: :: : ::       ::
naip.s TCCACTGCCAATATAAAGAGGAAACAGGGGTTAGGGAAAAATGACTTCATTCCAGAGGCT
         5070      5080      5090      5100      5110      5120

4830         4840      4850      4860      4870
naip-o TCTCAGAAGGCAA---ATG----ACTTTGGACCATAACCCCGGAAGCCAAACCTCTGTGA
       :::::::  :::    :::      :  : :::  ::       : :    ::: :::  :  :: ::
naip.s TCTCAGAGTTCAACATATGCTATAATTTAGAATTTT-CTTATGAATCCACTCTACT-TGG
         5130      5140      5150      5160      5170      5180

4880         4890      4900      4910      4920
naip-o GCATCACAGTTTTGGT------TGCTTTAATATCAT--CAGTATTGAAGCATTTTATAA-
       : : : : :: :::  :        :: ::  :::: ::  :   :::   :: ::::  :::
naip.s GTAGAAAATATTTTATCTCTAGTGATTGCATATTATTTCCATATCATAGTATTTCATAGT
         5190      5200      5210      5220      5230      5240

Fig. 5J
```

```
         4930              4940           4950             4960
naip-o ATCGCTTTTGATA-----------ATCAAC-----TGGGCTGAA-------CACTCCAAT
       ::  :::::::           :::::       ::  : :::        :   ::: :
naip.s ATTATATTTGATATGAGTGTCTATATCAATGTCAGTGTCCAGAATTTCGTTCCTACCAGT
         5250      5260      5270      5280      5290      5300

4970           4980            4990         5000
naip-o TAAGGA-TTTTATG-----CTTTAAA--CATTGG---TTCTTG-TATTA--AGAA-----
       :::: : :::: ::     :   ::   :::: :   ::: :: :: ::   : ::
naip.s TAAGTAGTTTTCTGAACGGCCAGAAGACCATTCGAAATTCATGATACTACTATAAGTTGG
         5310      5320      5330      5340      5350      5360

5010           5020
naip-o TGAA-----ATACTGTT----TGAGGTTTTT-------AAG------------------
       : ::     ::::: ::    : :  ::: :              :::
naip.s TAAACAACCATACTTTTATCCTCATTTTTATTCTCACTAAGAAAAAAGTCAACTCCCCTC
         5370      5380      5390      5400      5410      5420

5030                    5040      5050      5060
naip-o -CCTT-----------AAA-----GGAAGGT---TCTGGTGTGAACTAAACTTTC----A
       :::::::::::     :::::::::::::::::::::::::::::::::::::::::::
naip.s CCCTTGCCCAAGTATGAAATATAGGGACAGTATGTATGGTGTGGTCTCATTTGTTTAGAA
         5430      5440      5450      5460      5470      5480

5070      5080        5090                   5100
naip-o CACCCCAGACGA-TGTCTTCA-TACCT---ACATGTA-----------TTTGTTTGCATA
       ::: :  : ::  :  :  :   :  ::    :::: :::::          :: : :: :
naip.s AACCACTTATGACTGGGTGCGGTGGCTCACACCTGTAATCCCAGCACTTTGGGAGGCTGA
         5490      5500      5510      5520      5530      5540

5110      5120                                       5130
naip-o GGTGATC---TCATTT---------AAT----------CCTCTC-----------AACCA
       :: :  :   ::::::          :::          :::  :           ::::
naip.s GGCGGGCGAATCATTTGAGGTGAGGAATTCGAGACCAGCCTGGCCAGCATGGTGAAACCC
         5550      5560      5570      5580      5590      5600

5140                       5150      5160      5170
naip-o CCTTTCAGATAAC------------------TGTTATTTATAATCACTTTTTTCCA---
       :  ::  :::                     :::  :    ::  ::  :   :::
naip.s CATCTCTACTAAAAATACAAAAATTAGCCAGGTGTGGTGGCACATGCCTGTAGTCCCAGC
         5610      5620      5630      5640      5650      5660

5180      5190      5200      5210
naip-o CATAAGG-------------AAACTGGGTT---CCTGCAATGAAGTCTCTGAAGTGAA-
       ::  :::             : ::: : ::   :: :  : : ::    :: :::::
naip.s CACTAGGGCGGCTGAGACGCAAGACTTGCTTGAACCCGGGAGGCAGAGGTTGCAGTGAGC
         5670      5680      5690      5700      5710      5720

5220               5230      5240
naip-o -----------ACTGC-TTGTTTCCT---------AGCAC-ACACTTTTGGTT------
                  ::::: ::  :::            :::: :: :: :  ::
naip.s CAAGATGGCGCCACTGCATTCCAGCCTGGGCAACAGAGCAAGACCCTGTCTGTCTCAAAA
         5730      5740      5750      5760      5770      5780
```

Fig. 5K

```
              5250      5260      5270      5280      5290
naip-o ---------AAGTCTGTTTTATGACTTCATTAATAATAAATTCCGGCATCA--TAC--AG
       ::    ::  :: :::  ::    :  :: :   :::: :  ::     :::   ::
naip.s CAAAAAACAAAACCACTTATATTGCTAGCTACATTAAGAATTTCTGAATATGTTACTGAG
          5790      5800      5810      5820      5830      5840

5300           5310      5320      5330
naip-o CTA-CTCCTC----CC--------TACCGCCACCTCCACAGACACCACTCTCCTGGT---
       ::  ::  :     ::        :: :    :   :    :::::::    : ::  :
naip.s CTTGCTTGTGGTAACCATTTATAATATCAGAAAGTATATGTACACCAAAA-CATGTTGAA
          5850      5860      5870      5880      5890      5900

5340      5350                                5360
naip-o --TCCATCTCCT-CTGCTGC-------------------TTCTAGCTCC------CTGC
       :::::: :  :  :::                        ::  ::  ::       :::
naip.s CATCCATGTTGTACAACTGAAATATAAATAATTTTGTCAATTATACCTAAATAAAACTGG
          5910      5920      5930      5940      5950      5960

5370           5380      5390      5400
naip-o ---------TCTGGC--TTCA---------AGGTGCGCAGGACCTGCTTCCTTG--GTGA
                :::::   :: :          : ::    ::  :  : ::     :   :::
naip.s AAAAAAATTTCTGGAAGTTTATATCTAAAAATGTTAATAGTGCGTACCTCTAGGAAGTGG
          5970      5980      5990      6000      6010      6020

5410      5420      5430      5440      5450      5460
naip-o TCCTCTGTAGTCTCCCACACCCCACATTATCTACAAA-CTGA--TGACTCCTAATTTACA
       :::   :  :: :     :  ::    ::: :::: :   :::    ::  :   :::::
naip.s GCCTG-GAAGCCATTCTTACTTTTCAGTCTCTCCCATTCTGTACTGTTTTTTGTTTTACT
          6030      6040      6050      6060      6070

5470       5480      5490              5500
naip-o TCT---CCAGC-TCAGACCTCTCCATCAATCCCAACGCA---TA------CAC-
       :     :: :: : :    :::    :  :: :  ::    :    ::      :::
naip.s TTCGTGCCTGCATTATTTTTCTATTTAAAACAAAAATAAATCTAGTTTAGCACT
          6080      6090      6100      6110      6120      6130
```

Elapsed time: 0:01:38

Fig. 5L

SEQ ID NO: 21  ACAAAAGGTCCTGTGCTCACCTGGGACCCTTCTGGACGTTGCCCTGTGTACCTCTTCGAC
1              ---------+---------+---------+---------+---------+---------+  60
               TGTTTTCCAGGACACGAGTGGACCCTGGGAAGACCTGCAACGGGACACATGGAGAAGCTG

TGCCTGTTCATCTACGACGAACCCCGGGTATTGACCCCAGACAACAATGCCACTTCATAT
61             ---------+---------+---------+---------+---------+---------+ 120
               ACGGACAAGTAGATGCTGCTTGGGGCCCATAACTGGGGTCTGTTGTTACGGTGAAGTATA

TGGGGACTTCGTCTGGGATTCCAAGGTGCATTCATTGCAAAGTTCCTTAAATATTTTCTC
121            ---------+---------+---------+---------+---------+---------+ 180
               ACCCCTGAAGCAGACCCTAAGGTTCCACGTAAGTAACGTTTCAAGGAATTTATAAAAGAG

ACTGCTTCCTACTAAAGGACGGACAGAGCATTTGTTCTTCAGCCACATACTTTCCTTCCA
181            ---------+---------+---------+---------+---------+---------+ 240
               TGACGAAGGATGATTTCCTGCCTGTCTCGTAAACAAGAAGTCGGTGTATGAAAGGAAGGT

CTGGCCAGCATTCTCCTCTATTAGACTAGAACTGTGGATAAACCTCAGAAAATGGCCACC
241            ---------+---------+---------+---------+---------+---------+ 300
               GACCGGTCGTAAGAGGAGATAATCTGATCTTGACACCTATTTGGAGTCTTTTACCGGTGG
                                                             SEQ ID NO: 22   M  A  T   3

CAGCAGAAAGCCTCTGACGAGAGGATCTCCCAGTTTGATCACAATTTGCTGCCAGAGCTG
301            ---------+---------+---------+---------+---------+---------+ 360
               GTCGTCTTTCGGAGACTGCTCTCCTAGAGGGTCAAACTAGTGTTAAACGACGGTCTCGAC
             4  Q  Q  K  A  S  D  E  R  I  S  Q  F  D  H  N  L  L  P  E  L   23

TCTGCTCTTCTGGGCCTAGATGCAGTTCAGTTGGCAAAGGAACTAGAAGAAGAGGAGCAG
361            ---------+---------+---------+---------+---------+---------+ 420
               AGACGAGAAGACCCGGATCTACGTCAAGTCAACCGTTTCCTTGATCTTCTTCTCCTCGTC
             24 S  A  L  L  G  L  D  A  V  Q  L  A  K  E  L  E  E  E  E  Q   43

AAGGAGCGAGCAAAAATGCAGAAAGGCTACAACTCTCAAATGCGCAGTGAAGCAAAAAGG
421            ---------+---------+---------+---------+---------+---------+ 480
               TTCCTCGCTCGTTTTTACGTCTTTCCGATGTTGAGAGTTTACGCGTCACTTCGTTTTTCC
             44 K  E  R  A  K  M  Q  K  G  Y  N  S  Q  M  R  S  E  A  K  R   63

TTAAAGACTTTTGTGACTTATGAGCCGTACAGCTCATGGATACCACAGGAGATGGCGGCC
481            ---------+---------+---------+---------+---------+---------+ 540
               AATTTCTGAAAACACTGAATACTCGGCATGTCGAGTACCTATGGTGTCCTCTACCGCCGG
             64 L  K  T  F  V  T  Y  E  P  Y  S  S  W  I  P  Q  E  M  A  A   83

GCTGGGTTTTACTTCACTGGGGTAAAATCTGGGATTCAGTGCTTCTGCTGTAGCCTAATC
541            ---------+---------+---------+---------+---------+---------+ 600
               CGACCCAAAATGAAGTGACCCCATTTTAGACCCTAAGTCACGAAGACGACATCGGATTAG
             84 A  G  F  Y  F  T  G  V  K  S  G  I  Q  C  F  C  C  S  L  I   103

CTCTTTGGTGCCGGCCTCACGAGACTCCCCATAGAAGACCACAAGAGGTTTCATCCAGAT
601            ---------+---------+---------+---------+---------+---------+ 660
               GAGAAACCACGGCCGGAGTGCTCTGAGGGGTATCTTCTGGTGTTCTCCAAAGTAGGTCTA
             104 L  F  G  A  G  L  T  R  L  P  I  E  D  H  K  R  F  H  P  D   123

Fig. 6A

```
                TGTGGGTTCCTTTTGAACAAGGATGTTGGTAACATTGCCAAGTACGACATAAGGGTGAAG
661             ------------+---------+---------+---------+---------+---------+  720
                ACACCCAAGGAAAACTTGTTCCTACAACCATTGTAACGGTTCATGCTGTATTCCCACTTC
124      C  G  F  L  L  N  K  D  V  G  N  I  A  K  Y  D  I  R  V  K    143

AATCTGAAGAGCAGGCTGAGAGGAGGTAAAATGAGGTACCAAGAAGAGGAGGCTAGACTT
721             ------------+---------+---------+---------+---------+---------+  780
                TTAGACTTCTCGTCCGACTCTCCTCCATTTTACTCCATGGTTCTTCTCCTCCGATCTGAA
144      N  L  K  S  R  L  R  G  G  K  M  R  Y  Q  E  E  E  A  R  L    163

GCGTCCTTCAGGAACTGGCCATTTTATGTCCAAGGGATATCCCCTTGTGTGCTCTCAGAG
781             ------------+---------+---------+---------+---------+---------+  840
                CGCAGGAAGTCCTTGACCGGTAAAATACAGGTTCCCTATAGGGGAACACACGAGAGTCTC
164      A  S  F  R  N  W  P  F  Y  V  Q  G  I  S  P  C  V  L  S  E    183

GCTGGCTTTGTCTTTACAGGTAAACAGGACACGGTACAGTGTTTTTCCTGTGGTGGATGT
841             ------------+---------+---------+---------+---------+---------+  900
                CGACCGAAACAGAAATGTCCATTTGTCCTGTGCCATGTCACAAAAAGGACACCACCTACA
184      A  G  F  V  F  T  G  K  Q  D  T  V  Q  C  F  S  C  G  G  C    203

TTAGGAAATTGGGAAGAAGGAGATGATCCTTGGAAGGAACATGCCAAATGGTTCCCCAAA
901             ------------+---------+---------+---------+---------+---------+  960
                AATCCTTTAACCCTTCTTCCTCTACTAGGAACCTTCCTTGTACGGTTTACCAAGGGGTTT
204      L  G  N  W  E  E  G  D  D  P  W  K  E  H  A  K  W  F  P  K    223

TGTGAATTTCTTCGGAGTAAGAAATCCTCAGAGGAAATTACCCAGTATATTCAAAGCTAC
961             ------------+---------+---------+---------+---------+---------+  1020
                ACACTTAAAGAAGCCTCATTCTTTAGGAGTCTCCTTTAATGGGTCATATAAGTTTCGATG
224      C  E  F  L  R  S  K  K  S  S  E  E  I  T  Q  Y  I  Q  S  Y    243
                                  6  7
                AAGGGATTTGTTGACATAACGGGAGAACATTTTGTGAATTCCTGGGTCCAGAGAGAATTA
1021            ------------+---------+---------+---------+---------+---------+  1080
                TTCCCTAAACAACTGTATTGCCCTCTTGTAAAACACTTAAGGACCCAGGTCTCTCTTAAT
244      K  G  F  V  D  I  T  G  E  H  F  V  N  S  W  V  Q  R  E  L    263
                                  7  8
                CCTATGGCATCAGCTTATTGCAATGACAGCATCTTTGCTTACGAAGAACTACGGCTGGAC
1081            ------------+---------+---------+---------+---------+---------+  1140
                GGATACCGTAGTCGAATAACGTTACTGTCGTAGAAACGAATGCTTCTTGATGCCGACCTG
264      P  M  A  S  A  Y  C  N  D  S  I  F  A  Y  E  E  L  R  L  D    283

TCTTTTAAGGACTGGCCCCGGGAATCAGCTGTGGGAGTTGCAGCACTGGCCAAAGCAGGT
1141            ------------+---------+---------+---------+---------+---------+  1200
                AGAAAATTCCTGACCGGGGCCCTTAGTCGACACCCTCAACGTCGTGACCGGTTTCGTCCA
284      S  F  K  D  W  P  R  E  S  A  V  G  V  A  A  L  A  K  A  G    303

CTTTTCTACACAGGTATAAAGGACATCGTCCAGTGCTTTTCCTGTGGAGGGTGTTTAGAG
1201            ------------+---------+---------+---------+---------+---------+  1260
                GAAAAGATGTGTCCATATTTCCTGTAGCAGGTCACGAAAAGGACACCTCCCACAAATCTC
304      L  F  Y  T  G  I  K  D  I  V  Q  C  F  S  C  G  G  C  L  E    323
                           910
                AAATGGCAGGAAGGTGATGACCCATTAGACGATCACACCAGATGTTTTCCCAATTGTCCA
1261            ------------+---------+---------+---------+---------+---------+  1320
                TTTACCGTCCTTCCACTACTGGGTAATCTGCTAGTGTGGTCTACAAAAGGGTTAACAGGT
324      K  W  Q  E  G  D  D  P  L  D  D  H  T  R  C  F  P  N  C  P    343
```

Fig. 6B

```
     TTTCTCCAAAATATGAAGTCCTCTGCGGAAGTGACTCCAGACCTTCAGAGCCGTGGTGAA
1321 ------------------------------------------------------------ 1380
     AAAGAGGTTTTATACTTCAGGAGACGCCTTCACTGAGGTCTGGAAGTCTCGGCACCACTT
 344 F  L  Q  N  M  K  S  S  A  E  V  T  P  D  L  Q  S  R  G  E   363

CTTTGTGAATTACTGGAAACCACAAGTGAAAGCAATCTTGAAGATTCAATAGCAGTTGGT
1381 ------------------------------------------------------------ 1440
     GAAACACTTAATGACCTTTGGTGTTCACTTTCGTTAGAACTTCTAAGTTATCGTCAACCA
 364 L  C  E  L  L  E  T  T  S  E  S  N  L  E  D  S  I  A  V  G   383

CCTATAGTGCCAGAAATGGCACAGGGTGAAGCCCAGTGGTTTCAAGAGGCAAAGAATCTG
1441 ------------------------------------------------------------ 1500
     GGATATCACGGTCTTTACCGTGTCCCACTTCGGGTCACCAAAGTTCTCCGTTTCTTAGAC
 384 P  I  V  P  E  M  A  Q  G  E  A  Q  W  F  Q  E  A  K  N  L   403

AATGAGCAGCTGAGAGCAGCTTATACCAGCGCCAGTTTCCGCCACATGTCTTTGCTTGAT
1501 ------------------------------------------------------------ 1560
     TTACTCGTCGACTCTCGTCGAATATGGTCGCGGTCAAAGGCGGTGTACAGAAACGAACTA
 404 N  E  Q  L  R  A  A  Y  T  S  A  S  F  R  H  M  S  L  L  D   423

ATCTCTTCCGATCTGGCCACGGACCACTTGCTGGGCTGTGATCTGTCTATTGCTTCAAAA
1561 ------------------------------------------------------------ 1620
     TAGAGAAGGCTAGACCGGTGCCTGGTGAACGACCCGACACTAGACAGATAACGAAGTTTT
 424 I  S  S  D  L  A  T  D  H  L  L  G  C  D  L  S  I  A  S  K   443

CACATCAGCAAACCTGTGCAAGAACCTCTGGTGCTGCCTGAGGTCTTTGGCAACTTGAAC
1621 ------------------------------------------------------------ 1680
     GTGTAGTCGTTTGGACACGTTCTTGGAGACCACGACGGACTCCAGAAACCGTTGAACTTG
 444 H  I  S  K  P  V  Q  E  P  L  V  L  P  E  V  F  G  N  L  N   463

TCTGTCATGTGTGTGGAGGGTGAAGCTGGAAGTGGAAAGACGGTCCTCCTGAAGAAAATA
1681 ------------------------------------------------------------ 1740
     AGACAGTACACACACCTCCCACTTCGACCTTCACCTTTCTGCCAGGAGGACTTCTTTTAT
 464 S  V  M  C  V  E  G  E  A  G  S  G  K  T  V  L  L  K  K  I   483

GCTTTTCTGTGGGCATCTGGATGCTGTCCCCTGTTAAACAGGTTCCAGCTGGTTTTCTAC
1741 ------------------------------------------------------------ 1800
     CGAAAAGACACCCGTAGACCTACGACAGGGGACAATTTGTCCAAGGTCGACCAAAAGATG
 484 A  F  L  W  A  S  G  C  C  P  L  L  N  R  F  Q  L  V  F  Y   503

CTCTCCCTTAGTTCCACCAGACCAGACGAGGGGCTGGCCAGTATCATCTGTGACCAGCTC
1801 ------------------------------------------------------------ 1860
     GAGAGGGAATCAAGGTGGTCTGGTCTGCTCCCCGACCGGTCATAGTAGACACTGGTCGAG
 504 L  S  L  S  S  T  R  P  D  E  G  L  A  S  I  I  C  D  Q  L   523

CTAGAGAAAGAAGGATCTGTTACTGAAATGTGCATGAGGAACATTATCCAGCAGTTAAAG
1861 ------------------------------------------------------------ 1920
     GATCTCTTTCTTCCTAGACAATGACTTTACACGTACTCCTTGTAATAGGTCGTCAATTTC
 524 L  E  K  E  G  S  V  T  E  M  C  M  R  N  I  I  Q  Q  L  K   543

AATCAGGTCTTATTCCTTTTAGATGACTACAAAGAAATATGTTCAATCCCTCAAGTCATA
1921 ------------------------------------------------------------ 1980
     TTAGTCCAGAATAAGGAAAATCTACTGATGTTTCTTTATACAAGTTAGGGAGTTCAGTAT
 544 N  Q  V  L  F  L  L  D  D  Y  K  E  I  C  S  I  P  Q  V  I   563
```

Fig. 6C

```
         GGAAAACTGATTCAAAAAAACCACTTATCCCGGACCTGCCTATTGATTGCTGTCCGTACA
1981     ------------+---------+---------+---------+---------+---------+    2040
         CCTTTTGACTAAGTTTTTTTGGTGAATAGGGCCTGGACGGATAACTAACGAC AGGCATGT
  564  G  K  L  I  Q  K  N  H  L  S  R  T  C  L  L  I  A  V  R  T         583

AACAGGGCCAGGGACATCCGCCGATACCTAGAGACCATTCTAGAGATCAAAGCATTTCCC
2041     ------------+---------+---------+---------+---------+---------+    2100
         TTGTCCCGGTCCCTGTAGGCGGCTATGGATCTCTGGTAAGATCTCTAGTTTCGTAAAGGG
  584  N  R  A  R  D  I  R  R  Y  L  E  T  I  L  E  I  K  A  F  P         603

TTTTATAATACTGTCTGTATATTACGGAAGCTCTTTTCACATAATATGACTCGTCTGCGA
2101     ------------+---------+---------+---------+---------+---------+    2160
         AAAATATTATGACAGACATATAATGCCTTCGAGAAAAGTGTATTATACTGAGCAGACGCT
  604  F  Y  N  T  V  C  I  L  R  K  L  F  S  H  N  M  T  R  L  R         623

AAGTTTATGGTTTACTTTGGAAAGAACCAAAGTTTGCAGAAGATACAGAAAACTCCTCTC
2161     ------------+---------+---------+---------+---------+---------+    2220
         TTCAAATACCAAATGAAACCTTTCTTGGTTTCAAACGTCTTCTATGTCTTTTGAGGAGAG
  624  K  F  M  V  Y  F  G  K  N  Q  S  L  Q  K  I  Q  K  T  P  L         643

TTTGTGGCGGCGATCTGTGCTCATTGGTTTCAGTATCCTTTTGACCCATCCTTTGATGAT
2221     ------------+---------+---------+---------+---------+---------+    2280
         AAACACCGCCGCTAGACACGAGTAACCAAAGTCATAGGAAAACTGGGTAGGAAACTACTA
  644  F  V  A  A  I  C  A  H  W  F  Q  Y  P  F  D  P  S  F  D  D         663

GTGGCTGTTTTCAAGTCCTATATGGAACGCCTTTCCTTAAGGAACAAAGCGACAGCTGAA
2281     ------------+---------+---------+---------+---------+---------+    2340
         CACCGACAAAAGTTCAGGATATACCTTGCGGAAAGGAATTCCTTGTTTCGCTGTCGACTT
  664  V  A  V  F  K  S  Y  M  E  R  L  S  L  R  N  K  A  T  A  E         683

ATTCTCAAAGCAACTGTGTCCTCCTGTGGTGAGCTGGCCTTGAAAGGGTTTTTTTCATGT
2341     ------------+---------+---------+---------+---------+---------+    2400
         TAAGAGTTTCGTTGACACAGGAGGACACCACTCGACCGGAACTTTCCCAAAAAAAGTACA
  684  I  L  K  A  T  V  S  S  C  G  E  L  A  L  K  G  F  F  S  C         703

TGCTTTGAGTTTAATGATGATGATCTCGCAGAAGCAGGGGTTGATGAAGATGAAGATCTA
2401     ------------+---------+---------+---------+---------+---------+    2460
         ACGAAACTCAAATTACTACTACTAGAGCGTCTTCGTCCCCAACTACTTCTACTTCTAGAT
  704  C  F  E  F  N  D  D  D  L  A  E  A  G  V  D  E  D  E  D  L         723

ACCATGTGCTTGATGAGCAAATTTACAGCCCAGAGACTAAGACCATTCTACCGGTTTTTA
2461     ------------+---------+---------+---------+---------+---------+    2520
         TGGTACACGAACTACTCGTTTAAATGTCGGGTCTCTGATTCTGGTAAGATGGCCAAAAAT
  724  T  M  C  L  M  S  K  F  T  A  Q  R  L  R  P  F  Y  R  F  L         743

AGTCCTGCCTTCCAAGAATTTCTTGCGGGGATGAGGCTGATTGAACTCCTGGATTCAGAT
2521     ------------+---------+---------+---------+---------+---------+    2580
         TCAGGACGGAAGGTTCTTAAAGAACGCCCCTACTCCGACTAACTTGAGGACCTAAGTCTA
  744  S  P  A  F  Q  E  F  L  A  G  M  R  L  I  E  L  L  D  S  D         763

AGGCAGGAACATCAAGATTTGGGACTGTATCATTTGAAACAAATCAACTCACCCATGATG
2581     ------------+---------+---------+---------+---------+---------+    2640
         TCCGTCCTTGTAGTTCTAAACCCTGACATAGTAAACTTTGTTTAGTTGAGTGGGTACTAC
  764  R  Q  E  H  Q  D  L  G  L  Y  H  L  K  Q  I  N  S  P  M  M         783
```

Fig. 6D

```
          ACTGTAAGCGCCTACAACAATTTTTTGAACTATGTCTCCAGCCTCCCTTCAACAAAAGCA
2641      ---------+---------+---------+---------+---------+---------+    2700
          TGACATTCGCGGATGTTGTTAAAAAACTTGATACAGAGGTCGGAGGGAAGTTGTTTTCGT
784   T  V  S  A  Y  N  N  F  L  N  Y  V  S  S  L  P  S  T  K  A      803

GGGCCCAAAATTGTGTCTCATTTGCTCCATTTAGTGGATAACAAAGAGTCATTGGAGAAT
2701      ---------+---------+---------+---------+---------+---------+    2760
          CCCGGGTTTTAACACAGAGTAAACGAGGTAAATCACCTATTGTTTCTCAGTAACCTCTTA
804   G  P  K  I  V  S  H  L  L  H  L  V  D  N  K  E  S  L  E  N      823

ATATCTGAAAATGATGACTACTTAAAGCACCAGCCAGAAATTTCACTGCAGATGCAGTTA
2761      ---------+---------+---------+---------+---------+---------+    2820
          TATAGACTTTTACTACTGATGAATTTCGTGGTCGGTCTTTAAAGTGACGTCTACGTCAAT
824   I  S  E  N  D  D  Y  L  K  H  Q  P  E  I  S  L  Q  M  Q  L      843

CTTAGGGGATTGTGGCAAATTTGTCCACAAGCTTACTTTTCAATGGTTTCAGAACATTTA
2821      ---------+---------+---------+---------+---------+---------+    2880
          GAATCCCCTAACACCGTTTAAACAGGTGTTCGAATGAAAAGTTACCAAAGTCTTGTAAAT
844   L  R  G  L  W  Q  I  C  P  Q  A  Y  F  S  M  V  S  E  H  L      863

CTGGTTCTTGCCCTGAAAACTGCTTATCAAAGCAACACTGTTGCTGCGTGTTCTCCATTT
2881      ---------+---------+---------+---------+---------+---------+    2940
          GACCAAGAACGGGACTTTTGACGAATAGTTTCGTTGTGACAACGACGCACAAGAGGTAAA
864   L  V  L  A  L  K  T  A  Y  Q  S  N  T  V  A  A  C  S  P  F      883

GTTTTGCAATTCCTTCAAGGGAGAACACTGACTTTGGGTGCGCTTAACTTACAGTACTTT
2941      ---------+---------+---------+---------+---------+---------+    3000
          CAAAACGTTAAGGAAGTTCCCTCTTGTGACTGAAACCCACGCGAATTGAATGTCATGAAA
884   V  L  Q  F  L  Q  G  R  T  L  T  L  G  A  L  N  L  Q  Y  F      903

TTCGACCACCCAGAAAGCTTGTCATTGTTGAGGAGCATCCACTTCCCAATACGAGGAAAT
3001      ---------+---------+---------+---------+---------+---------+    3060
          AAGCTGGTGGGTCTTTCGAACAGTAACAACTCCTCGTAGGTGAAGGGTTATGCTCCTTTA
904   F  D  H  P  E  S  L  S  L  L  R  S  I  H  F  P  I  R  G  N      923

AAGACATCACCCAGAGCACATTTTTCAGTTCTGGAAACATGTTTTGACAAATCACAGGTG
3061      ---------+---------+---------+---------+---------+---------+    3120
          TTCTGTAGTGGGTCTCGTGTAAAAAGTCAAGACCTTTGTACAAAACTGTTTAGTGTCCAC
924   K  T  S  P  R  A  H  F  S  V  L  E  T  C  F  D  K  S  Q  V      943

CCAACTATAGATCAGGACTATGCTTCTGCCTTTGAACCTATGAATGAATGGGAGCGAAAT
3121      ---------+---------+---------+---------+---------+---------+    3180
          GGTTGATATCTAGTCCTGATACGAAGACGGAAACTTGGATACTTACTTACCCTCGCTTTA
944   P  T  I  D  Q  D  Y  A  S  A  F  E  P  M  N  E  W  E  R  N      963

TTAGCTGAAAAAGAGGATAATGTAAAGAGCTATATGGATATGCAGCGCAGGGCATCACCA
3181      ---------+---------+---------+---------+---------+---------+    3240
          AATCGACTTTTTCTCCTATTACATTTCTCGATATACCTATACGTCGCGTCCCGTAGTGGT
964   L  A  E  K  E  D  N  V  K  S  Y  M  D  M  Q  R  R  A  S  P      983

GACCTTAGTACTGGCTATTGGAAACTTTCTCCAAAGCAGTACAAGATTCCCTGTCTAGAA
3241      ---------+---------+---------+---------+---------+---------+    3300
          CTGGAATCATGACCGATAACCTTTGAAAGAGGTTTCGTCATGTTCTAAGGGACAGATCTT
984   D  L  S  T  G  Y  W  K  L  S  P  K  Q  Y  K  I  P  C  L  E      1003
```

Fig. 6E

```
        GTCGATGTGAATGATATTGATGTTGTAGGCCAGGATATGCTTGAGATTCTAATGACAGTT
3301    ---------+---------+---------+---------+---------+---------+    3360
        CAGCTACACTTACTATAACTACAACATCCGGTCCTATACGAACTCTAAGATTACTGTCAA
1004    V  D  V  N  D  I  D  V  V  G  Q  D  M  L  E  I  L  M  T  V     1023

TTCTCAGCTTCACAGCGCATCGAACTCCATTTAAACCACAGCAGAGGCTTTATAGAAAGC
3361    ---------+---------+---------+---------+---------+---------+    3420
        AAGAGTCGAAGTGTCGCGTAGCTTGAGGTAAATTTGGTGTCGTCTCCGAAATATCTTTCG
1024    F  S  A  S  Q  R  I  E  L  H  L  N  H  S  R  G  F  I  E  S     1043

ATCCGCCCAGCTCTTGAGCTGTCTAAGGCCTCTGTCACCAAGTGCTCCATAAGCAAGTTG
3421    ---------+---------+---------+---------+---------+---------+    3480
        TAGGCGGGTCGAGAACTCGACAGATTCCGGAGACAGTGGTTCACGAGGTATTCGTTCAAC
1044    I  R  P  A  L  E  L  S  K  A  S  V  T  K  C  S  I  S  K  L     1063

GAACTCAGCGCAGCCGAACAGGAACTGCTTCTCACCCTGCCTTCCCTGGAATCTCTTGAA
3481    ---------+---------+---------+---------+---------+---------+    3540
        CTTGAGTCGCGTCGGCTTGTCCTTGACGAAGAGTGGGACGGAAGGGACCTTAGAGAACTT
1064    E  L  S  A  A  E  Q  E  L  L  L  T  L  P  S  L  E  S  L  E     1083
                                  12 13
        GTCTCAGGGACAATCCAGTCACAAGACCAAATCTTTCCTAATCTGGATAAGTTCCTGTGC
3541    ---------+---------+---------+---------+---------+---------+    3600
        CAGAGTCCCTGTTAGGTCAGTGTTCTGGTTTAGAAAGGATTAGACCTATTCAAGGACACG
1084    V  S  G  T  I  Q  S  Q  D  Q  I  F  P  N  L  D  K  F  L  C     1103

CTGAAAGAACTGTCTGTGGATCTGGAGGGCAATATAAATGTTTTTTCAGTCATTCCTGAA
3601    ---------+---------+---------+---------+---------+---------+    3660
        GACTTTCTTGACAGACACCTAGACCTCCCGTTATATTTACAAAAAAGTCAGTAAGGACTT
1104    L  K  E  L  S  V  D  L  E  G  N  I  N  V  F  S  V  I  P  E     1123

GAATTTCCAAACTTCCACCATATGGAGAAATTATTGATCCAAATTTCAGCTGAGTATGAT
3661    ---------+---------+---------+---------+---------+---------+    3720
        CTTAAAGGTTTGAAGGTGGTATACCTCTTTAATAACTAGGTTTAAAGTCGACTCATACTA
1124    E  F  P  N  F  H  H  M  E  K  L  L  I  Q  I  S  A  E  Y  D     1143

CCTTCCAAACTAGTAAAATTAATTCAAAATTCTCCAAACCTTCATGTTTTCCATCTGAAG
3721    ---------+---+-----+---------+---------+---------+---------+    3780
        GGAAGGTTTGATCATTTTAATTAAGTTTTAAGAGGTTTGGAAGTACAAAAGGTAGACTTC
1144    P  S  K  L  V  K  L  I  Q  N  S  P  N  L  H  V  F  H  L  K     1163

TGTAACTTCTTTTCGGATTTTGGGTCTCTCATGACTATGCTTGTTTCCTGTAAGAAACTC
3781    ---------+---------+---------+---------+---------+---------+    3840
        ACATTGAAGAAAAGCCTAAAACCCAGAGAGTACTGATACGAACAAAGGACATTCTTTGAG
1164    C  N  F  F  S  D  F  G  S  L  M  T  M  L  V  S  C  K  K  L     1183

ACAGAAATTAAGTTTTCGGATTCATTTTTTCAAGCCGTCCCATTTGTTGCCAGTTTGCCA
3841    ---------+---------+---------+---------+--------+---------+     3900
        TGTCTTTAATTCAAAAGCCTAAGTAAAAAAGTTCGGCAGGGTAAACAACGGTCAAACGGT
1184    T  E  I  K  F  S  D  S  F  F  Q  A  V  P  F  V  A  S  L  P     1203

AATTTTATTTCTCTGAAGATATTAAATCTTGAAGGCCAGCAATTTCCTGATGAGGAAACA
3901    ---------+---------+---------+---------+---------+---------+    3960
        TTAAAATAAAGAGACTTCTATAATTTAGAACTTCCGGTCGTTAAAGGACTACTCCTTTGT
1204    N  F  I  S  L  K  I  L  N  L  E  G  Q  Q  F  P  D  E  E  T     1223
```

Fig. 6F

```
             TCAGAAAAATTTGCCTACATTTTAGGTTCTCTTAGTAACCTGGAAGAATTGATCCTTCCT
3961     ---------+---------+---------+---------+---------+---------+     4020
             AGTCTTTTTAAACGGATGTAAAATCCAAGAGAATCATTGGACCTTCTTAACTAGGAAGGA
1224     S   E   K   F   A   Y   I   L   G   S   L   S   N   L   E   E   I   L   P       1243

ACTGGGGATGGAATTTATCGAGTGGCCAAACTGATCATCCAGCAGTGTCAGCAGCTTCAT
4021     ---------+---------+---------+---------+---------+---------+     4080
             TGACCCCTACCTTAAATAGCTCACCGGTTTGACTAGTAGGTCGTCACAGTCGTCGAAGTA
1244     T   G   D   G   I   Y   R   V   A   K   L   I   I   Q   Q   C   Q   Q   L   H       1263
                     16  17
             TGTCTCCGAGTCCTCTCATTTTTCAAGACTTTGAATGATGACAGCGTGGTGGAAATTGCC
4081     ---------+---------+---------+---------+---------+---------+     4140
             ACAGAGGCTCAGGAGAGTAAAAAGTTCTGAAACTTACTACTGTCGCACCACCTTTAACGG
1264     C   L   R   V   L   S   F   F   K   T   L   N   D   D   S   V   V   E   I   A       1283

AAAGTAGCAATCAGTGGAGGTTTCCAGAAACTTGAGAACCTAAAGCTTTCAATCAATCAC
4141     ---------+---------+---------+---------+---------+---------+     4200
             TTTCATCGTTAGTCACCTCCAAAGGTCTTTGAACTCTTGGATTTCGAAAGTTAGTTAGTG
1284     K   V   A   I   S   G   G   F   Q   K   L   E   N   L   K   L   S   I   N   H       1303

AAGATTACAGAGGAAGGATACAGAAATTTCTTTCAAGCACTGGACAACATGCCAAACTTG
4201     ---------+---------+---------+---------+---------+---------+     4260
             TTCTAATGTCTCCTTCCTATGTCTTTAAAGAAAGTTCGTGACCTGTTGTACGGTTTGAAC
1304     K   I   T   E   E   G   Y   R   N   F   F   Q   A   L   D   N   M   P   N   L       1323

CAGGAGTTGGACATCTCCAGGCATTTCACAGAGTGTATCAAAGCTCAGGCCACAACAGTC
4261     ---------+---------+---------+---------+---------+---------+     4320
               GTCCTCAACCTGTAGAGGTCCGTAAAGTGTCTCACATAGTTTCGAGTCCGGTGTTGTCAG
1324     Q   E   L   D   I   S   R   H   F   T   E   C   I   K   A   Q   A   T   T   V       1343

AAGTCTTTGAGTCAATGTGTGTTACGACTACCAAGGCTCATTAGACTGAACATGTTAAGT
4321     ---------+---------+---------+---------+---------+---------+     4380
             TTCAGAAACTCAGTTACACACAATGCTGATGGTTCCGAGTAATCTGACTTGTACAATTCA
1344     K   S   L   S   Q   C   V   L   R   L   P   R   L   I   R   L   N   M   L   S       1363

TGGCTCTTGGATGCAGATGATATTGCATTGCTTAATGTCATGAAAGAAAGACATCCTCAA
4381     ---------+---------+---------+---------+---------+---------+     4440
             ACCGAGAACCTACGTCTACTATAACGTAACGAATTACAGTACTTTCTTTCTGTAGGAGTT
1364     W   L   L   D   A   D   D   I   A   L   L   N   V   M   K   E   R   H   P   Q       1383

TCTAAGTACTTAACTATTCTCCAGAAATGGATACTGCCGTTCTCTCCAATCATTCAGAAA
4441     ---------+---------+---------+---------+---------+---------+     4500
             AGATTCATGAATTGATAAGAGGTCTTTACCTATGACGGCAAGAGAGGTTAGTAAGTCTTT
1384     S   K   Y   L   T   I   L   Q   K   W   I   L   P   F   S   P   I   I   Q   K       1403

TAAAAGATTCAGCTAAAAACTGCTGAATCAATAATTTGTCTTGGGGCATATTGAGGATGT
4501     ---------+---------+---------+---------+---------+---------+     4560
             ATTTTCTAAGTCGATTTTTGACGACTTAGTTATTAAACAGAACCCCGTATAACTCCTACA
1404     *                                                                                   1423

AAAAAAAGTTGTTGATTAATGCTAAAAACCAAATTATCCAAAATTATTTTATTAAATATT
4561     ---------+---------+---------+---------+---------+---------+     4620
             TTTTTTTCAACAACTAATTACGATTTTTGGTTTAATAGGTTTTAATAAAATAATTTATAA
```

Fig. 6G

```
       GCATACAAAAGAAAATGTGTAAGGCTTGCTAAAAAACAAAACAAAACAAAACACAGTCCT
4621   ------------+---------+---------+---------+---------+---------+   4680
       CGTATGTTTTCTTTTACACATTCCGAACGATTTTTGTTTTGTTTTGTTTTGTGTCAGGA

GCATACTCACCACCAAGCTCAAGAAATAAATCATCACCAATACCTTTGAGGTCCCTGAGT
4681   ------------+---------+---------+---------+---------+---------+   4740
       CGTATGAGTGGTGGTTCGAGTTCTTTATTTAGTAGTGGTTATGGAAACTCCAGGGACTCA

AATCCACCCCAGCTAAAGGCAAACCCTTCAATCAAGTTTATACAGCAAACCCTCCATTGT
4741   ------------+---------+---------+---------+---------+---------+   4800
       TTAGGTGGGGTCGATTTCCGTTTGGGAAGTTAGTTCAAATATGTCGTTTGGGAGGTAACA

CCATGGTCAACAGGGAAGGGGTTGGGGACAGGTCTGCCAATCTATCTAAAAGCCACAATA
4801   ------------+---------+---------+---------+---------+---------+   4860
       GGTACCAGTTGTCCCTTCCCCAACCCCTGTCCAGACGGTTAGATAGATTTTCGGTGTTAT

TGGAAGAAGTATTCAATTTATATAATAAATGGCTAACTTAACGGTTGAATCACTTTCATA
4861   ------------+---------+---------+---------+---------+---------+   4920
       ACCTTCTTCATAAGTTAAATATATTATTTACCGATTGAATTGCCAACTTAGTGAAAGTAT

CATGGATGAAACGGGTTTAACACAGGATCCACATGAATCTTCTGTGGGCCAAGAGATGTT
4921   ------------+---------+---------+---------+---------+---------+   4980
       GTACCTACTTTGCCCAAATTGTGTCCTAGGTGTACTTAGAAGACACCCGGTTCTCTACAA

CCTTAATCCTTGTAGAACCTGTTTTCTATATTGAACTAGCTTTGGTACAGTAGAGTTAAC
4981   ------------+---------+---------+---------+---------+---------+   5040
       GGAATTAGGAACATCTTGGACAAAAGATATAACTTGATCGAAACCATGTCATCTCAATTG

TTACTTTCCATTTATCCACTGCCAATATAAAGAGGAAACAGGGGTTAGGGAAAAATGACT
5041   ------------+---------+---------+---------+---------+---------+   5100
       AATGAAAGGTAAATAGGTGACGGTTATATTTCTCCTTTGTCCCCAATCCCTTTTTACTGA

TCATTCCAGAGGCTTCTCAGAGTTCAACATATGCTATAATTTAGAATTTTCTTATGAATC
5101   ------------+---------+---------+---------+---------+---------+   5160
       AGTAAGGTCTCCGAAGAGTCTCAAGTTGTATACGATATTAAATCTTAAAAGAATACTTAG

CACTCTACTTGGGTAGAAAATATTTTATCTCTAGTGATTGCATATTATTTCCATATCATA
5161   ------------+---------+---------+---------+---------+---------+   5220
       GTGAGATGAACCCATCTTTTATAAAATAGAGATCACTAACGTATAATAAAGGTATAGTAT

GTATTTCATAGTATTATATTTGATATGAGTGTCTATATCAATGTCAGTGTCCAGAATTTC
5221   ------------+---------+---------+---------+---------+---------+   5280
       CATAAAGTATCATAATATAAACTATACTCACAGATATAGTTACAGTCACAGGTCTTAAAG

GTTCCTACCAGTTAAGTAGTTTTCTGAACGGCCAGAAGACCATTCGAAATTCATGATACT
5281   ------------+---------+---------+---------+---------+---------+   5340
       CAAGGATGGTCAATTCATCAAAAGACTTGCCGGTCTTCTGGTAAGCTTTAAGTACTATGA

ACTATAAGTTGGTAAACAACCATACTTTTATCCTCATTTTTATTCTCACTAAGAAAAAAG
5341   ------------+---------+---------+---------+---------+---------+   5400
       TGATATTCAACCATTTGTTGGTATGAAAATAGGAGTAAAAATAAGAGTGATTCTTTTTTC
```

Fig. 6H

```
       TCAACTCCCCTCCCCTTGCCCAAGTATGAAATATAGGGACAGTATGTATGGTGTGGTCTC
5401   ------+--------+--------+--------+--------+--------+        5460
       AGTTGAGGGGAGGGGAACGGGTTCATACTTTATATCCCTGTCATACATACCACACCAGAG

ATTTGTTTAGAAAACCACTTATGACTGGGTGCGGTGGCTCACACCTGTAATCCCAGCACT
5461   ------+--------+--------+--------+--------+--------+        5520
       TAAACAAATCTTTTGGTGAATACTGACCCACGCCACCGAGTGTGGACATTAGGGTCGTGA

TTGGGAGGCTGAGGCGGGCGAATCATTTGAGGTGAGGAATTCGAGACCAGCCTGGCCAGC
5521   ------+--------+--------+--------+--------+--------+        5580
       AACCCTCCGACTCCGCCCGCTTAGTAAACTCCACTCCTTAAGCTCTGGTCGGACCGGTCG

ATGGTGAAACCCCATCTCTACTAAAAATACAAAAATTAGCCAGGTGTGGTGGCACATGCC
5581   ------+--------+--------+--------+--------+--------+        5640
       TACCACTTTGGGGTAGAGATGATTTTTATGTTTTTAATCGGTCCACACCACCGTGTACGG

TGTAGTCCCAGCCACTAGGGCGGCTGAGACGCAAGACTTGCTTGAACCCGGGAGGCAGAG
5641   ------+--------+--------+--------+--------+--------+        5700
       ACATCAGGGTCGGTGATCCCGCCGACTCTGCGTTCTGAACGAACTTGGGCCCTCCGTCTC

GTTGCAGTGAGCCAAGATGGCGCCACTGCATTCCAGCCTGGGCAACAGAGCAAGACCCTG
5701   ------+--------+--------+--------+--------+--------+        5760
       CAACGTCACTCGGTTCTACCGCGGTGACGTAAGGTCGGACCCGTTGTCTCGTTCTGGGAC

TCTGTCTCAAAACAAAAAACAAAACCACTTATATTGCTAGCTACATTAAGAATTTCTGAA
5761   ------+--------+--------+--------+--------+--------+        5820
       AGACAGAGTTTTGTTTTTTGTTTTGGTGAATATAACGATCGATGTAATTCTTAAAGACTT

TATGTTACTGAGCTTGCTTGTGGTAACCATTTATAATATCAGAAAGTATATGTACACCAA
5821   ------+--------+--------+--------+--------+--------+        5880
       ATACAATGACTCGAACGAACACCATTGGTAAATATTATAGTCTTTCATATACATGTGGTT

AACATGTTGAACATCCATGTTGTACAACTGAAATATAAATAATTTTGTCAATTATACCTA
5881   ------+--------+--------+--------+--------+--------+        5940
       TTGTACAACTTGTAGGTACAACATGTTGACTTTATATTTATTAAAACAGTTAATATGGAT

AATAAAACTGGAAAAAAATTTCTGGAAGTTTATATCTAAAAATGTTAATAGTGCGTACCT
5941   ------+--------+--------+--------+--------+--------+        6000
       TTATTTTGACCTTTTTTTAAAGACCTTCAAATATAGATTTTACAATTATCACGCATGGA

CTAGGAAGTGGGCCTGGAAGCCATTCTTACTTTTCAGTCTCTCCCATTCTGTACTGTTTT
6001   ------+--------+--------+--------+--------+--------+        6060
       GATCCTTCACCCGGACCTTCGGTAAGAATGAAAAGTCAGAGAGGGTAAGACATGACAAAA

TTGTTTTACTTTCGTGCCTGCATTATTTTTCTATTTAAAACAAAAATAAATCTAGTTTAG
6061   ------+--------+--------+--------+--------+--------+        6120
       AACAAAATGAAAGCACGGACGTAATAAAAAGATAAATTTTGTTTTATTTAGATCAAATC

CACT
6121   ----    6124
       GTGA
```

Fig. 6I

SEQ ID NO: 23  TTCCGGCTGGACGTTGCCCTGTGTACCTCTTCGACTGCCTGTTCATCTACGACGAACCCC
1              ------------+---------+---------+---------+---------+--------- 60
               AAGGCCGACCTGCAACGGGACACATGGAGAAGCTGACGGACAAGTAGATGCTGCTTGGGG c
                                                          1  2
               GGGTATTGACCCCAGACAACAATGCCACTTCATATTGCATGAAGACAAAAGGTCCTGTGC
61             ------------+---------+---------+---------+---------+--------- 120
               CCCATAACTGGGGTCTGTTGTTACGGTGAAGTATAACGTACTTCTGTTTTCCAGGACACG c
                                             ↓              ↓       2  3
               TCACCTGGGACCCTTCTGGACGTTGCCCTGTACCTCTTCGACTGCCTGTTCATCTACG
121            ------------+---------+---------+---------+---------+--------- 180
               AGTGGACCCTGGGAAGACCTGCAACGGGACACATGGAGAAGCTGACGGACAAGTAGATGC c
               ACGAACCCCGGGTATTGACCCCAGACAACAATGCCACTTCATATTGGGGACTTCGTCTGG
181            ------------+---------+---------+---------+---------+--------- 240
               TGCTTGGGGCCCATAACTGGGGTCTGTTGTTACGGTGAAGTATAACCCCTGAAGCAGACC c
                                        3  4
               GATTCCAAGGTGCATTCATTGCAAAGTTCCTTAAATATTTTCTCACTGCTTCCTACTAAA
241            ------------+---------+---------+---------+---------+--------- 300
               CTAAGGTTCCACGTAAGTAACGTTTCAAGGAATTTATAAAAGAGTGACGAAGGATGATTT c
               GGACGGACAGAGCATTTGTTCTTCAGCCACATACTTTCCTTCCACTGGCCAGCATTCTCC
301            ------------+---------+---------+---------+---------+--------- 360
               CCTGCCTGTCTCGTAAACAAGAAGTCGGTGTATGAAAGGAAGGTGACCGGTCGTAAGAGG c
                                           4  5
               TCTATTAGACTAGAACTGTGGATAAACCTCAGAAAATGGCCACCCAGCAGAAAGCCTCTG
361            ------------+---------+---------+---------+---------+--------- 420
               AGATAATCTGATCTTGACACCTATTTGGAGTCTTTTACCGGTGGGTCGTCTTTCGGAGAC c                             SEQ ID NO:24  M  A  T  Q  Q  K  A  S  D -
               ACGAGAGGATCTCCCAGTTTGATCACAATTTGCTGCCAGAGCTGTCTGCTCTTCTGGGCC
421            ------------+---------+---------+---------+---------+--------- 480
               TGCTCTCCTAGAGGGTCAAACTAGTGTTAAACGACGGTCTCGACAGACGAGAAGACCCGG c              E  R  I  S  Q  F  D  H  N  L  L  P  E  L  S  A  L  L  G  L -
               TAGATGCAGTTCAGTTGGCAAAGGAACTAGAAGAAGAGGAGCAGAAGGAGCGAGCAAAAA
481            ------------+---------+---------+---------+---------+--------- 540
               ATCTACGTCAAGTCAACCGTTTCCTTGATCTTCTTCTCCTCGTCTTCCTCGCTCGTTTTT c              D  A  V  Q  L  A  K  E  L  E  E  E  E  Q  K  E  R  A  K  M -

Fig. 7A

```
                   TGCAGAAAGGCTACAACTCTCAAATGCGCAGTGAAGCAAAAAGGTTAAAGACTTTTGTGA
        541        ---------+---------+---------+---------+---------+---------+ 600
                   ACGTCTTTCCGATGTTGAGAGTTTACGCGTCACTTCGTTTTTCCAATTTCTGAAAACACT c         Q  K  G  Y  N  S  Q  M  R  S  E  A  K  R  L  K  T  F  V  T  -
                                                        NOT I
                   CTTATGAGCCGTACAGCTCATGGATACCACAGGAGATGCGGCCGCTGGGTTTTACTTCA
        601        ---------+---------+---------+---------+---------+---------+ 660
                   GAATACTCGGCATGTCGAGTACCTATGGTGTCCTCTACGCCGGCGACCCAAAATGAAGT c         Y  E  P  Y  S  S  W  I  P  Q  E  M  A  A  A  G  F  Y  F  T  -
                   CTGGGGTAAAATCTGGGATTCAGTGCTTCTGCTGTAGCCTAATCCTCTTTGGTGCCGGCC
        661        ---------+---------+---------+---------+---------+---------+ 720
                   GACCCCATTTTAGACCCTAAGTCACGAAGACGACATCGGATTAGGAGAAACCACGGCCGG c         G  V  K  S  G  I  Q  C  F  C  C  S  L  I  L  F  G  A  G  L  -
                   TCACGAGACTCCCCATAGAAGACCACAAGAGGTTTCATCCAGATTGTGGGTTCCTTTTGA
        721        ---------+---------+---------+---------+---------+---------+ 780
                   AGTGCTCTGAGGGGTATCTTCTGGTGTTCTCCAAAGTAGGTCTAACACCCAAGGAAAACT c         T  R  L  P  I  E  D  H  K  R  F  H  P  D  C  G  F  L  L  N  -
                   ACAAGGATGTTGGTAACATTGCCAAGTACGACATAAGGGTGAAGAATCTGAAGAGCAGGC
        781        ---------+---------+---------+---------+---------+---------+ 840
                   TGTTCCTACAACCATTGTAACGGTTCATGCTGTATTCCCACTTCTTAGACTTCTCGTCCG c         K  D  V  G  N  I  A  K  Y  D  I  R  V  K  N  L  K  S  R  L  -
                   TGAGAGGAGGTAAAATGAGGTACCAAGAAGAGGAGGCTAGACTTGCGTCCTTCAGGAACT
        841        ---------+---------+---------+---------+---------+---------+ 900
                   ACTCTCCTCCATTTTACTCCATGGTTCTTCTCCTCCGATCTGAACGCAGGAAGTCCTTGA c         R  G  G  K  M  R  Y  Q  E  E  E  A  R  L  A  S  F  R  N  W  -
                                   EcoRI
                   GGCCATTTTATGTCCAAGGGATATCCCCTTGTGTGCTCTCAGAGGCTGGCTTTGTCTTTA
        901        ---------+---------+---------+---------+---------+---------+ 960
                   CCGGTAAAATACAGGTTCCCTATAGGGGAACACACGAGAGTCTCCGACCGAAACAGAAAT c         P  F  Y  V  Q  G  I  S  P  C  V  L  S  E  A  G  F  V  F  T  -
                    5  6
                   CAGGTAAACAGGACACGGTACAGTGTTTTTCCTGTGGTGGATGTTTAGGAAATTGGGAAG
        961        ---------+---------+---------+---------+---------+---------+ 1020
                   GTCCATTTGTCCTGTGCCATGTCACAAAAAGGACACCACCTACAAATCCTTTAACCCTTC c         G  K  Q  D  T  V  Q  C  F  S  C  G  G  C  L  G  N  W  E  E  -
                                                         6  7
                   AAGGAGATGATCCTTGGAAGGAACATGCCAAATGGTTCCCCAATGTGAATTTCTTCGGA
        1021       ---------+---------+---------+---------+---------+---------+ 1080
                   TTCCTCTACTAGGAACCTTCCTTGTACGGTTTACCAAGGGGTTACACTTAAAGAAGCCT c         G  D  D  P  W  K  E  H  A  K  W  F  P  K  C  E  F  L  R  S  -
                   GTAAGAAATCCTCAGAGGAAATTACCCAGTATATTCAAAGCTACAAGGGATTTGTTGACA
        1081       ---------+---------+---------+---------+---------+---------+ 1140
                   CATTCTTTAGGAGTCTCCTTTAATGGGTCATATAAGTTTCGATGTTCCCTAAACAACTGT
```

Fig. 7B

```
c        K  K  S  S  E  E  I  T  Q  Y  I  Q  S  Y  K  G  F  V  D  I -
            7  8              EcoRI                              8  9
         TAACGGGAGAACATTTTGTGAATTCCTGGGTCCAGAGAGAATTACCTATGGCATCAGCTT
  1141   ------+---------+---------+---------+---------+---------+   1200
         ATTGCCCTCTTGTAAAACACTTAAGGACCCAGGTCTCTCTTAATGGATACCGTAGTCGAA c           T  G  E  H  F  V  N  S  W  V  Q  R  E  L  P  M  A  S  A  Y -

ATTGCAATGACAGCATCTTTGCTTACGAAGAACTACGGCTGGACTCTTTTAAGGACTGGC
  1201   ---------+---------+---------+---------+---------+---------+   1260
         TAACGTTACTGTCGTAGAAACGAATGCTTCTTGATGCCGACCTGAGAAAATTCCTGACCG c           C  N  D  S  I  F  A  Y  E  E  L  R  L  D  S  F  K  D  W  P -
                                                              9  10
         CCCGGGAATCAGCTGTGGGAGTTGCAGCACTGGCCAAAGCAGGTCTTTTCTACACAGGTA
  1261   ---------+---------+---------+---------+---------+---------+   1320
         GGGCCCTTAGTCGACACCCTCAACGTCGTGACCGGTTTCGTCCAGAAAAGATGTGTCCAT c           R  E  S  A  V  G  V  A  A  L  A  K  A  G  L  F  Y  T  G  I -

TAAAGGACATCGTCCAGTGCTTTTCCTGTGGAGGGTGTTTAGAGAAATGGCAGGAAGGTG
  1321   ---------+---------+---------+---------+---------+---------+   1380
         ATTTCCTGTAGCAGGTCACGAAAAGGACACCTCCCACAAATCTCTTTACCGTCCTTCCAC c           K  D  I  V  Q  C  F  S  C  G  G  C  L  E  K  W  Q  E  G  D -
                                        10 11
         ATGACCCATTAGACGATCACACCAGATGTTTTCCCAATTGTCCATTTCTCCAAAATATGA
  1381   ---------+---------+---------+---------+---------+---------+   1440
         TACTGGGTAATCTGCTAGTGTGGTCTACAAAAGGGTTAACAGGTAAAGAGGTTTTATACT c           D  P  L  D  D  H  T  R  C  F  P  N  C  P  F  L  Q  N  M  K -
                                                              11 12
         AGTCCTCTGCGGAAGTGACTCCAGACCTTCAGAGCCGTGGTGAACTTTGTGAATTACTGG
  1441   ---------+---------+---------+---------+---------+---------+   1500
         TCAGGAGACGCCTTCACTGAGGTCTGGAAGTCTCGGCACCACTTGAAACACTTAATGACC c           S  S  A  E  V  T  P  D  L  Q  S  R  G  E  L  C  E  L  L  E -
                                                           12 13
         AAACCACAAGTGAAAGCAATCTTGAAGATTCAATAGCAGTTGGTCCTATAGTGCCAGAAA
  1501   ---------+---------+---------+---------+---------+---------+   1560
         TTTGGTGTTCACTTTCGTTAGAACTTCTAAGTTATCGTCAACCAGGATATCACGGTCTTT c           T  T  S  E  S  N  L  E  D  S  I  A  V  G  P  I  V  P  E  M -

TGGCACAGGGTGAAGCCCAGTGGTTTCAAGAGGCAAAGAATCTGAATGAGCAGCTGAGAG
  1561   ---------+---------+---------+---------+---------+---------+   1620
         ACCGTGTCCCACTTCGGGTCACCAAAGTTCTCCGTTTCTTAGACTTACTCGTCGACTCTC c           A  Q  G  E  A  Q  W  F  Q  E  A  K  N  L  N  E  Q  L  R  A -
                                                       EcoRV
         CAGCTTATACCAGCGCCAGTTTCCGCCACATGTCTTTGCTTGATATCTCTTCCGATCTGG
  1621   ---------+---------+---------+---------+---------+---------+   1680
         GTCGAATATGGTCGCGGTCAAAGGCGGTGTACAGAAACGAACTATAGAGAAGGCTAGACC c           A  Y  T  S  A  S  F  R  H  M  S  L  L  D  I  S  S  D  L  A -
```

Fig. 7C

```
                CCACGGACCACTTGCTGGGCTGTGATCTGTCTATTGCTTCAAAACACATCAGCAAACCTG
     1681       ---------+---------+---------+---------+---------+---------+   1740
                GGTGCCTGGTGAACGACCCGACACTAGACAGATAACGAAGTTTTGTGTAGTCGTTTGGAC c        T  D  H  L  L  G  C  D  L  S  I  A  S  K  H  I  S  K  P  V -
                                    BSu36I
                TGCAAGAACCTCTGGTGCTGCCTGAGGTCTTTGGCAACTTGAACTCTGTCATGTGTGTGG
     1741       ---------+---------+---------+---------+---------+---------+   1800
                ACGTTCTTGGAGACCACGACGGACTCCAGAAACCGTTGAACTTGAGACAGTACACACACC c        Q  E  P  L  V  L  P  E  V  F  G  N  L  N  S  V  M  C  V  E -
                AGGGTGAAGCTGGAAGTGGAAAGACGGTCCTCCTGAAGAAAATAGCTTTTCTGTGGGCAT
     1801       ---------+---------+---------+---------+---------+---------+   1860
                TCCCACTTCGACCTTCACCTTTCTGCCAGGAGGACTTCTTTTATCGAAAAGACACCCGTA c        G  E  A  G  S  G  K  T  V  L  L  K  K  I  A  F  L  W  A  S -
                CTGGATGCTGTCCCCTGTTAAACAGGTTCCAGCTGGTTTTCTACCTCTCCCTTAGTTCCA
     1861       ---------+---------+---------+---------+---------+---------+   1920
                GACCTACGACAGGGGACAATTTGTCCAAGGTCGACCAAAAGATGGAGAGGGAATCAAGGT c        G  C  C  P  L  L  N  R  F  Q  L  V  F  Y  L  S  L  S  S  T -
                CCAGACCAGACGAGGGGCTGGCCAGTATCATCTGTGACCAGCTCCTAGAGAAAGAAGGAT
     1921       ---------+---------+---------+---------+---------+---------+   1980
                GGTCTGGTCTGCTCCCCGACCGGTCATAGTAGACACTGGTCGAGGATCTCTTTCTTCCTA c        R  P  D  E  G  L  A  S  I  I  C  D  Q  L  L  E  K  E  G  S -
                CTGTTACTGAAATGTGCATGAGGAACATTATCCAGCAGTTAAAGAATCAGGTCTTATTCC
     1981       ---------+---------+---------+---------+---------+---------+   2040
                GACAATGACTTTACACGTACTCCTTGTAATAGGTCGTCAATTTCTTAGTCCAGAATAAGG c        V  T  E  M  C  M  R  N  I  I  Q  Q  L  K  N  Q  V  L  F  L -
                TTTTAGATGACTACAAAGAAATATGTTCAATCCCTCAAGTCATAGGAAAACTGATTCAAA
     2041       ---------+---------+---------+---------+---------+---------+   2100
                AAAATCTACTGATGTTTCTTTATACAAGTTAGGGAGTTCAGTATCCTTTTGACTAAGTTT c        L  D  D  Y  K  E  I  C  S  I  P  Q  V  I  G  K  L  I  Q  K -
                AAAACCACTTATCCCGGACCTGCCTATTGATTGCTGTCCGTACAAACAGGGCCAGGGACA
     2101       ---------+---------+---------+---------+---------+---------+   2160
                TTTTGGTGAATAGGGCCTGGACGGATAACTAACGACAGGCATGTTTGTCCCGGTCCCTGT c        N  H  L  S  R  T  C  L  L  I  A  V  R  T  N  R  A  R  D  I -
                TCCGCCGATACCTAGAGACCATTCTAGAGATCAAAGCATTTCCCTTTTATAATACTGTCT
     2161       ---------+---------+---------+---------+---------+---------+   2220
                AGGCGGCTATGGATCTCTGGTAAGATCTCTAGTTTCGTAAAGGGAAAATATTATGACAGA c        R  R  Y  L  E  T  I  L  E  I  Q  A  F  P  F  Y  N  T  V  C -
                GTATATTACGGAAGCTCTTTTCACATAATATGACTCGTCTGCGAAAGTTTATGGTTTACT
```

Fig. 7D

```
      2221 ---------+---------+---------+---------+---------+---------+ 2280
           CATATAATGCCTTCGAGAAAAGTGTATTATACTGAGCAGACGCTTTCAAATACCAAATGA c          I   L   R   K   L   F   S   H   N   M   T   R   L   R   K   F   M   V   Y   F -

TTGGAAAGAACCAAAGTTTGCAGAAGATACAGAAAACTCCTCTCTTTGTGGCGGCGATCT
      2281 ---------+---------+---------+---------+---------+---------+ 2340
           AACCTTTCTTGGTTTCAAACGTCTTCTATGTCTTTTGAGGAGAGAAACACCGCCGCTAGA c          G   K   N   Q   S   L   Q   K   I   Q   K   T   P   L   F   V   A   A   I   C -

GTGCTCATTGGTTTCAGTATCCTTTTGACCCATCCTTTGATGATGTGGCTGTTTTCAAGT
      2341 ---------+---------+---------+---------+---------+---------+ 2400
           CACGAGTAACCAAAGTCATAGGAAAACTGGGTAGGAAACTACTACACCGACAAAAGTTCA c          A   H   W   F   Q   Y   P   F   D   P   S   F   D   D   V   A   V   F   K   S -

CCTATATGGAACGCCTTTCCTTAAGGAACAAAGCGACAGCTGAAATTCTCAAAGCAACTG
      2401 ---------+---------+---------+---------+---------+---------+ 2460
           GGATATACCTTGCGGAAAGGAATTCCTTGTTTCGCTGTCGACTTTAAGAGTTTCGTTGAC c          Y   M   E   R   L   S   L   R   N   K   A   T   A   E   I   L   K   A   T   V -

TGTCCTCCTGTGGTGAGCTGGCCTTGAAAGGGTTTTTTTCATGTTGCTTTGAGTTTAATG
      2461 ---------+---------+---------+---------+---------+---------+ 2520
           ACAGGAGGACACCACTCGACCGGAACTTTCCCAAAAAAAGTACAACGAAACTCAAATTAC c          S   S   C   G   E   L   A   L   K   G   F   F   S   C   C   F   E   F   N   D -

ATGATGATCTCGCAGAAGCAGGGGTTGATGAAGATGAAGATCTAACCATGTGCTTGATGA
      2521 ---------+---------+---------+---------+---------+---------+ 2580
           TACTACTAGAGCGTCTTCGTCCCCAACTACTTCTACTTCTAGATTGGTACACGAACTACT c          D   D   L   A   E   A   G   V   D   E   D   E   D   L   T   M   C   L   M   S -

GCAAATTTACAGCCCAGAGACTAAGACCATTCTACCGGTTTTTAAGTCCTGCCTTCCAAG
      2581 ---------+---------+---------+---------+---------+---------+ 2640
           CGTTTAAATGTCGGGTCTCTGATTCTGGTAAGATGGCCAAAAATTCAGGACGGAAGGTTC c          K   F   T   A   Q   R   L   R   P   F   Y   R   F   L   S   P   A   F   Q   E

AATTTCTTGCGGGGATGAGGCTGATTGAACTCCTGGATTCAGATAGGCAGGAACATCAAG
      2641 ---------+---------+---------+---------+---------+---------+ 2700
           TTAAAGAACGCCCCTACTCCGACTAACTTGAGGACCTAAGTCTATCCGTCCTTGTAGTTC c          F   L   A   G   M   R   L   I   E   L   L   D   S   D   R   Q   E   H   Q   D -

ATTTGGGACTGTATCATTTGAAACAAATCAACTCACCCATGATGACTGTAAGCGCCTACA
      2701 ---------+---------+---------+---------+---------+---------+ 2760
           TAAACCCTGACATAGTAAACTTTGTTTAGTTGAGTGGGTACTACTGACATTCGCGGATGT c          L   G   L   Y   H   L   K   Q   I   N   S   P   M   M   T   V   S   A   Y   N -

ACAATTTTTTGAACTATGTCTCCAGCCTCCCTTCAACAAAAGCAGGGCCCAAAATTGTGT
      2761 ---------+---------+---------+---------+---------+---------+ 2820
```

Fig. 7E

```
                TGTTAAAAAACTTGATACAGAGGTCGGAGGGAAGTTGTTTTCGTCCCGGGTTTTAACACA c       N  F  L  N  Y  V  S  S  L  P  S  T  K  A  G  P  K  I  V  S -

CTCATTTGCTCCATTTAGTGGATAACAAAGAGTCATTGGAGAATATATCTGAAAATGATG
    2821    ---------+---------+---------+---------+---------+---------+  2880
            GAGTAAACGAGGTAAATCACCTATTGTTTCTCAGTAACCTCTTATATAGACTTTTACTAC c       H  L  L  H  L  V  D  N  K  S  S  L  E  N  I  S  E  N  D  D -
                                              PstI
            ACTACTTAAAGCACCAGCCAGAAATTTCACTGCAGATGCAGTTACTTAGGGGATTGTGGC
    2881    ---------+---------+---------+---------+---------+---------+  2940
            TGATGAATTTCGTGGTCGGTCTTTAAAGTGACGTCTACGTCAATGAATCCCCTAACACCG c       Y  L  K  H  Q  P  E  I  S  L  Q  M  Q  L  L  R  G  L  W  Q -
                          HindIII
            AAATTTGTCCACAAGCTTACTTTTCAATGGTTTCAGAACATTTACTGGTTCTTGCCCTGA
    2941    ---------+---------+---------+---------+---------+---------+  3000
            TTTAAACAGGTGTTCGAATGAAAAGTTACCAAAGTCTTGTAAATGACCAAGAACGGGACT c       I  C  P  Q  A  Y  F  S  M  V  S  E  H  L  L  V  A  L  K -

AAACTGCTTATCAAAGCAACACTGTTGCTGCGTGTTCTCCATTTGTTTTGCAATTCCTTC
    3001    ---------+---------+---------+---------+---------+---------+  3060
            TTTGACGAATAGTTTCGTTGTGACAACGACGCACAAGAGGTAAACAAAACGTTAAGGAAG c       T  A  Y  Q  S  N  T  V  A  A  C  S  P  F  V  L  Q  F  L  Q -

AAGGGAGAACACTGACTTTGGGTGCGCTTAACTTACAGTACTTTTTCGACCACCCAGAAA
    3061    ---------+---------+---------+---------+---------+---------+  3120
            TTCCCTCTTGTGACTGAAACCCACGCGAATTGAATGTCATGAAAAAGCTGGTGGGTCTTT c          G  R  T  L  T  L  G  A  L  N  L  Q  Y  F  F  D  H  P  E  S -
            HindIII                           ↓
            GCTTGTCATTGTTGAGGAGCATCCACTTCCAATACGAGGAAATAAGACATCACCCAGAG
    3121    ---------+---------+---------+---------+---------+---------+  3180
            CGAACAGTAACAACTCCTCGTAGGTGAAGGTTATGCTCCTTTATTCTGTAGTGGGTCTC c       L  S  L  L  R  S  I  H  F  S  I  R  G  N  K  T  S  P  R  A -

CACATTTTTCAGTTCTGGAAACATGTTTTGACAAATCACAGGTGCCAACTATAGATCAGG
    3181    ---------+---------+---------+---------+---------+---------+  3240
            GTGTAAAAAGTCAAGACCTTTGTACAAAACTGTTTAGTGTCCACGGTTGATATCTAGTCC c       H  F  S  V  L  E  T  C  F  D  K  S  Q  V  P  T  I  D  Q  D -

ACTATGCTTCTGCCTTTGAACCTATGAATGAATGGGAGCGAAATTTAGCTGAAAAAGAGG
    3241    ---------+---------+---------+---------+---------+---------+  3300
            TGATACGAAGACGGAAACTTGGATACTTACTTACCCTCGCTTTAAATCGACTTTTTCTCC c       Y  A  S  A  F  E  P  M  N  E  W  E  R  N  L  A  E  K  E  D -

ATAATGTAAAGAGCTATATGGATATGCAGCGCAGGGCATCACCAGACCTTAGTACTGGCT
    3301    ---------+---------+---------+---------+---------+---------+  3360
            TATTACATTTCTCGATATACCTATACGTCGCGTCCCGTAGTGGTCTGGAATCATGACCGA
```

Fig. 7F

```
c        N  V  K  S  Y  M  D  M  Q  R  R  A  S  P  D  L  S  T  G  Y-
                                              XGaI
         ATTGGAAACTTTCTCCAAAGCAGTACAAGATTCCCTGTCTAGAAGTCGATGTGAATGATA
   3361  ---------+---------+---------+---------+---------+---------+  3420
         TAACCTTTGAAAGAGGTTTCGTCATGTTCTAAGGGACAGATCTTCAGCTACACTTACTAT c        W  K  L  S  P  K  Q  Y  K  I  P  C  L  E  V  D  V  N  D  I-
         TTGATGTTGTAGGCCAGGATATGCTTGAGATTCTAATGACAGTTTTCTCAGCTTCACAGC
   3421  ---------+---------+---------+---------+---------+---------+  3480
         AACTACAACATCCGGTCCTATACGAACTCTAAGATTACTGTCAAAAGAGTCGAAGTGTCG c        D  V  V  G  Q  D  M  L  E  I  L  M  T  V  F  S  A  S  Q  R-
         GCATCGAACTCCATTTAAACCACAGCAGAGGCTTTATAGAAAGCATCCGCC CAGCTCTTG
   3481  ---------+---------+---------+---------+---------+---------+  3540
         CGTAGCTTGAGGTAAATTTGGTGTCGTCTCCGAAATATCTTTCGTAGGCGGGTCGAGAAC c        I  E  L  H  L  N  H  S  R  G  F  I  E  S  I  R  P  A  L  E-
         AGCTGTCTAAGGCCTCTGTCACCAAGTGCTCCATAAGCAAGTTGGAACTCAGCGCAGCCG
   3541  ---------+---------+---------+---------+---------+---------+  3600
         TCGACAGATTCCGGAGACAGTGGTTCACGAGGTATTCGTTCAACCTTGAGTCGCGTCGGC c        L  S  K  A  S  V  T  K  C  S  I  S  K  L  E  L  S  A  A  E-
         AACAGGAACTGCTTCTCACCCTGCCTTCCCTGGAATCTCTTGAAGTCTCAGGGACAATCC
   3601  ---------+---------+---------+---------+---------+---------+  3660
         TTGTCCTTGACGAAGAGTGGGACGGAAGGGACCTTAGAGAACTTCAGAGTCCCTGTTAGG c        Q  E  L  L  T  L  P  S  L  E  S  L  E  V  S  G  T  I  Q-
            13  14
         AGTCACAAGACCAAATCTTTCCTAATCTGGATAAGTTCCTGTGCCTGAAAGAACTGTCTG
   3661  ---------+---------+---------+---------+---------+---------+  3720
         TCAGTGTTCTGGTTTAGAAAGGATTAGACCTATTCAAGGACACGGACTTTCTTGACAGAC c        S  Q  D  Q  I  F  P  N  L  D  K  F  L  C  L  K  E  L  S  V-
         BstYI
         TGGATCTGGAGGGCAATATAAATGTTTTTTCAGTCATTCCTGAAGAATTTCCAAACTTCC
   3721  ---------+---------+---------+---------+---------+---------+  3780
         ACCTAGACCTCCCGTTATATTTACAAAAAAGTCAGTAAGGACTTCTTAAAGGTTTGAAGG c        D  L  E  G  N  I  N  V  F  S  V  I  P  E  E  F  P  N  F  H-
                                                          14  14A
         ACCATATGGAGAAATTATTGATCCAAATTTCAGCTGAGTATGATCCTTCCAAACTAGTAA
   3781  ---------+---------+---------+---------+---------+---------+  3840
         TGGTATACCTCTTTAATAACTAGGTTTAAAGTCGACTCATACTAGGAAGGTTTGATCATT c        H  M  E  K  L  L  I  Q  I  S  A  E  Y  D  P  S  K  L  V  K-
         AATTAATTCAAAATTCTCCAAACCTTCATGTTTTCCATCTGAAGTGTAACTTCTTTTCGG
   3841  ---------+---------+---------+---------+---------+---------+  3900
         TTAATTAAGTTTTAAGAGGTTTGGAAGTACAAAAGGTAGACTTCACATTGAAGAAAAGCC c        L  I  Q  N  S  P  N  L  H  V  F  H  L  K  C  N  F  F  S  D-
```

Fig. 7G

```
            ATTTTGGGTCTCTCATGACTATGCTTGTTTCCTGTAAGAAACTCACAGAAATTAAGTTTT
     3901   ------------+---------+---------+---------+---------+---------+ 3960
            TAAAACCCAGAGAGTACTGATACGAACAAAGGACATTCTTTGAGTGTCTTTAATTCAAAA c           L  G  S  L  M  T  M  L  V  S  C  K  K  L  T  E  I  K  F  S  -
                                      14A 15
            CGGATTCATTTTTTCAAGCCGTCCCATTTGTTGCCAGTTTGCCAAATTTTATTTCTCTGA
     3961   ---------+---------+---------+---------+---------+---------+ 4020
            GCCTAAGTAAAAAAGTTCGGCAGGGTAAACAACGGTCAAACGGTTTAAAATAAAGAGACT c           D  S  F  F  Q  A  V  P  F  V  A  S  L  P  N  F  I  S  L  K  -
                                                                  15 16
            AGATATTAAATCTTGAAGGCCAGCAATTTCCTGATGAGGAAACATCAGAAAAATTTGCCT
     4021   ---------+---------+---------+---------+---------+---------+ 4080
            TCTATAATTTAGAACTTCCGGTCGTTAAAGGACTACTCCTTTGTAGTCTTTTTAAACGGA c           I  L  N  L  E  G  Q  Q  F  P  D  E  E  T  S  E  K  F  A  Y  -

ACATTTTAGGTTCTCTTAGTAACCTGGAAGAATTGATCCTTCCTACTGGGGATGGAATTT
     4081   ---------+---------+---------+---------+---------+---------+ 4140
            TGTAAAATCCAAGAGAATCATTGGACCTTCTTAACTAGGAAGGATGACCCCTACCTTAAA c           I  L  G  S  L  S  N  L  E  E  L  I  L  P  T  G  D  G  I  Y  -

ATCGAGTGGCCAAACTGATCATCCAGCAGTGTCAGCAGCTTCATTGTCTCCGAGTCCTCT
     4141   ---------+---------+---------+---------+---------+---------+ 4200
            TAGCTCACCGGTTTGACTAGTAGGTCGTCACAGTCGTCGAAGTAACAGAGGCTCAGGAGA c           R  V  A  K  L  I  I  Q  Q  C  Q  Q  L  H  C  L  R  V  L  S  -
                                                  16 17
            CATTTTTCAAGACTTTGAATGATGACAGCGTGGTGGAAATTGCCAAAGTAGCAATCAGTG
     4201   ---------+---------+---------+---------+---------+---------+ 4260
            GTAAAAAGTTCTGAAACTTACTACTGTCGCACCACCTTTAACGGTTTCATCGTTAGTCAC c           F  F  K  T  L  N  D  D  S  V  V  E  I  A  K  V  A  I  S  G  -

GAGGTTTCCAGAAACTTGAGAACCTAAAGCTTTCAATCAATCACAAGATTACAGAGGAAG
     4261   ---------+---------+---------+---------+---------+---------+ 4320
            CTCCAAAGGTCTTTGAACTCTTGGATTTCGAAAGTTAGTTAGTGTTCTAATGTCTCCTTC c           G  F  Q  K  L  E  N  L  K  L  S  I  N  H  K  I  T  E  E  G  -

GATACAGAAATTTCTTTCAAGCACTGGACAACATGCCAAACTTGCAGGAGTTGGACATCT
     4321   ---------+---------+---------+---------+---------+---------+ 4380
            CTATGTCTTTAAAGARAGTTCGTGACCTGTTGTACGGTTTGAACGTCCTCAACCTGTAGA c           Y  R  N  F  F  Q  A  L  D  N  M  P  N  L  Q  E  L  D  I  S  -

CCAGGCATTTCACAGAGTGTATCAAAGCTCAGGCCACAACAGTCAAGTCTTTGAGTCAAT
     4381   ---------+---------+---------+---------+---------+---------+ 4440
            GGTCCGTAAAGTGTCTCACATAGTTTCGAGTCCGGTGTTGTCAGTTCAGAAACTCAGTTA c           R  H  F  T  E  C  I  K  A  Q  A  T  T  V  K  S  L  S  Q  C  -

GTGTGTTACGACTACCAAGGCTCATTAGACTGAACATGTTAAGTTGGCTCTTGGATGCAG
```

Fig. 7H

```
4441 ---------+---------+---------+---------+---------+---------+ 4500
     CACACAATGCTGATGGTTCCGAGTAATCTGACTTGTACAATTCAACCGAGAACCTACGTC
``` c     V  L  R  L  P  R  L  I  R  L  N  M  L  S  W  L  L  D  A  D -

```
     ATGATATTGCATTGCTTAATGTCATGAAAGAAAGACATCCTCAATCTAAGTACTTAACTA
4501 ---------+---------+---------+---------+---------+---------+ 4560
     TACTATAACGTAACGAATTACAGTACTTTCTTTCTGTAGGAGTTAGATTCATGAATTGAT
``` c     D  I  A  L  L  N  V  M  K  E  R  H  P  Q  S  K  Y  L  T  I -

```
     TTCTCCAGAAATGGATACTGCCGTTCTCTCCAATCATTCAGAAATAAAAGATTCAGCTAA
4561 ---------+---------+---------+---------+---------+---------+ 4620
     AAGAGGTCTTTACCTATGACGGCAAGAGAGGTTAGTAAGTCTTTATTTTCTAAGTCGATT
``` c     L  Q  K  W  I  L  P  F  S  P  I  I  Q  K  * -

```
     AAACTGCTGAATCAATAATTTGTCTTGGGGCATATTGAGGATGTAAAAAAAGTTGTTGAT
4621 ---------+---------+---------+---------+---------+---------+ 4680
     TTTGACGACTTAGTTATTAAACAGAACCCCGTATAACTCCTACATTTTTTCAACAACTA
``` c

```
     TAATGCTAAAAACAAATTATCCAAAATTATTTTATTAAATATTGCATACAAAAGAAAATG
4681 ---------+---------+---------+---------+---------+---------+ 4740
     ATTACGATTTTTGTTTAATAGGTTTTAATAAAATAATTTATAACGTATGTTTTCTTTTAC
``` c

```
     TGTAAGGCTTGCTAAAAAACAAAACAAAACAAAACACAGTCCTGCATACTCACCACCAAG
4741 ---------+---------+---------+---------+---------+---------+ 4800
     ACATTCCGAACGATTTTTTGTTTTGTTTTGTTTTGTGTCAGGACGTATGAGTGGTGGTTC
``` c

```
     GCTCAAGAAATAAATCATCACCAATACCTTTGAGGTCCCTGAGTAATCCACCCCAGCTAA
4801 ---------+---------+---------+---------+---------+---------+ 4860
     CGAGTTCTTTATTTAGTAGTGGTTATGGAAACTCCAGGGACTCATTAGGTGGGGTCGATT
``` c

```
     GGCAAACCCTTCAATCAAGTTTATACAGCARACCCTCCATTGTCCATGGTCAACAGGGAA
4861 ---------+---------+---------+---------+---------+---------+ 4920
     CCGTTTGGGAAGTTAGTTCAAATATGTCGTTTGGGAGGTAACAGGTACCAGTTGTCCCTT
``` c

```
     GGGGTTGGGGACAGGTCTGCCAATCTATCTAAAAGCCACAATATGGAAGAATATTCAATT
4921 ---------+---------+---------+---------+---------+---------+ 4980
     CCCCAACCCCTGTCCAGACGGTTAGATAGATTTTCGGTGTTATACCTTCTTATAAGTTAA
``` c

```
     TATATAATAAATGGCTAACTTAACGGTTGAATCACTTTCATACATGGATGAAACGGGTTT
4981 ---------+---------+---------+---------+---------+---------+ 5040
     ATATATTATTTACCGATTGAATTGCCAACTTAGTGAAAGTATGTACCTACTTTGCCCAAA
```

Fig. 7I

```
                    BamHI
       AACACA GGATCC ACATGAATCTTCTGTGGGCCAAGAGATGTTCCTTAATCCTTGTAGAAC
c 5041 ------|------|-------+---------+---------+---------+---------+ 5100
       TTGTGT CCTAGG TGTACTTAGAAGACACCCGGTTCTCTACAAGGAATTAGGAACATCTTG

CTGTTTTCTATATTGAACTAGCTTTGGTACAGTAGAGTTAACTTACTTTCCATTTATCCA
c 5101 ---------+---------+---------+---------+---------+---------+ 5160
       GACAAAAGATATAACTTGATCGAAACCATGTCATCTCAATTGAATGAAAGGTAAATAGGT

CTGCCAATATAAAGAGGAAACAGGGGTTAGGGAAAAATGACTTCATTCCAGAGGCTTCTC
c 5161 ---------+---------+---------+---------+---------+---------+ 5220
       GACGGTTATATTTCTCCTTTGTCCCCAATCCCTTTTTACTGAAGTAAGGTCTCCGAAGAG

AGAGTTCAACATATGCTATAATTTAGAATTTTCTTATGAATCCACTCTACTTGGGTAGAA
c 5221 ---------+---------+---------+---------+---------+---------+ 5280
       TCTCAAGTTGTATACGATATTAAATCTTAAAAGAATACTTAGGTGAGATGAACCCATCTT

AATATTTTATCTCTAGTGATTGCATATTATTTCCATATCATAGTATTTCATAGTATTATA
c 5281 ---------+---------+---------+---------+---------+---------+ 5340
       TTATAAAATAGAGATCACTAACGTATAATAAAGGTATAGTATCATAAAGTATCATAATAT

TTTGATATGAGTGTCTATATCAATGTCAGTGTCCAGAATTTCGTTCCTACCAGTTAAGTA
c 5341 ---------+---------+---------+---------+---------+---------+ 5400
       AAACTATACTCACAGATATAGTTACAGTCACAGGTCTTAAAGCAAGGATGGTCAATTCAT

GTTTTCTGAACGGCCAGAAGACCATTCGAAATTCATGATACTACTATAAGTTGGTAAACA
c 5401 ---------+---------+---------+---------+---------+---------+ 5460
       CAAAAGACTTGCCGGTCTTCTGGTAAGCTTTAAGTACTATGATGATATTCAACCATTTGT

ACCATACTTTTATCCTCATTTTTATTCTCACTAAGAAAAAAGTCAACTCCCCTCCCCTTG
c 5461 ---------+---------+---------+---------+---------+---------+ 5520
       TGGTATGAAAATAGGAGTAAAAATAAGAGTGATTCTTTTTTCAGTTGAGGGGAGGGGAAC

CCCAAGTATGAAATATAGGGACAGTATGTATGGTGTGGTCTCATTTGTTTAAAAAACCAC
c 5521 ---------+---------+---------+---------+---------+---------+ 5580
       GGGTTCATACTTTATATCCCTGTCATACATACCACACCAGAGTAAACAAATTTTTTGGTG
```

Fig. 7J

```
c
         TTATGACTGGGTGCGGTGGCTCACACCTGTAATCCCACCACTTTGGGAGGCTGAGGCGGG
    5581 ---------+---------+---------+---------+---------+---------+ 5640
         AATACTGACCCACGCCACCGAGTGTGGACATTAGGGTGGTGAAACCCTCCGACTCCGCCC c
                         EcoRI
         CGAATCATTTGAGGTGAGGAATTCGAGACCAGCCTGGCCAGCATGGTGAAACCCCATCTC
    5641 ---------+-------+-+-----+---------+---------+---------+ 5700
         GCTTAGTAAACTCCACTCCTTAAGCTCTGGTCGGACCGGTCGTACCACTTTGGGGTAGAG
c
         TACTAAAAATACAAAAATTAGCCAGGTGTGGTGGCACATGCCTGTAAGTCCCAGCCACTA
    5701 ---------+---------+---------+---------+---------+---------+ 5760
         ATGATTTTTATGTTTTTAATCGGTCCACACCACCGTGTACGGACATTCAGGGTCGGTGAT c
         GGGCGGCTGAGACGCAAGACTTGCTTGAACCCGGGAGGCAGAGGTTGCAGTGAGCCAAGA
    5761 ---------+---------+---------+-SmaI-+---------+---------+ 5820
         CCCGCCGACTCTGCGTTCTGAACGAACTTGGGCCCTCCGTCTCCAACGTCACTCGGTTCT

TGGCGCCACTGCATTCCAGCCTGGGCAACAGAGCAAGACCCTGTCTGTCTCAAAACAAAA
    5821 ---------+---------+---------+---------+---------+---------+ 5880
         ACCGCGGTGACGTAAGGTCGGACCCGTTGTCTCGTTCTGGGACAGACAGAGTTTTGTTTT c
         AACAAAACCACTTATATTGCTAGCTACATTAAGAATTTCTGAATATGTTACTGAGCTTGC
    5881 ---------+---------+---------+---------+---------+---------+ 5940
         TTGTTTTGGTGAATATAACGATCGATGTAATTCTTAAAGACTTATACAATGACTCGAACG c
         TTGTGGTAACCATTTATAATATCAGAAAGTATATGTACACCAAAACATGTTGAACATCCA
    5941 ---------+---------+---------+---------+---------+---------+ 6000
         AACACCATTGGTAAATATTATAGTCTTTCATATACATGTGGTTTTGTACAACTTGTAGGT c
         TGTTGTACAACTTGAAATATAAATAATTTTGTCAATTATACCTAAATAAAACTGGAAAAA
    6001 ---------+---------+---------+---------+---------+---------+ 6060
         ACAACATGTTGAACTTTATATTTATTAAAACAGTTAATATGGATTTATTTTGACCTTTTT c
         AATTTCTGGAAGTTTATATCTAAAAATGTTAATAGTGCGTACCTCTAGGAAGTGGGCCTG
    6061 ---------+---------+---------+---------+---------+---------+ 6120
         TTAAAGACCTTCAAATATAGATTTTTACAATTATCACGCATGGAGATCCTTCACCCGGAC
```

Fig. 7K c
```
     GAAGCCATTCTTACTTTTCAGTCTCTCCCATTCTGTACTGTTTTTTGTTTTACTTTCGTG
6121 ---------+---------+---------+---------+---------+---------+ 6180
     CTTCGGTAAGAATGAAAAGTCAGAGAGGGTAAGACATGACAAAAAACAAAATGAAAGCAC
```
c
```
     CCTGCATTATTTTTCTATTTAAAACAAAAATAAATCTAGTTTAGCACT poly A tail
6181 ---------+---------+---------+---------+-------- 6228
```

Fig. 7L

USE OF NEURONAL APOPTOSIS INHIBITOR PROTEIN (NAIP)

CROSS REFERENCE TO RELATED APPLICATIONS

This application is a continuation of U.S. Ser. No. 08/913,322, now U.S. Pat. No. 6,994,957, filed Sep. 12, 1997, which claims priority under 35 U.S.C. § 371 to PCT/IB97/00142, filed Jan. 17, 1997, which claims priority to GB 9601108.5, filed on Jan. 19, 1996, each of which is incorporated by reference.

FIELD OF THE INVENTION

This invention relates in general to the function of the NAIP inhibitor protein in apoptosis and more particularly to the use of NAIP antibodies, proteins, and nucleic acids to characterize NAIP, identify compounds that modulate NAIP, and diagnose and treat conditions affected by changes in NAIP levels.

BACKGROUND OF THE INVENTION

Apoptosis is a morphologically distinct form of programmed cell death that is important in the normal development and maintenance of multicellular organisms. Dysregulation of apoptosis can take the form of inappropriate suppression of cell death, as occurs in the development of some cancers, or in a failure to control the extent of cell death, as is believed to occur in acquired immunodeficiency and certain neurodegenerative disorders, such as spinal muscular atrophy (SMA).

Childhood spinal muscular atrophies are neurodegenerative disorders characterized by progressive spinal cord motor neuron depletion and are among the most common autosomal recessive disorders (Dubowitz, V. 1978, Brooke, M. A. 1986). Type I SMA is the most frequent inherited cause of death in infancy. The loss of motor neurons in SMA, has led to suggestions that an inappropriate continuation or reactivation of normally occurring motor neuron apoptosis may underlie the disorder (Sarnat, H. B. 1992). NAIP, a gene associated with SMA, has been mapped to human chromosome 5q13.1

Some baculoviruses encode proteins that are termed inhibitors of apoptosis proteins (IAPs) because they inhibit the apoptosis that would otherwise occur when insect cells are infected by the virus. These proteins are thought to work in a manner that is independent of other viral proteins. The baculovirus IAP genes include sequences encoding a ring zinc finger-like motif (RZF), which may be involved in DNA binding, and two N-terminal domains that consist of a 70 amino acid repeat motif termed a BIR domain (Baculovirus IAP Repeat).

SUMMARY OF THE INVENTION

We have discovered uses for NAIP proteins, nucleic acids, and antibodies for the detection and treatment of conditions involving apoptosis. Furthermore, we have discovered a novel NAIP sequence and a NAIP fragment with enhanced anti-apoptotic activities.

In general, the invention features a substantially pure nucleic acid molecule, such as a genomic, cDNA, antisense DNA, RNA, or a synthetic nucleic acid molecule, that encodes or corresponds to a mammalian NAIP polypeptide. This nucleic acid may be incorporated into a vector. Such a vector may be in a cell, such as a mammalian, yeast, nematode, or bacterial cell. The nucleic acid may also be incorporated into a transgenic animal or embryo thereof. In preferred embodiments, the nucleic acid molecule is a human NAIP nucleic acid. In most preferred embodiments the NAIP gene is a human NAIP gene. In other various preferred embodiments, the cell is a transformed cell.

According to one preferred embodiment, the nucleic acid sequence includes the cDNA sequences encoding exons 14a and 17. In a more preferred embodiment the sequence includes exons 1–14, 14a, and 15–17. In the most preferred embodiments the sequence also includes the complete 5' and 3' untranslated regions of the NAIP gene and is represented as SEQ ID NOs: 2, 21, or 23, most preferably, as in SEQ ID NO: 21. In other preferred embodiments, the nucleic acid is a purified nucleotide sequence comprising genomic DNA, cDNA, mRNA, anti-sense DNA or other DNA substantially identical to the cDNA sequences of SEQ ID NOs: 2, 21, or 23 corresponding to the cDNA sequences of the invention. Most preferably exons 1 to 14 and 14a to 17 are as described in SEQ ID NO: 21.

In specific embodiments, the invention features nucleic acid sequences substantially identical to the sequences shown in FIGS. 6A–I, or fragments thereof. In another aspect, the invention also features RNA which is encoded by the DNA described herein. Preferably, the RNA is mRNA. In another embodiment the RNA is antisense RNA that is complementing to the coding strand of NAIP.

In a second aspect of the invention, the NAIP encoding nucleic acid comprises at least the 3 BIR domains of a NAIP sequence provided herein (e.g., nucleotides 1–1360 of the NAIP sequence provided in FIGS. 6A–I), but lacks at least some of the sequences encoding the carboxy terminus of the NAIP polypeptide. Preferably, at least 30 nucleic acids are deleted from the region of the NAIP gene between nucleic acids 1360 (i.e., the end of the BIR domains) and 4607 (i.e., the end of the coding sequence) of the NAIP sequence shown in FIGS. 6A–I, SEQ ID NO: 21. More preferably, at least 100 nucleotides are deleted, and even more preferably at least 1000 nucleotides are deleted. In the most preferred embodiment, up to 3247 nucleotides are deleted. Preferably, the deletion results in a statistically significant increase in the anti-apoptotic activity of the encoded protein on one of the assays provided herein.

In a third aspect, the invention features a substantially pure DNA which includes a promoter capable of expressing or activating the expression of the NAIP gene or fragments thereof in a cell susceptible to apoptosis. In preferred embodiments of this aspect, the NAIP gene is human NAIP or fragments thereof, as described above. In further preferred embodiments of this aspect of the invention, the promoter is the promoter native to the NAIP gene. Additionally, transcriptional and translational regulatory regions are, preferably, those native to a NAIP gene.

In another aspect, the invention provides transgenic cell lines, including the NAIP nucleic acids of the invention. The transgenic cells of the invention are preferably cells that are altered in their apoptotic response. In preferred embodiments, the transgenic mammalian cell is a fibroblast, neuronal cell, a pulmonary cell, a renal cell, a lymphocyte cell, a glial cell, a myocardial cell, an embryonic stem cell, or an insect cell. Most preferably, the neuron is a motor neuron and the lymphocyte is a CD4$^+$ T cell.

In one preferred embodiment, the nucleic acid sequence includes the cDNA sequences (shown in FIGS. 6A–I) of SEQ ID NO: 21, encoding exon 14a, which corresponds to nucleic acids 3734–3886, and exon 17, which corresponds to nucleic acids 4139–4503. In another preferred embodiment, the nucleic acid sequence includes the sequence of SEQ ID NO: 23, encoding exon 14a, which corresponds to nucleic acids 3838–3990, and exon 17, which corresponds to nucleic acids 4243–4605.

In another related aspect, the invention features a method of altering the level of apoptosis that involves producing a transgenic cell having a transgene encoding a NAIP polypeptide or antisense nucleic acid. The transgene is integrated into the genome of the cell in a way that allows for expression. Furthermore, the level of expression in the cell is sufficient to alter the level of apoptosis. In preferred embodiments the transgene is in a motor neuron or a myocardial cell.

In yet another related aspect, the invention features a transgenic animal, preferably a mammal, more preferably a rodent, and most preferably a mouse, having a NAIP gene as described above inserted into the genome (mutant or wild-type), or a knockout of a NAIP gene in the genome, or both. A transgenic animal expressing NAIP antisense nucleic acid is also included. The transgenic animals may express either an increased or a decreased amount of NAIP polypeptide, depending on the construct used and the nature of the genomic alteration. For example, utilizing a nucleic acid molecule that encodes all or part of a NAIP to engineer a knockout mutation in a NAIP gene would generate an animal with decreased expression of either all or part of the corresponding NAIP polypeptide. In contrast, inserting exogenous copies of all or part of a NAIP gene into the genome, preferably under the control of active regulatory and promoter elements, would lead to increased expression or the corresponding NAIP polypeptide.

In another aspect, the invention features a method of detecting a NAIP gene in a cell by detecting the NAIP gene, or a portion thereof (which is greater than 9 nucleotides, and preferably greater than 18 nucleotides in length), with a preparation of genomic DNA from the cell. The NAIP gene and the genomic DNA are brought into contact under conditions that allow for hybridization (and therefore, detection) of nucleic acid sequences in the cell that are at least 50% identical to the DNA encoding the NAIP polypeptides. Preferably, the nucleic acid used comprised at least a part of exon 14a or exon 17, as provided in FIGS. 6A–I and 7A–L.

In another aspect, the invention features a method of producing a NAIP polypeptide in vivo or in vitro. In one embodiment, this method involves providing a cell with nucleic acid encoding all or part of a NAIP polypeptide (which is positioned for expression in the cell), culturing the cell under conditions that allow for expression of the nucleic acid, and isolating the NAIP polypeptide. In preferred embodiments, the NAIP polypeptide is expressed by DNA that is under the control of a constitutive or inducible promotor. As described herein, the promotor may be a native or heterologous promoter. In preferred embodiments the nucleic acid comprises exon 14a or exon 17. Most preferably the nucleic acid is the nucleic acid shown in either FIGS. 6A–I or FIGS. 7A–L. Most preferably, it is the sequence shown in FIGS. 6A–I.

In another aspect, the invention features substantially pure mammalian NAIP polypeptide. Preferably, the polypeptide includes an amino acid sequence that is substantially identical to one of the amino acid sequences shown in any one of FIGS. 6A–I or 7A–L. Most preferably, the polypeptide is the human NAIP polypeptide of FIGS. 6A–I. Fragments including at least two BIR domains, as provided herein, are also a part of the invention. Preferably, the fragment has at least three BIR domains. For example, polypeptides encoded by the nucleic acids described above having deletions between nucleic acids 1360 and the end of the gene are a part of the invention. In one embodiment, the NAIP fragments included those NAIP fragments comprising at least 15 sequential amino acids of SEQ ID NOs: 22 or 24. Most preferably the fragment includes at least a portion of exon 14a or exon 17.

In another aspect, the invention features a recombinant mammalian polypeptide derived from NAIP that is capable of modulating apoptosis. The polypeptide may include at least two BIR domains as defined herein, preferably three BIR domains. In preferred embodiments, the NAIP amino acid sequence differs from the NAIP sequences of FIGS. 6A–I or 7A–L by only conservative substitutions or differs from the sequences encoded by the nucleic acids of SEQ ID NOs: 1, 2, 21, or 23 by deletions of amino acids carboxy terminal to the BIR domains. In other preferred embodiments the recombinant protein decreases apoptosis relative to a control by at least 5%, more preferably by 25%.

In another aspect, the invention features a method of inhibiting apoptosis in a mammal wherein the method includes: providing nucleic acid encoding a NAIP polypeptide to a cell that is susceptible to apoptosis; wherein the nucleic acid is positioned for expression in the cell; NAIP gene is under the control of regulatory sequences suitable for controlled expression of the gene(s); and the NAIP transgene is expressed at a level sufficient to inhibit apoptosis relative to a cell lacking the NAIP transgene. The nucleic acid may encode all or part of a NAIP polypeptide. It may, for example, encode two or three BIR domains, but have a deletion of the carboxy-terminal amino acids. Preferably, the nucleic acid comprises sequences encoding exon 14a, exon 17, or both.

In a related aspect, the invention features a method of inhibiting apoptosis by producing a cell that has integrated, into its genome, a transgene that includes the NAIP gene, or a fragment thereof. The NAIP gene may be placed under the control of a promoter providing constitutive expression of the NAIP gene. Alternatively, the NAIP transgene may be placed under the control of a promoter that allows expression of the gene to be regulated by environmental stimuli. For example, the NAIP gene may be expressed using a tissue-specific or cell type-specific promoter, or by a promoter that is activated by the introduction of an external signal or agent, such as a chemical signal or agent. In preferred embodiments the mammalian cell is a lymphocyte, a neuronal cell, a glial cell, or a fibroblast. In other embodiments, the cell is in an HIV-infected human, or in a mammal suffering from a neurodegenerative disease, an ischemic injury, a toxin-induced liver disease, or a myelodysplastic syndrome.

In a related aspect, the invention provides a method of inhibiting apoptosis in a mammal by providing an apoptosis-inhibiting amount of NAIP polypeptide. The NAIP polypeptide may be a full-length polypeptide, or it may be one of the fragments described herein.

In another aspect, the invention features a purified antibody that binds specifically to a NAIP protein. Such an antibody may be used in any standard immunodetection method for the detection, quantification, and purification of a NAIP polypeptide. Preferably, the antibody binds specifically to NAIP. The antibody may be a monoclonal or a polyclonal antibody and may be modified for diagnostic or for therapeutic purposes. The most preferable antibody binds the NAIP polypeptide sequences of SEQ ID NOs: 22 and/or 24, but not the NAIP polypeptide sequence disclosed in PCT/CA95/00581.

The antibodies of the invention may be prepared by a variety of methods. For example, the NAIP polypeptide, or antigenic fragments thereof, can be administered to an animal in order to induce the production of polyclonal antibodies. Alternatively, antibodies used as described herein may be monoclonal antibodies, which are prepared using hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., In Monoclonal Antibodies and T Cell Hybridomas, Elsevier, N.Y., 1981). The invention features antibodies that specifically bind human or murine NAIP polypeptides, or fragments thereof. In particular, the invention features "neutralizing" antibodies. By "neutralizing" antibodies is meant antibodies that interfere with any of the biological activities of the NAIP polypeptide, particularly the ability of NAIP to inhibit apoptosis. The neutralizing antibody may reduce the ability of NAIP polypeptides to inhibit apoptosis by, preferably 50%, more preferably by 70%, and most preferably by 90% or more. Any standard assay of apoptosis, including those described herein, may be used to assess potentially neutralizing antibodies.

In addition to intact monoclonal and polyclonal anti-NAIP antibodies, the invention features various genetically engineered antibodies, humanized antibodies, and antibody fragments, including F(ab')2, Fab', Fab, Fv, and sFv fragments. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also features of the invention (Green et al., *Nature Genetics* 7:13–21, 1994).

Ladner (U.S. Pat. Nos. 4,946,778 and 4,704,692) describes methods for preparing single polypeptide chain antibodies. Ward et al. (*Nature* 341:544–546, 1989) describe the preparation of heavy chain variable domains, which they term "single domain antibodies," which have high antigen-binding affinities. McCafferty et al. (*Nature* 348:552–554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describe various methods for producing immunoglobulins, and immunologically functional fragments thereof, which include at least the variable domains of the heavy and light chain in a single host cell. Cabilly et al. (U.S. Pat. No. 4,816,567) describe methods for preparing chimeric antibodies.

In another aspect, the invention features a method of identifying a compound that modulates apoptosis. The method includes providing a cell expressing or capable of expressing a NAIP polypeptide, contacting the cell with a candidate compound, and monitoring the expression of the NAIP gene or a reporter gene linked to the NAIP gene regulatory sequences, or by monitoring NAIP biological activity. An alteration in the level of expression of the NAIP gene indicates the presence of a compound that modulates apoptosis. The compound may be an inhibitor or an enhancer of apoptosis. In various preferred embodiments, the mammalian cell is a myocardial cell, a fibroblast, a neuronal cell, a glial cell, a lymphocyte (T cell or B cell), or an insect cell.

In a related aspect, the invention features methods of detecting compounds that modulate apoptosis using the interaction trap technology and NAIP polypeptides, or fragments thereof, as a component of the bait. In preferred embodiments, the compound being tested as a modulator of apoptosis is also a polypeptide.

In a related aspect, the invention features a method for analyzing the anti-apoptotic effect of a candidate NAIP is provided comprising, i) providing an expression vector for the expression of the candidate NAIP; ii) transfecting mammalian cells with said expression vector; iii) inducing the transformed cells to undergo apoptosis; and iv) comparing the survival rate of the cells with appropriate mammalian cell controls.

In yet another aspect, the invention features a method for detecting the expression of NAIP in tissues comprising, i) providing a tissue or cellular sample; ii) incubating said sample with an anti-NAIP polyclonal or monoclonal antibody; and iii) visualizing the distribution of NAIP.

In another aspect, the invention features a method for diagnosing a cell proliferation disease, or an increased likelihood of such a disease, using a NAIP nucleic acid probe or NAIP antibody. Preferably, the disease is a cancer of the central nervous system. Most preferably, the disease is selected from the group consisting of neuroblastoma, meningioma, glialblastoma, astracystoma, neuroastrocytoma, promyelocytic leukemia, a HeLa-type carcinoma, chronic myelogenous leukemia (preferably using xiap or hiap-2 related probes), lymphoblastic leukemia (preferably using a xiap related probe), Burkitt's lymphoma, colorectal adenocarcinoma, lung carcinoma, and melanoma. Preferably, a diagnosis is indicated by a 2-fold increase in expression or activity, more preferably, at least a 10-fold increase in expression or activity.

In another aspect, the invention includes a method of treating a patient having deleterious levels of apoptosis. Where the patient has more apoptosis than desirable or is otherwise deficient in normal NAIP, the method includes the step of administering to said patient a therapeutically effective amount of NAIP protein, NAIP nucleic acid, or a compound which enhances NAIP activity levels in a form which allows delivery to the cells that are undergoing more apoptosis than is therapeutically desirable. In one preferred embodiment, the cell having deleterious levels of apoptosis is a myocardial cell in a patient diagnosed with a cardiac condition.

Where insufficient levels of apoptosis are likely to occur, antisense NAIP nucleic acid, NAIP antibody, or a compound which otherwise decreases NAIP activity levels may be administered. Treatment of SMA is specifically excluded from the invention. Thus, apoptosis may be induced in a cell by administering to the cell a negative regulator of the NAIP-dependent anti-apoptotic pathway. The negative regulator may be, but is not limited to, a NAIP polypeptide fragment or purified NAIP specific antibody. For example, the antibody may bind to an epitope in any one of the three BIR domains. The negative regulator may also be a NAIP antisense RNA molecule.

Skilled artisans will recognize that a mammalian NAIP, or a fragment thereof (as described herein), may serve as an active ingredient in a therapeutic composition. This composition, depending on the NAIP or fragment included, may be used to modulate apoptosis and thereby treat any condition that is caused by a disturbance in apoptosis. Thus, it will be understood that another aspect of the invention described herein, includes the compounds of the invention in a pharmaceutically acceptable carrier.

As summarized above, a NAIP nucleic acid, polypeptide, or antibody may be used to modulate apoptosis. Furthermore, a NAIP nucleic acid, polypeptide, or antibody may be used in the discovery and/or manufacture of a medicament for the modulation of apoptosis.

By "NAIP gene" is meant a gene encoding a polypeptide having at least exon 14a or exon 17 of FIGS. 6A–I or 7A–L, or the sequence of FIGS. 5A–L, SEQ ID NO: 2, wherein at least 10 carboxy-terminal nucleic acids have been deleted to enhance activity, as described above. In preferred embodiments the NAIP gene encodes a polypeptide which is capable of inhibiting apoptosis or eliciting antibodies which specifically bind NAIP. In preferred embodiments the NAIP gene is a gene having about 50% or greater nucleotide sequence identity to the NAIP amino acid encoding sequences of FIGS. 6A–I or 7A–L. In another preferred embodiment, the NAIP gene encodes a fragment sufficient to inhibit apoptosis. Preferably, the region of sequence over which identity is measured is a region encoding exon 14a or exon 17. Mammalian NAIP genes include nucleotide sequences isolated from any mammalian source. Preferably, the mammal is a human.

The term "NAIP gene" is meant to encompass any NAIP gene, which is characterized by its ability to modulate apoptosis and encodes a polypeptide that has at least 20%, preferably at least 30%, and most preferably at least 50% amino acid sequence identity with the NAIP polypeptides shown in FIGS. 6A–I and 7A–L. Specifically excluded is the full length sequence disclosed in PCT/CA95/00581 and shown in SEQ ID NO: 1.

By "NAIP protein" or "NAIP polypeptide" is meant a polypeptide, or fragment thereof, encoded by a NAIP gene as described above.

By "modulating apoptosis" or "altering apoptosis" is meant increasing or decreasing the number of cells that would otherwise undergo apoptosis in a given cell population. Preferably, the cell population is selected from a group including T cells, neuronal cells, fibroblasts, myocardial cells, or any other cell line known to undergo apoptosis in a laboratory setting (e.g., the baculovirus infected insect cells). It will be appreciated that the degree of modulation provided by a NAIP or a modulating compound in a given assay will vary, but that one skilled in the art can determine the statistically significant change in the level of apoptosis which identifies a NAIP or a compound which modulates a NAIP.

By "inhibiting apoptosis" is meant any decrease in the number of cells which undergo apoptosis relative to an untreated control. Preferably, the decrease is at least 25%, more preferably the decrease is 50%, and most preferably the decrease is at least one-fold.

By "polypeptide" is meant any chain of more than two amino acids, regardless of post-translational modification such as glycosylation or phosphorylation.

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; phenylalanine, and tyrosine.

By "substantially pure polypeptide" is meant a polypeptide that has been separated from the components that naturally accompany it. Typically, the polypeptide is substantially pure when it is at least 60%, by weight, free from the proteins and naturally occurring organic molecules with which it is naturally associated. Preferably, the polypeptide is a NAIP polypeptide that is at least 75%, more preferably at least 90%, and most preferably at least 99%, by weight, pure. A substantially pure NAIP polypeptide may be obtained, for example, by extraction from a natural source (e.g., a fibroblast, neuronal cell, or lymphocyte) by expression of a recombinant nucleic acid encoding a NAIP polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a NAIP polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammalian (e.g., rodents such as rats or mice) and the DNA (transgene) is inserted by artifice into the nuclear genome.

By "transformation" is meant any method for introducing foreign molecules into a cell. Lipofection, calcium phosphate precipitation, retroviral delivery, electroporation, and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., a NAIP polypeptide, a recombinant protein, or a RNA molecule).

By "reporter gene" is meant a gene whose expression may be assayed; such genes include, without limitation, glucuronidase (GUS), luciferase, chloramphenicol transacetylase (CAT), and β-galactosidase, and green fluorescent protein (GFP).

By "promoter" is meant minimal sequence sufficient to direct transcription. Also included in the invention are those promoter elements which are sufficient to render promoter-dependent gene expression controllable for cell type-specific, tissue-specific or inducible by external signals or agents; such elements may be located in the 5' or 3' regions of the native gene.

By "operably linked" is meant that a gene and one or more regulatory sequences are connected in such a way as to permit gene expression when the appropriate molecules (e.g., transcriptional activator proteins are bound to the regulatory sequences).

By "conserved region" is meant any stretch of six or more contiguous amino acids exhibiting at least 30%, preferably 50%, and most preferably 70% amino acid sequence identity between two or more of the NAIP family members, (e.g., between human NAIP and murine NAIP).

By "carboxy terminal amino acids of NAIP" is meant the amino acids of carboxy terminal to the three BIR domains of the NAIP gene. For example, the amino acids encoded beyond nucleic acid 1360 of SEQ ID NO: 21 are carboxy terminal.

By "detectably-labeled" is meant any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as $^{32}P$ or $^{35}S$), and nonradioactive labeling (e.g., chemiluminescent labeling or fluorescein labeling).

By "antisense," as used herein in reference to nucleic acids, is meant a nucleic acid sequence, regardless of length, that is complementary to the coding strand of a gene.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a NAIP specific antibody. A purified antibody may be obtained, for example, by affinity chromatography using recombinantly-produced protein or conserved motif peptides and standard techniques.

By "specifically binds" is meant an antibody that recognizes and binds a protein but that does not substantially recognize and bind other molecules in a sample, e.g., a biological sample, that naturally includes protein. The preferred antibody binds to the NAIP peptide sequence of SEQ ID NO: 2 but does not bind to the NAIP sequence disclosed in PCT/CA 95/00581.

Other features and advantages of the invention will be apparent from the following description of the preferred embodiments thereof, and from the claims.

BRIEF DESCRIPTION OF THE DRAWINGS

Various aspects of the invention are described with respect to the drawings wherein:

FIGS. 1A–B are cells infected with adenovirus encoding NAIP-myc detected by a mouse anti-myc monoclonal antibody or by a rabbit anti human NAIP polyclonal antibody. FIG. 1C are cells infected with adenovirus encoding NAIP detected by the NAIP polyclonal antibody. FIG. 1D shows expression of myc-NAIP in representative pooled cell lines by immunofluorescence detected with antibodies against myc. FIGS. 1E–F shows rat-1 NAIP transfectants detected by E anti-myc and F anti-NAIP antibodies.

FIGS. 2A–B depict the viability of a CHO cells deprived of serum in adenovirus infected cells and pooled transformants, respectively. FIGS. 2C–H depict cell death induced by menadione in adenvirus infected CHO (FIGS. 2C–D) and Rat-1 (FIGS. 2E–F and G–H) adenovirus infected cells and pooled transformants respectively. FIG. 21 depicts adenovirus infected cells and FIG. 2J depicts pooled transformants of TNF-α/cyclohexamide treated HeLa cells.

FIG. 3A depicts anterior horn cells, FIG. 3B depicts intermediolateral neurons, FIG. 3C depicts dorsal roots, and FIG. 3D depicts ventral roots.

FIGS. 5A–L show the sequences naip-o (SEQ ID NO: 1) and naip.s (SEQ ID NO: 2) obtained in 2 separate sequencings of the NAIP gene.

FIGS. 6A–I show a preferred NAIP cDNA (SEQ ID NO: 21) sequence and the predicted NAIP polypeptide sequence (SEQ ID NO: 22).

FIGS. 7A–L show a NAIP nucleic acid sequence including intron-exon boundaries (SEQ ID NO: 23) and the predicted NAIP polypeptide sequence (SEQ ID NO: 24).

DETAILED DESCRIPTION OF THE PREFERRED EMBODIMENT

Figure 1A:
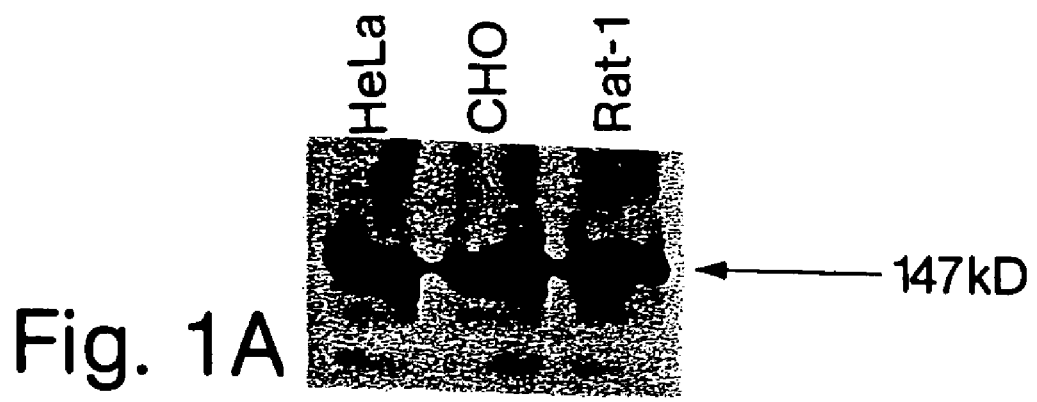
FIGS. 1A–F show the expression of NAIP in HeLa, CHO, and Rat-1 pooled stable lines and adenovirus infected cells analysed by Western blotting (FIGS. 1A–D) and immunofluorescence.

Although the precise site and mechanism of NAIP's anti-apoptotic effect is unknown, it is now demonstrated that NAIP is clearly involved in apoptotic pathways in mammalian cells. In addition, immunofluorescence localization indicates that NAIP is expressed in motor, but not sensory neurons. These findings are in keeping with the protein acting as a negative regulator of apoptosis, most particularly neuronal apoptosis, and when deficient or absent, contributes to the neurodegenerative phenotypes such as SMA and ALS.

I. The NAIP Gene.

There are two nearly identical copies of NAIP on 5q13.1. The complete NAIP gene, shown in FIGS. 7A–L, contains 18 exons (1 to 14 and 14a to 17) and spans an estimated 90 kb of genomic DNA. (Other intermediate sequences obtained are shown in FIGS. 5A–L and 6A–I). The NAIP coding region spans 4212 nucleotides resulting in a predicted gene product of 1404 amino acids (SEQ ID NO: 22). The total length of the NAIP gene spans 6228 nucleotides (SEQ ID NO: 23) with a 395 nucleotide 5'UTR and a 1621 nucleotide 3'UTR. The complete sequence, SEQ ID NO: 2, allows one skilled in the art to develop probes and primers for the identification of homologous sequences and for the identification of mutations within the DNA. Both 5' and 3' regions may also prove useful as encoding binding sites for agents which may up or down-regulate the gene further delineating the NAIP pathway and function. The sequences identified as SEQ ID NOs: 2 and 23 are also useful for protein expression in appropriate vectors and hosts to produce NAIP and study its function as well as to develop antibodies. Sequencing of the PAC 125D9 154 kb, which was identified as a likely site of the SMA gene, resulted in the identification of the NAIP sequence shown in FIGS. 5A–L, SEQ ID NO: 1. An additional coding sequence, exon 14a, has since been identified and is provided herewith. The NAIP DNA sequence containing exon 14a appears to be a predominant gene isoform which is not deleted or mutated in SMA patients. The techniques and primers used for the isolation and application of exon 14a from the human fetal spinal cord cDNA libraries was as described for the identification of the other exons and detailed in Example 4. Additional screening of cDNA libraries combined with analysis of PAC 125D9 genomic DNA sequence has resulted in the identification of a novel 3' end of NAIP which includes additional exon 17 sequence.

II. Synthesis of NAIP.

The characteristics of the cloned NAIP gene sequence may be analyzed by introducing the sequence into various cell types or using in vitro extracellular systems. The function of the NAIP may then be examined under different physiological conditions. The NAIP DNA sequence may be manipulated in studies to understand the expression of the gene and gene product. Alternatively, cell lines may be produced which over express the gene product allowing purification of NAIP for biochemical characterization, large-scale production, antibody production, and patient therapy.

For protein expression, eukaryotic and prokaryotic expression systems may be generated in which the NAIP gene sequence is introduced into a plasmid or other vector which is then introduced into living cells. Constructs in which the NAIP cDNA sequence containing the entire open reading frame inserted in the correct orientation into an expression plasmid may be used for protein expression. Alternatively, portions of the sequence, including wild type or mutant NAIP sequences, may be inserted. Prokaryotic and eukaryotic expression systems allow various important functional domains of the protein to be recovered as fusion proteins and then used for binding, structural and functional studies, and also for the generation of appropriate antibodies. If a NAIP increases apoptosis, it may be desirable to express that protein under control of an inducible promotor.

Typical expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Some vectors contain selectable markers such as neomycin resistance that permit isolation of cells by growing them under selective conditions. Stable long-term vectors may be maintained as freely replicating entities by using regulatory elements of viruses. Cell lines may also be produced which have integrated the vector into the genomic DNA and in this manner the gene product is produced on a continuous basis.

Expression of foreign sequences in bacteria such as *E.coli* require the insertion of the NAIP sequence into an expression vector, usually a bacterial plasmid. This plasmid vector contains several elements such as sequences encoding a selectable marker that assures maintenance of the vector in the cell, a controllable transcriptional promoter (i.e. lac) which upon induction can produce large amounts of mRNA from the cloned gene, translational control sequences and a polylinker to simplify insertion of the gene in the correct orientation within the vector. In a simple *E. coli* expression vector utilizing the lac promoter, the expression vector plasmid contains a fragment of the *E.coli* chromosome containing the lac promoter and the neighboring lacZ gene. In the presence of the lactose analog IPTG, RNA polymerase normally transcribes the lacZ gene producing lacZ mRNA which is translated into the encoded protein, β-galactosidase. The lacZ gene can be cut out of the expression vector with restriction enzymes and replaced by NAIP gene sequence. When this resulting plasmid is transfected into *E.coli*, addition of IPTG and subsequent transcription from the lac promoter produces NAIP mRNA, which is translated into NAIP.

Once the appropriate expression vector containing the NAIP gene is constructed it is introduced into an appropriate *E.coli* strain by transformation techniques including calcium phosphate transfection, DEAE-dextran transfection, electroporation, microinjection, protoplast fusion, and liposome-mediated transfection.

The host cell which may be transfected with the vector of this invention may be selected from the group consisting of *E.coli, pseudomonas, bacillus subtillus*, or other *bacili*, other bacteria, yeast, fungi, insect (using baculoviral vectors for expression), mouse or other animal or human tissue cells. Mammalian cells can also be used to express the NAIP protein using a vaccinia virus expression system.

In vitro expression of proteins encoded by cloned DNA is also possible using the T7 late-promoter expression system. This system depends on the regulated expression of T7 RNA polymerase which is an enzyme encoded in the DNA of bacteriophage T7. The T7 RNA polymerase transcribes DNA beginning within a specific 23-bp promoter sequence called the T7 late promoter. Copies of the T7 late promoter are located at several sites on the T7 genome, but none is present in *E.coli* chromosomal DNA. As a result, in T7 infected cells, T7 RNA polymerase catalyzes transcription of viral genes but not of E.coli genes. In this expression system recombinant E.coli cells are first engineered to carry the gene encoding T7 RNA polymerase next to the lac promoter. In the presence of IPTG, these cells transcribe the T7 polymerase gene at a high rate and synthesize abundant amounts of T7 RNA polymerase. These cells are then transformed with plasmid vectors that carry a copy of the T7 late promoter protein. When IPTG is added to the culture medium containing these transformed E.coli cells, large amounts of T7 RNA polymerase are produced. The polymerase then binds to the T7 late promoter on the plasmid expression vectors, catalyzing transcription of the inserted cDNA at a high rate. Since each E.coli cell contains many copies of the expression vector, large amounts of mRNA corresponding to the cloned cDNA can be produced in this system and the resulting protein can be radioactively labeled. Plasmid vectors containing late promoters and the corresponding RNA polymerases from related bacteriophages such as T3, T5, and SP6 may also be used for in vitro production of proteins from cloned DNA. E.coli can also be used for expression by infection with M13 Phage mGPI-2. E.coli vectors can also be used with phage lambda regulatory sequences, by fusion protein vectors, by maltose-binding protein fusions, and by glutathione-S-transferase fusion proteins.

A preferred expression system is the baculovirus system using, for example, the vector pBacPAK9, which is available from Clontech (Palo Alto, Calif.). If desired, this system may be used in conjunction with other protein expression techniques, for example, the myc tag approach described by Evan et al. (*Mol. Cell Biol.* 5:3610–3616, 1985).

Eukaryotic expression systems permit appropriate post-translational modifications to expressed proteins. This allows for studies of the NAIP gene and gene product including determination of proper expression and post-translational modifications for biological activity, identifying regulatory elements located in the 5' region of the NAIP gene and their role in tissue regulation of protein expression. It also permits the production of large amounts of normal and mutant proteins for isolation and purification, to use cells expressing NAIP as a functional assay system for antibodies generated against the protein, to test the effectiveness of pharmacological agents or as a component of a signal transduction system, to study the function of the normal complete protein, specific portions of the protein, or of naturally occurring polymorphisms and artificially produced mutated proteins. The NAIP DNA sequence can be altered using procedures such as restriction enzyme digestion, DNA polymerase fill-in, exonuclease deletion, terminal deoxynucleotide transferase extension, ligation of synthetic or cloned DNA sequences, and site-directed sequence alteration using specific oligonucleotides together with PCR.

A NAIP may be produced by a stably-transfected mammalian cell line. A number of vectors suitable for stable transfection of mammalian cells are available to the public, e.g., see Pouwels et al. (supra), as are methods for constructing such cell lines (see Ausubel et al. (supra)). In one example, cDNA encoding a NAIP is cloned into an expression vector that includes the dihydrofolate reductase (DHFR) gene. Integration of the plasmid, and therefore, integration of the NAIP-encoding gene into the host cell chromosome is selected for by inclusion of 0.01–300 μM methotrexate in the cell culture medium (as described, Ausubel et al., supra). This dominant selection can be accomplished in most cell types. Recombinant protein expression can be increased by DHFR-mediated amplification of the transfected gene.

Methods for selecting cell lines bearing gene amplifications are described in Ausubel et al. (supra). These methods generally involve extended culture in medium containing gradually increasing levels of methotrexate. The most commonly used DHFR-containing expression vectors are pCVSEII-DHFR and pAdD26SV(A) (described in Ausubel et al., supra). The host cells described above or, preferably, a DHFR-deficient CHO cell line (e.g., CHO DHFR⁻ cells, ATCC Accession No. CRL 9096) are among those most preferred for DHFR selection of a stably-transfected cell line or DHFR-mediated gene amplification.

Once the recombinant protein is expressed, it is isolated by, for example, affinity chromatography. In one example, an anti-NAIP antibody, which may be produced by the methods described herein, can be attached to a column and used to isolate the NAIP protein. Lysis and fractionation of NAIP-harboring cells prior to affinity chromatography may be performed by standard methods (see e.g., Ausubel et al., supra). Once isolated, the recombinant protein can, if desired, be purified further by e.g., by high performance liquid chromatography (HPLC; e.g., see Fisher, "Laboratory Techniques in Biochemistry and Molecular Biology," Work and Burdon, Eds., Elsevier, 1980).

Polypeptides of the invention, particularly short NAIP fragments, can also be produced by chemical synthesis (e.g., by the methods described in "Solid Phase Peptide Synthesis," 2nd ed., 1984 The Pierce Chemical Co., Rockford, Ill.). These general techniques of polypeptide expression and purification can also be used to produce and isolate useful NAIP fragments or analogs, as described herein.

Those skilled in the art of molecular biology will understand that a wide variety of expression systems may be used to produce the recombinant protein. The precise host cell used is not critical to the invention. The NAIP protein may be produced in a prokaryotic host (e.g., *E. coli*) or in a eukaryotic host (e.g., *S. cerevisiae*, insect cells such as Sf21 cells, or mammalian cells such as COS-1, NIH 3T3, or HeLa cells). These cells are publically available, for example, from the American Type Culture Collection, Rockville, Md.; see also Ausubel et al., "Current Protocols in Molecular Biology," John Wiley & Sons, New York, N.Y., 1994. The method of transduction and the choice of expression vehicle will depend on the host system selected. Transformation and transfection methods are described, e.g., in Ausubel et al. (supra), and expression vehicles may be chosen from those provided, e.g., in "Cloning Vectors: A Laboratory Manual," (P. H. Pouwels et al., 1985, Supp. 1987).

III. Testing for the Presence of NAIP Biological Activity.

To analyze the effect of NAIP on apoptosis in a first approach, expression plasmids alone or encoding nearly full length NAIP or Bcl-2 (a protein which functions under normal conditions to protect cells against apoptosis) were transfected into CHO, Rat-1, and HeLa cells followed by G418 selection. Initially, a NAIP cDNA was isolated by probing a human fetal brain cDNA library with a genomic DNA insert of a cosmid from the constructed cosmid library, and a cDNA fragment encoding most of the three BIR domains corresponding to the NAIP gene sequence was isolated.

IV. Cellular Distribution of NAIP.

We have looked at the distribution of NAIP using immunofluorescence of labeled antibodies and find NAIP is expressed in at least the following tissues: motor neurons, myocardial cells, liver, placenta, and CNS.

V. NAIP Fragments.

The BIR domains of NAIP appear to be both necessary and sufficient for NAIP biological activity. Surprisingly, we have reason to believe carboxy terminal deletions of NAIP amino acids actually enhances inhibition of apoptosis by NAIP. Deletions may be up to the end of the last NAIP BIR domain (i.e., the third), but need not delete the entire region carboxy terminal to the third BIR domains.

VI. NAIP Antibodies.

In order to prepare polyclonal antibodies, NAIP, fragments of NAIP, or fusion proteins containing defined portions or all of the NAIP protein can be synthesized in bacteria by expression of corresponding DNA sequences in a suitable cloning vehicle. Fusion proteins are commonly used as a source of antigen for producing antibodies. Two widely used expression systems for E.coli are lacZ fusions using the pUR series of vectors and trpE fusions using the pATH vectors. The protein can then be purified, coupled to a carrier protein and mixed with Freund's adjuvant (to help stimulate the antigenic response by the rabbits) and injected into rabbits or other laboratory animals. Alternatively, protein can be isolated from NAIP expressing cultured cells. Following booster injections at bi-weekly intervals, the rabbits or other laboratory animals are then bled and the sera isolated. The sera can be used directly or purified prior to use, by various methods including affinity chromatography employing Protein A SEPHAROSE, Antigen SEPHAROSE, Anti-mouse-Ig-SEPHAROSE. The sera can then be used to probe protein extracts from tissues run on a polyacrylamide gel to identify the NAIP protein. Alternatively, synthetic peptides can be made to the antigenic portions of the protein and used to innoculate the animals.

In order to generate peptide for use in making NAIP-specific antibodies, a NAIP coding sequence (i.e., amino acid fragments shown in SEQ ID NOs: 22 and 24) can be expressed as a C-terminal fusion with glutathione S-transferase (GST; Smith et al., Gene 67:31–40, 1988). The fusion protein can be purified on glutathione-SEPHAROSE (agarose gel bead) beads, eluted with glutathione, and cleaved with thrombin (at the engineered cleavage site), and purified to the degree required to successfully immunize rabbits. Primary immunizations can be carried out with Freund's complete adjuvant and subsequent immunizations performed with Freund's incomplete adjuvant. Antibody titres are monitored by Western blot and immunoprecipitation analyses using the thrombin-cleaved NAIP fragment of the GST-NAIP fusion protein. Immune sera are affinity purified using CNBr-SEPHAROSE-coupled (CNBr-agarose gel bead-coupled) NAIP protein. Antiserum specificity is determined using a panel of unrelated GST proteins (including GSTp53, Rb, HPV-16 E6, and E6-AP) and GST-trypsin (which was generated by PCR using known sequences).

It is also understood by those skilled in the art that monoclonal NAIP antibodies may be produced by culturing cells actively expressing the protein or isolated from tissues. The cell extracts, or recombinant protein extracts, containing the NAIP protein, may for example, be injected in Freund's adjuvant into mice. After being injected, the mice spleens may be removed and resuspended in phosphate buffered saline (PBS). The spleen cells serve as a source of lymphocytes, some of which are producing antibody of the appropriate specificity. These are then fused with a permanently growing myeloma partner cells, and the products of the fusion are plated into a number of tissue culture wells in the presence of a selective agent such as HAT. The wells are then screened by ELISA to identify those containing cells making binding antibody. These are then plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A SEPHAROSE (agarose gel bead), ion-exchange chromatography, as well as variations and combinations of these techniques. Truncated versions of monoclonal antibodies may also be produced by recombinant methods in which plasmids are generated which express the desired monoclonal antibody fragment(s) in a suitable host.

As an alternate or adjunct immunogen to GST fusion proteins, peptides corresponding to relatively unique hydrophilic regions of NAIP may be generated and coupled to keyhole limpet hemocyanin (KLH) through an introduced C-terminal lysine. Antiserum to each of these peptides is similarly affinity purified on peptides conjugated to BSA, and specificity is tested by ELISA and Western blotting using peptide conjugates, and by Western blotting and immunoprecipitation using NAIP expressed as a GST fusion protein.

Alternatively, monoclonal antibodies may be prepared using the NAIP proteins described above and standard hybridoma technology (see, e.g., Kohler et al., Nature 256: 495, 1975; Kohler et al., Eur. J. Immunol. 6:511, 1976; Kohler et al., Eur. J. Immunol. 6:292, 1976; Hammerling et al., In "Monoclonal Antibodies and T Cell Hybridomas", Elsevier, N.Y., 1981; Ausubel et al., supra). Once produced, monoclonal antibodies are also tested for specific NAIP recognition by Western blot or immunoprecipitation analysis (by the methods described in Ausubel et al., supra).

Antibodies that specifically recognize NAIP (or fragments of NAIP), such as those described herein containing one or more BIR domains are considered useful in the invention. They may, for example, be used in an immunoassay to monitor NAIP expression levels or to determine the subcellular location of a NAIP or NAIP fragment produced by a mammal. Antibodies that inhibit NAIP described herein may be especially useful in inducing apoptosis in cells undergoing undesirable proliferation.

Preferably, antibodies of the invention are produced using NAIP sequence that does not reside within highly conserved regions, and that appears likely to be antigenic, as analyzed by criteria such as those provided by the Peptide structure program (Genetics Computer Group Sequence Analysis Package, Program Manual for the GCG Package, Version 7, 1991) using the algorithm of Jameson and Wolf (CABIOS 4:181, 1988). These fragments can be generated by standard techniques, e.g., by the PCR, and cloned into the pGEX expression vector (Ausubel et al., supra). Fusion proteins are expressed in E. coli and purified using a glutathione agarose affinity matrix as described in Ausubel et al. (supra). In order to minimize the potential for obtaining antisera that is non-specific, or exhibits low-affinity binding to NAIP, two or three fusions are generated for each protein, and each fusion is injected into at least two rabbits. Antisera are raised by injections in series, preferably including at least three booster injections.

VII. Use of NAIP Antibodies.

Antibodies to NAIP may be used, as noted above, to detect NAIP or inhibit the protein. In addition, the antibodies coupled to compounds for diagnostic and/or therapeutic uses such as radionucleotides for imaging and therapy and liposomes for the targeting of compounds to a specific tissue location.

VIII. Detection of NAIP Gene Expression.

As noted, the antibodies described above may be used to monitor NAIP protein expression. In addition, in situ hybridization is a method that may be used to detect the expression of the NAIP gene. In situ hybridization relies upon the hybridization of a specifically labeled nucleic acid probe to the cellular RNA in individual cells or tissues. Therefore, it allows the identification of mRNA within intact tissues, such as the brain. In this method, oligonucleotides or cloned nucleotide (RNA or DNA) fragments corresponding to unique portions of the NAIP gene are used to detect specific mRNA species, e.g., in the brain. In this method a rat is anesthetized and transcardially perfused with cold PBS, followed by perfusion with a formaldehyde solution. The brain or other tissues is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the primer is made by nick translation and incubated with the sectioned brain tissue. After incubation and air drying, the labeled areas are visualized by autoradiography. Dark spots on the tissue sample indicate hybridization of the probe with NAIP mRNA which demonstrates the expression of the protein.

IX. Identification of Molecules that Modulate NAIP Protein Expression.

NAIP cDNAs may be used to facilitate the identification of molecules that increase or decrease NAIP expression. In one approach, candidate molecules are added, in varying concentration, to the culture medium of cells expressing NAIP mRNA. NAIP expression is then measured, for example, by Northern blot analysis (Ausubel et al., supra) using a NAIP cDNA, or cDNA or RNA fragment, as a hybridization probe. The level of NAIP expression in the presence of the candidate molecule is compared to the level of NAIP expression in the absence of the candidate molecule, all other factors (e.g., cell type and culture conditions) being equal.

The effect of candidate molecules on NAIP-mediated apoptosis may, instead, be measured at the level of translation by using the general approach described above with standard protein detection techniques, such as Western blotting or immunoprecipitation with a NAIP-specific antibody (e.g., the NAIP antibody described herein).

Compounds that modulate the level of NAIP may be purified, or substantially purified, or may be one component of a mixture of compounds such as an extract or supernatant obtained from cells (Ausubel et al., supra). In an assay of a mixture of compounds, NAIP expression is tested against progressively smaller subsets of the compound pool (e.g., produced by standard purification techniques such as HPLC or FPLC until a single compound or minimal number of effective compounds is demonstrated to modulate NAIP expression.

Compounds may also be screened for their ability to modulate NAIP apoptosis inhibiting activity. In this approach, the degree of apoptosis in the presence of a candidate compound is compared to the degree of apoptosis in its absence, under equivalent conditions. Again, the screen may begin with a pool of candidate compounds, from which one or more useful modulator compounds are isolated in a step-wise fashion. Apoptosis activity may be measured by any standard assay, for example, those described herein.

Another method for detecting compounds that modulate the activity of NAIPs is to screen for compounds that interact physically with a given NAIP polypeptide. These compounds may be detected by adapting interaction trap expression systems known in the art. These systems detect protein interactions using a transcriptional activation assay and are generally described by Gyuris et al. (*Cell* 75:791–803, 1993) and Field et al., *Nature* 340:245–246, 1989), and are commercially available from Clontech (Palo Alto, Calif.). In addition, PCT Publication WO 95/28497 describes an interaction trap assay in which proteins involved in apoptosis, by virtue of their interaction with Bcl-2, are detected. A similar method may be used to identify proteins and other compounds that interact with NAIP.

Compounds or molecules that function as modulators of NAIP-mediated cell death may include peptide and non-peptide molecules such as those present in cell extracts, mammalian serum, or growth medium in which mammalian cells have been cultured.

A molecule that promotes an increase in NAIP expression or NAIP activity is considered particularly useful in the invention; such a molecule may be used, for example, as a therapeutic to increase cellular levels of NAIP and thereby exploit the ability of NAIP polypeptides to inhibit apoptosis.

A molecule that decreases NAIP activity (e.g., by decreasing NAIP gene expression or polypeptide activity) may be used to decrease cellular proliferation. This would be advantageous in the treatment of neoplasms or other cell proliferative diseases.

Molecules that are found, by the methods described above, to effectively modulate NAIP gene expression or polypeptide activity may be tested further in animal models. If they continue to function successfully in an in vivo setting, they may be used as therapeutics to either inhibit or enhance apoptosis, as appropriate.

X. Therapies.

Therapies may be designed to circumvent or overcome an NAIP gene defect or inadequate NAIP gene expression, and thus moderate and possibly prevent apoptosis. The NAIP gene is expressed in the liver, myocardium, and placenta, as well as in the CNS. Hence, in considering various therapies, it is understood that such therapies may be targeted at tissue other than the brain, such as the liver, myocardium, and any other tissues subsequently demonstrated to express NAIP.

a) Protein Therapy

Treatment or prevention of apoptosis can be accomplished by replacing mutant or insufficient NAIP protein with normal protein, by modulating the function of mutant protein, or by delivering normal NAIP protein to the appropriate cells. Once the biological pathway of the NAIP protein has been completely understood, it may also be possible to modify the pathophysiologic pathway (e.g., a signal transduction pathway) in which the protein participates in order to correct the physiological defect.

To replace a mutant protein with normal protein, or to add protein to cells which no longer express sufficient NAIP, it is necessary to obtain large amounts of pure NAIP from cultured cell systems which can express the protein. Delivery of the protein to the affected tissues can then be accomplished using appropriate packaging or administrating systems. Alternatively, small molecule analogs may be used and administered to act as NAIP agonists and in this manner produce a desired physiological effect. Methods for finding such molecules are provided herein.

b) Gene Therapy Gene therapy is another potential therapeutic approach in which normal copies of the NAIP gene are introduced into selected tissues to successfully code for normal and abundant protein in affected cell types. The gene must be delivered to those cells in a form in which it can be taken up and code for sufficient protein to provide effective function. Alternatively, in some mutants it may be possible to prevent apoptosis by introducing another copy of the homologous gene bearing a second mutation in that gene or to alter the mutation, or use another gene to block any negative effect.

Transducing retroviral vectors can be used for somatic cell gene therapy especially because of their high efficiency of infection and stable integration and expression. The targeted cells however must be able to divide and the expression of the levels of normal protein should be high. The full length NAIP gene, or portions thereof, can be cloned into a retroviral vector and driven from its endogenous promoter or from the retroviral long terminal repeat or from a promoter specific for the target cell type of interest (such as neurons). Other viral vectors which can be used include adeno-associated virus, vaccinia virus, bovine papilloma virus, or a herpes virus such as Epstein-Barr virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Antisense based strategies can be employed to explore NAIP gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target NAIP mRNA. Antisense strategies may use a variety of approaches including the use of antisense oligonucleotides, injection of antisense RNA and transfection of antisense RNA expression vectors. Antisense effects can be induced by control (sense) sequences, however, the extent of phenotypic changes are highly variable. Phenotypic effects induced by antisense effects are based on changes in criteria such as protein levels, protein activity measurement, and target mRNA levels.

Transplantation of normal genes into the affected cells of a patient can also be useful therapy. In this procedure, normal NAIP is transferred into a cultivatable cell type, either exogenously or endogenously to the patient. These cells are then injected serotologically into the targeted tissue(s).

Retroviral vectors, adenoviral vectors, adeno associated viral vectors, or other viral vectors with the appropriate tropism for cells likely to be involved in apoptosis (e.g., epithelial cells) may be used as a gene transfer delivery system for a therapeutic NAIP gene construct. Numerous vectors useful for this purpose are generally known (Miller, *Human Gene Therapy* 15–14, 1990; Friedman, *Science* 244:1275–1281, 1989; Eglitis and Anderson, *BioTechniques* 6:608–614, 1988; Tolstoshev and Anderson, *Current Opinion in Biotechnology* 1:55–61, 1990; Sharp, *The Lancet* 337:1277–1278, 1991; Cornetta et al., *Nucleic Acid Research and Molecular Biology* 36:311–322, 1987; Anderson, *Science* 226:401–409, 1984; Moen, *Blood Cells* 17:407–416, 1991; Miller et al., *Biotechniques* 7:980–990, 1989; Le Gal La Salle et al., *Science* 259:988–990, 1993; and Johnson, *Chest* 107:77S-83S, 1995). Retroviral vectors are particularly well developed and have been used in clinical settings (Rosenberg et al., *N. Engl. J. Med* 323:370, 1990; Anderson et al., U.S. Pat. No. 5,399,346). Non-viral approaches may also be employed for the introduction of therapeutic DNA into cells otherwise predicted to undergo apoptosis. For example, NAIP may be introduced into a neuron or a T cell by lipofection (Felgner et al., *Proc. Natl. Acad. Sci. USA* 84:7413, 1987; Ono et al., *Neurosci. Lett.* 117:259, 1990; Brigham et al., *Am. J. Med. Sci.* 298:278, 1989; Staubinger et al., *Meth. Enz.* 101:512, 1983), asialoorosonucoid-polylysine conjugation (Wu et al., *J. Biol. Chem.* 263:14621, 1988; Wu et al., *J. Biol. Chem.* 264:16985, 1989); or less preferably, microinjection under surgical conditions (Wolff et al., *Science* 247:1465, 1990).

For any of the methods of application described above, the therapeutic NAIP DNA construct is preferably applied to the site of the predicted apoptosis event (e.g., by injection). However, it may also be applied to tissue in the vicinity of the predicted apoptosis event or to a blood vessel supplying the cells predicted to undergo apoptosis.

In the constructs described, NAIP cDNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in neural cells, T cells, or B cells may be used to direct NAIP expression. The enhancers used could include, without limitation, those that are characterized as tissue- or cell-specific in their expression. Alternatively, if a NAIP genomic clone is used as a therapeutic construct (e.g., following its isolation by hybridization with the NAIP cDNA described above), regulation may be mediated by the cognate regulatory sequences or, if desired, by regulatory sequences derived from a heterologous source, including any of the promoters or regulatory elements described above.

Less preferably, NAIP gene therapy is accomplished by direct administration of the NAIP mRNA or antisense NAIP mRNA to a cell that is expected to undergo apoptosis. The mRNA may be produced and isolated by any standard technique, but is most readily produced by in vitro transcription using a NAIP cDNA under the control of a high efficiency promoter (e.g., the T7 promoter). Administration of NAIP antisense or mRNA to cells mRNA can be carried out by any of the methods for direct nucleic acid administration described above.

Ideally, the production of NAIP protein by any gene therapy approach will result in cellular levels of NAIP that are at least equivalent to the normal, cellular level of NAIP in an unaffected cell. Treatment by any NAIP-mediated gene therapy approach may be combined with more traditional therapies.

Another therapeutic approach within the invention involves administration of recombinant NAIP protein, either directly to the site of a predicted apoptosis event (e.g., by injection) or systemically (e.g., by any conventional recombinant protein administration technique). The dosage of NAIP depends on a number of factors, including the size and health of the individual patient, but, generally, between 0.1 mg and 100 mg inclusive are administered per day to an adult in any pharmaceutically acceptable formulation.

XI. Administration of NAIP Polypeptides, NAIP Genes, or Modulators of NAIP Synthesis or Function.

A NAIP protein, gene, or modulator may be administered within a pharmaceutically acceptable diluent, carrier, or excipient, in unit dosage form. Conventional pharmaceutical practice may be employed to provide suitable formulations or compositions to administer NAIP to patients suffering from a disease that is caused by excessive apoptosis. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for NAIP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a NAIP protein, gene, or modulatory compound may be combined with more traditional therapies for the disease such as surgery, steroid therapy, or chemotherapy for autoimmune disease; antiviral therapy for AIDS; and tissue plasminogen activator (TPA) for ischemic injury.

XII. Detection of Conditions Involving Altered Apoptosis.

NAIP polypeptides and nucleic acid sequences find diagnostic use in the detection or monitoring of conditions involving aberrant levels of apoptosis. For example, decreased expression of NAIP may be correlated with enhanced apoptosis in humans (see XII, below). Accordingly, a decrease or increase in the level of NAIP production may provide an indication of a deleterious condition. Levels of NAIP expression may be assayed by any standard technique. For example, NAIP expression in a biological sample (e.g., a biopsy) may be monitored by standard Northern blot analysis or may be aided by PCR (see, e.g., Ausubel et al., supra; "PCR Technology: Principles and Applications for DNA Amplification," H. A. Ehrlich, Ed. Stockton Press, NY; Yap et al. *Nucl. Acids. Res.* 19:4294, 1991).

Alternatively, a biological sample obtained from a patient may be analyzed for one or more mutations in the NAIP sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant NAIP detection, and each is well known in the art; examples of particular techniques are described, without limitation, in Orita et al., *Proc. Natl. Acad. Sci. USA* 86:2766–2770, 1989; Sheffield et al., *Proc. Natl. Acad. Sci. USA* 86:232–236, 1989).

In yet another approach, immunoassays are used to detect or monitor NAIP protein in a biological sample. NAIP-specific polyclonal or monoclonal antibodies (produced as described above) may be used in any standard immunoassay format (e.g., ELISA, Western blot, or RIA) to measure NAIP polypeptide levels. These levels would be compared to wild-type NAIP levels, with a decrease in NAIP production indicating a condition involving increased apoptosis. Examples of immunoassays are described, e.g., in Ausubel et al., supra. Immunohistochemical techniques may also be utilized for NAIP detection. For example, a tissue sample may be obtained from a patient, sectioned, and stained for the presence of NAIP using an anti-NAIP antibody and any standard detection system (e.g., one which includes a secondary antibody conjugated to horseradish peroxidase). General guidance regarding such techniques can be found in, e.g., Bancroft and Stevens ("Theory and Practice of Histological Technigues," Churchill Livingstone, 1982) and Ausubel et al. (supra).

In one preferred example, a combined diagnostic method may be employed that begins with an evaluation of NAIP protein production (e.g., by immunological techniques or the protein truncation test (Hogerrorst et al., *Nature Genetics* 10:208–212, 1995) and also includes a nucleic acid-based detection technique designed to identify more subtle NAIP mutations (e.g., point mutations). As described above, a number of mismatch detection assays are available to those skilled in the art, and any preferred technique may be used. Mutations in NAIP may be detected that either result in loss of NAIP expression or loss of NAIP biological activity. In a variation of this combined diagnostic method, NAIP biological activity is measured as anti-apoptotic activity using any appropriate apoptosis assay system (e.g., those described herein).

Mismatch detection assays also provide an opportunity to diagnose a NAIP-mediated predisposition to diseases caused by inappropriate apoptosis. For example, a patient heterozygous for a NAIP mutation may show no clinical symptoms and yet possess a higher than normal probability of developing one or more types of neurodegenerative, myelodysplastic or having severe sequelae to an ischemic event. Given this diagnosis, a patient may take precautions to minimize their exposure to adverse environmental factors (e.g., UV exposure or chemical mutagens) and to carefully monitor their medical condition (e.g., through frequent physical examinations). This type of NAIP diagnostic approach may also be used to detect NAIP mutations in prenatal screens. The NAIP diagnostic assays described above may be carried out using any biological sample (e.g., any biopsy sample or other tissue) in which NAIP is normally expressed. Identification of a mutant NAIP gene may also be assayed using these sources for test samples.

Alternatively, a NAIP mutation, particularly as part of a diagnosis for predisposition to NAIP-associated degenerative disease, may be tested using a DNA sample from any cell, for example, by mismatch detection techniques. Preferably, the DNA sample is subjected to PCR amplification prior to analysis.

XIII. Preventative Anti-Apoptotic Therapy.

In a patient diagnosed to be heterozygous for a NAIP mutation or to be susceptible to NAIP mutations (even if those mutations do not yet result in alteration or loss of NAIP biological activity), or a patient diagnosed with a degenerative disease (e.g., motor neuron degenerative diseases such as SMA or ALS diseases), or diagnosed as HIV positive, any of the above therapies may be administered before the occurrence of the disease phenotype. For example, the therapies may be provided to a patient who is HIV positive but does not yet show a diminished T cell count or other overt signs of AIDS. In particular, compounds shown to increase NAIP expression or NAIP biological activity may be administered by any standard dosage and route of administration (see above). Alternatively, gene therapy using a NAIP expression construct may be undertaken to reverse or prevent the cell defect prior to the development of the degenerative disease.

The methods of the instant invention may be used to reduce or diagnose the disorders described herein in any mammal, for example, humans, domestic pets, or livestock. Where a non-human mammal is treated or diagnosed, the NAIP polypeptide, nucleic acid, or antibody employed is preferably specific for that species.

XIV. Identification of Additional NAIP Genes.

Standard techniques, such as the polymerase chain reaction (PCR) and DNA hybridization, may be used to clone additional NAIP homologues in other species. Southern blots of murine genomic DNA hybridized at low stringency with probes specific for human NAIP reveal bands that correspond to NAIP and/or related family members. Thus, additional NAIP sequences may be readily identified using low stringency hybridization. Examples of murine and human NAIP-specific primers, which may be used to clone additional genes by RT-PCR.

XV. Characterization of NAIP Activity and Intracellular Localization Studies.

The ability of NAIP to modulate apoptosis can be defined in in vitro systems in which alterations of apoptosis can be detected. Mammalian expression constructs carrying NAIP cDNAs, which are either full-length or truncated, can be introduced into cell lines such as CHO, NIH 3T3, HL60, Rat-1, or Jurkat cells. In addition, SF21 insect cells may be used, in which case the NAIP gene is preferentially expressed using an insect heat shock promotor. Following transfection, apoptosis can be induced by standard methods, which include serum withdrawal, or application of staurosporine, menadione (which induces apoptosis via free radical formation), or anti-Fas antibodies. As a control, cells are cultured under the same conditions as those induced to undergo apoptosis, but either not transfected, or transfected with a vector that lacks a NAIP insert. The ability of each NAIP construct to inhibit apoptosis upon expression can be quantified by calculating the survival index of the cells, i.e., the ratio of surviving transfected cells to surviving control cells. These experiments can confirm the presence of apoptosis inhibiting activity, and as discussed below, can also be used to determine the functional region(s) of a NAIP. These assays may also be performed in combination with the application of additional compounds in order to identify compounds that modulate apoptosis via NAIP expression.

XVI. Examples of Additional Apoptosis Assays.

Specific examples of apoptosis assays are also provided in the following references. Assays for apoptosis in lymphocytes are disclosed by: Li et al., "Induction of apoptosis in uninfected lymphocytes by HIV-1 Tat protein", *Science* 268:429–431, 1995; Gibellini et al., "Tat-expressing Jurkat cells show an increased resistance to different apoptotic stimuli, including acute human immunodeficiency virustype 1 (HIV-1) infection", *Br. J. Haematol.* 89:24–33, 1995; Martin et al., "HIV-1 infection of human CD4$^+$ T cells in vitro. Differential induction of apoptosis in these cells." *J. Immunol.* 152:330–42, 1994; Terai et al., "Apoptosis as a mechanism of cell death in cultured T lymphoblasts acutely infected with HIV-1", *J. Clin Invest.* 87:1710–5, 1991; Dhein et al., "Autocrine T-cell suicide mediated by APO-1/(Fas/CD95)11, *Nature* 373:438–441, 1995; Katsikis et al., "Fas antigen stimulation induces marked apoptosis of T lymphocytes in human immunodeficiency virus-infected individuals", *J. Exp. Med.* 1815:2029–2036, 1995; Westendorp et al., Sensitization of T cells to CD95-mediated apoptosis by HIV-1 Tat and gp12O", Nature 375:497, 1995; DeRossi et al., *Virology* 198:234–44, 1994.

Assays for apoptosis in fibroblasts are disclosed by: Vossbeck et al., "Direct transforming activity of TGF-beta on rat fibroblasts", *Int. J. Cancer* 61:92–97, 1995; Goruppi et al., "Dissection of c-myc domains involved in S phase induction of NIH3T3 fibroblasts", *Oncogene* 9:1537–44, 1994; Fernandez et al., "Differential sensitivity of normal and Ha-ras transformed C3H mouse embryo fibroblasts to tumor necrosis factor: induction of bcl-2, c-myc, and manganese superoxide dismutase in resistant cells", *Oncogene* 9:2009–17, 1994; Harrington et al., "c-Myc-induced apoptosis in fibroblasts is inhibited by specific cytokines", *EMBO J.,* 13:3286–3295, 1994; Itoh et al., "A novel protein domain required for apoptosis. Mutational analysis of human Fas antigen", *J. Biol. Chem.* 268:10932–7, 1993.

Assays for apoptosis in neuronal cells are disclosed by: Melino et al., "Tissue transglutaminase and apoptosis: sense and antisense transfection studies with human neuroblastoma cells", *Mol. Cell Biol.* 14:6584–6596, 1994; Rosenbaum et al., "Evidence for hypoxia-induced, programmed cell death of cultured neurons", *Ann. Neurol.* 36:864–870, 1994; Sato et al., "Neuronal differentiation of PC12 cells as a result of prevention of cell death by bcl-2", *J. Neurobiol.* 25:1227–1234, 1994; Ferrari et al., "N-acetylcysteine D- and L-stereoisomers prevents apoptotic death of neuronal cells", *J. Neurosci.* 1516:2857–2866, 1995; Talley et al., "Tumor necrosis factor alpha-induced apoptosis in human neuronal cells: protection by the antioxidant N-acetylcysteine and the genes bcl-2 and crma", *Mol. Cell Biol.* 1585: 2359–2366, 1995; Talley et al., "Tumor Necrosis Factor Alpha-Induced Apoptosis in Human Neuronal Cells: Protection by the Antioxidant N-Acetylcysteine and the Genes bcl-2 and crma", *Mol. Cell. Biol.* 15:2359–2366, 1995; Walkinshaw et al., "Induction of apoptosis in catecholaminergic PC12 cells by L-DOPA. Implications for the treatment of Parkinson's disease.", *J. Clin. Invest.* 95:2458–2464, 1995.

Assays for apoptosis in insect cells are disclosed by: Clem et al., "Prevention of apoptosis by a baculovirus gene during infection of insect cells", *Science* 254:1388–90, 1991; Crook et al., "An apoptosis-inhibiting baculovirus gene with a zinc finger-like motif," *J. Virol.* 67:2168–74, 1993; Rabizadeh et al., "Expression of the baculovirus p35 gene inhibits mammalian neural cell death", *J. Neurochem.* 61:2318–21, 1993; Birnbaum et al., "An apoptosis-inhibiting gene from a nuclear polyhedrosis virus encoding a polypeptide with Cys/His sequence motifs", *J. Virol.* 68:2521–8, 1994; Clem et al., *Mol. Cell. Biol.* 14:5212–5222, 1994.

XVII. Construction of a Transgenic Animal.

Characterization of NAIP genes provides information that is necessary for a NAIP knockout animal model to be developed by homologous recombination. Preferably, the model is a mammalian animal, most preferably a mouse. Similarly, an animal model of NAIP overproduction may be generated by integrating one or more NAIP sequences into the genome, according to standard transgenic techniques.

A replacement-type targeting vector, which would be used to create a knockout model, can be constructed using an isogenic genomic clone, for example, from a mouse strain such as 129/Sv (Stratagene Inc., La Jolla, Calif.). The targeting vector will be introduced into a suitably derived line of embryonic stem (ES) cells by electroporation to generate ES cell lines that carry a profoundly truncated form of a NAIP. To generate chimeric founder mice, the targeted cell lines will be injected into a mouse blastula stage embryo. Heterozygous offspring will be interbred to homozygosity. Knockout mice would provide the means, in vivo, to screen for therapeutic compounds that modulate apoptosis via a NAIP-dependent pathway. Making such mice may require use of loxP sites due to the multiple copies of NAIP on the chromosome (see Sauer and Henderson, *Nucleic Aids Res.* 17: 147–61 (1989)).

EXAMPLES

The examples are meant to illustrate, not limit the invention.

Example 1

Expression of NAIP in Rat-1, CHO, and HeLa Pooled Stable Lines and Adenovirus Infected Cells Analysed by Western Blotting and Immunofluorescence To generate nearly 3.7 kb NAIP construct tagged with the myc epitope (I) MTG-SP3.7, a 2.5 kb Bsu36I/SalI fragment of NAIP cloned into BLUESCRIPT (cloning vector) and (ii) Bsu36I/XhoI cut MTG-SE1.7, the expression vector pcDNA3 containing a 300 bp myc epitope and a 1.7 kb fragment of NAIP were ligated. HeLa, CHO, and Rat-1 cells were transfected by lipofection (Gibco BRL) with 8 μg DNA and G418 resistant transformants were selected by maintaining the cells in 250 μg/ml, 400 μg/ml, and 800 μg/ml G418 respectively. All cells were maintained in Eagles medium containing 10% fetal calf serum. For construction of the adenovirus, a 3.7 kb BamHI fragment of NAIP was cloned into the SwaI site of the adenovirus expression cosmid pAdex1CAwt. Production of vectors, purification by double cesium chloride gradient and titer determination was as described in Rosenfeld, M. A. et al. 1992, and Graham, F. L. and Van Der Eb, A. 1973.

Western blot analysis was performed using mouse anti-human myc monoclonal antibody (Ellison, M. J. and Hochstrasser, M. J. 1991) or rabbit anti-human NAIP (E1.0) polyclonal antibody. For NAIP antibody production, rabbits were immunized with purified bacterial produced fusion protein in complete Freunds adjuvant. Serum was precleared with GST protein and anti-NAIP immunoglobin purified with immobilized GST-NAIP fusion proteins.

For immunofluorescence, cells were grown on glass slides, fixed with formaldehyde for 10 minutes, incubated with anti-NAIP (1:200) or anti-myc (1:20) in PBS, 0.3% Triton X-100™ for 1 hour followed by incubation with secondary antisera, FITC-labeled donkey anti-rabbit immunoglobulin (Amersham), biotinylated goat anti-mouse immunoglobulin (Amersham), and streptavidin TEXAS-RED™ (fluorescently labeled streptavidin) (Amersham).

Example 2

The Effect of NAIP on Cell Death Induced by Serum Deprivation, Menadione, and TNF-α

For each assay cells were plated at $5 \times 10^4$ ml in triplicate. CHO or Rat-1 cells were treated with menadione for 1.5 hrs, washed 5 times in PBS, and maintained in normal media. For serum deprivation assays, cells were washed 5 times in PBS, and maintained in media with 0% fetal calf serum. HeLa cells were treated with 20 units/ml TNF-α in combination with 30 g/ml cyclohexamide for 17 hrs. Apoptosis was assayed for each trigger by propidium iodide staining. Adenovirus infected cells were subjected to triggers 36 hrs post infection. LacZ expression was confirmed histochemically by 5-bromo-4-chloro-3-indoyl-β-D-galactoside (X-gal) as described in Ellison, M. J. and Hochstrasser, M. J. 1991. Transcription of NAIP was determined by in situ hybridization using the DIG labeled sense oligonucleotide following the manufacturers protocol (Boehringer Mannheim). The human Bcl-2 clone pB4 (ATCC) was digested with EcoRI and ligated into the EcoRI site of pcDNA3.

For adenovirus assays an adenovirus encoding LacZ, antisense NAIP (NAIP) or vector alone with no insert were utilized as controls. Bcl-2 was utilized as a positive control and pcDNA alone as a negative control in cell line assays. Cell viability was determined by trypan blue exclusion. Data are presented as averages of three independently derived transfected pools or infections.

Example 3

Immunofluorescence Analysis of Human Spinal Cord Tissue

Human tissues were obtained at autopsy from a 2-month old infant that died of non-neurological causes and stored at −80° C. 14 μM cryostat sections were fixed in formaldehyde for 20 minutes, rinsed in PBS, and incubated in blocking solution (2% horse serum, 2% casien, 2% BSA in PBS) for 15 minutes prior to overnight incubation with anti-NAIP antisera diluted in this blocking solution. CY-3 labeled donkey anti-rabbit immunoglobulin (Sigma) was utilized as secondary antisera.

Example 4

Isolating and Cloning the NAIP Gene

PAC Contig Array.

The 40G1 CATT subloci demonstrated linkage disequilibrium and therefore a PAC contiguous array containing the CATT region was constructed. This PAC contig array comprised 9 clones and extended approximately 400 kb. Genetic analysis combined with the physical mapping data indicated that the 40G1 CATT subloci marker which showed the greatest disequilibrium with SMA was duplicated and was localized at the extreme centromeric of the critical SMA interval. Consequently the 154 kb PAC clone 125D9 which contained within 10 kb of its centromeric end the SMA interval defining CMS allele 9 and extended telemetrically to incorporate the 40G1 CATT sublocus was chosen for further examination.

Two genomic libraries were constructed by performing complete and partial (average insert size 5 kb) Sau3A1 on PAC125D9 and cloning the restricted products into BamH1 digested BLUESCRIPT (cloning vector) plasmids. Genomic sequencing was conducted on both termini of 200 clones from the 5 kb insert partial Sau3A1 library in the manner of (Chen et al., 1993) permitting the construction of contiguous and overlapping genomic clones covering most of the PAC. This proved instrumental in the elucidation of the neuronal apoptosis inhibitor protein gene structure.

PAC 125D9 is cleaved into 30 kb centromeric and 125 kb telomeric fragments by a NotI site (which was later shown to bisect exon 7 of the PAC 125D9 at the beginning of the apoptosis inhibitor domain. The NotI PAC fragments were isolated by preparative PFGE and used separately to probe fetal brain cDNA libraries. Physical mapping and sequencing of the NotI site region was also undertaken to assay for the presence of a CpG island, an approach which rapidly detected coding sequences. The PAC 125D9 was also used as a template in an exon trapping system resulting in the identification of the exons contained in the neuronal apoptosis inhibitor protein gene.

The multipronged approach, in addition to the presence of transcripts identified previously by hybridization by clones from the cosmid array (such as, GA1 and L7), resulted in the rapid identification of six cDNA clones contained in neuronal apoptosis inhibitor protein gene. The clones were arranged, where possible, into overlapping arrays. Chimerism was excluded on a number of occasions by detection of co-linearity of the cDNA clone termini with sequences from clones derived from the PAC 125D9 partial Sau3A1 genomic library.

Cloning of Neuronal Apoptosis Inhibitor Protein Gene.

A human fetal spinal cord cDNA library was probed with the entire genomic DNA insert of cosmid 250B6 containing one of the 5 CATT subloci. This resulted in a detection of a 2.2 kb transcript referred to as GA1. Further probings of fetal brain libraries with the contiguous cosmid inserts (cosmids 40G1) as well as single copy subclones isolated from such cosmids were undertaken. A number of transcripts were obtained including one termed L7. No coding region was detected for L7 probably due to the fact that a substantial portion of the clone contained unprocessed heteronuclear RNA. However, it was later discovered that L7 proved to comprise part of what is believed to be the neuronal apoptosis inhibitor protein gene. Similarly, the GA1 transcript ultimately proved to be exon 13 of the neuronal apoptosis inhibitor protein. Since GA1 was found to contain exons indicating that it was an expressed gene, it was of particular interest. The GA1 transcript which was contained within the PAC clone 125D9 was subsequently extended by further probing in cDNA libraries.

The remaining gaps in the cDNA were completed and the final 3' extension was achieved by probing a fetal brain library with two trapped exons. A physical map of the cDNA with overlapping clones was prepared. The entire cDNA sequence contains 18 exons (1 to 14a and 14 to 17). The amino acid sequence starts with methionine which corresponds to the nucleotide triplet ATG.

DNA Manipulation and Analysis.

Four genomic libraries containing PAC 125D9 insert were constructed by BamHI, BamHI/NotI, total and partial Sau3aI (selected for 5 kb insert size) digestions of the PAC genomic DNA insert and subcloned into BLUESCRIPT (cloning vector) vector. Sequencing of approximately 400 bp of both termini of 200 five kb clones from the partial Sau3AI digestion library in the manner of Chen et al. (1993) was undertaken.

Coding sequences from the PACs were isolated by the exon amplification procedure as described by Church et al. (1994). PACs were digested with BamHI or BamHI and BglII and subcloned into pSPL3. Pooled clones of each PAC were transfected into COS-1 cells. After a 24 h transfection total RNA was extracted. Exons were cloned into pAMP10 (Gibco, BRL) and sequenced utilizing primer SD2, (GTG AAC TGC ACT GTG ACA AGC TGC) SEQ ID NO: 25.

DNA sequencing was conducted on an ABI 373A automated DNA sequencer. Two commercial human fetal brain cDNA libraries in lambda gt (Stratagene) and lambda ZAP (Clontech) were used for candidate transcript isolation. The Northern blot was commercially acquired (Clontech) and probing was performed using standard methodology.

In general, primers used in the paper for PCR were selected for $T_m$s of 60° C. and can be used with the following conditions: 30 cycles of 94° C., 60s; 60° C., 60s; 72° C., 90s. PCR primer mappings are as referred to in the figure legends and text. Primer sequences are as follows:

```
1258  ATg CTT ggA TCT CTA gAA Tgg-SEQ ID NO: 3

1285  AgC AAA gAC ATg Tgg Cgg AA-SEQ ID NO: 4

1343  CCA gCT CCT AgA gAA AgA Agg A-SEQ ID NO: 5

1844  gAA CTA Cgg CTg gAC TCT TTT-SEQ ID NO: 6

1863  CTC TCA gCC TgC TCT TCA gAT-SEQ ID NO: 7

1864  AAA gCC TCT gAC gAg Agg ATC-SEQ ID NO: 8

1884  CgA CTg CCT gTT CAT CTA CgA-SEQ ID NO: 9

1886  TTT gTT CTC CAg CCA CAT ACT-SEQ ID NO: 10

1887  CAT TTg gCA TgT TCC TTC CAA g-SEQ ID NO: 11

1893  gTA gAT gAA TAC TgA TgT TTC ATA ATT-
      SEQ ID NO: 12

1910  TgC CAC TgC CAg gCA ATC TAA-SEQ ID NO: 13

1919  TAA ACA ggA CAC ggT ACA gTg-SEQ ID NO: 14

1923  CAT gTT TTA AgT CTC ggT gCT CTg-SEQ ID NO: 15

1926  TTA gCC AgA TgT gTT ggC ACA Tg-SEQ ID NO: 16

1927  gAT TCT ATg TgA TAg gCA gCC A-SEQ ID NO: 17

1933  gCC ACT gCT CCC gAT ggA TTA-SEQ ID NO: 18

1974  gCT CTC AgC TgC TCA TTC AgA T-SEQ ID NO: 19

1979  ACA AAg TTC ACC ACg gCT CTg-SEQ ID NO: 20
```

Figure 4:
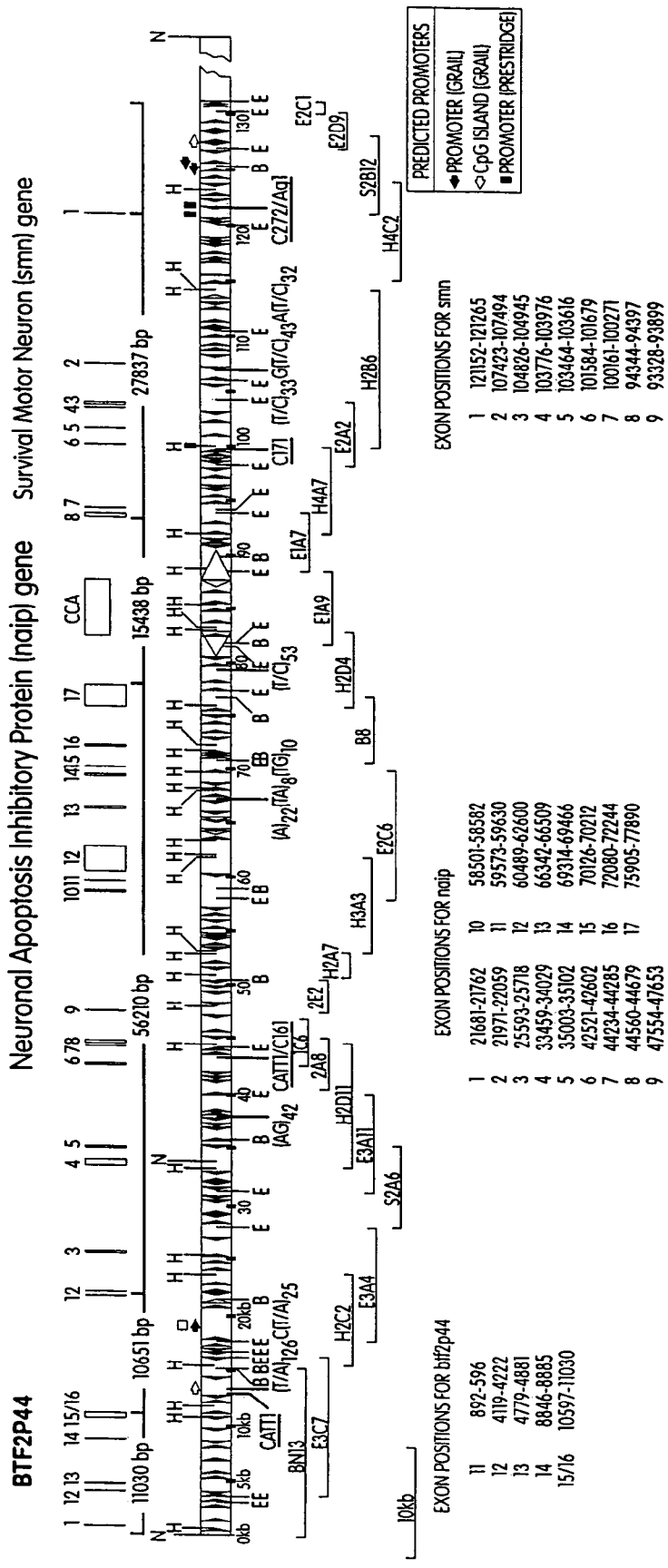
FIG. 4 depicts the genomic structure of PAC 125D9 from human chromosome 5q13.1. Both strands of the 131,708 bp region shown in the figure have been sequenced and can be found as GenBank accession #U80017. NotI (N), EcoRI (E), HindIII (H), and BamHI (B) sites are indicated. The exons of BTF2p44, NAIP, and SMN are bracketed. The transcribed (but not translated) CCA sequence is indicated by the box. The number of nucleotides which a specific region spans is as indicated, e.g., the gap between NAIP and SMN is 15471 bp. The minimal tiling pattern of plasmid clones covering the PAC is shown below. The letters at the beginning of each clone indicate the restriction enzymes used for preparing the plasmid libraries, except for 1C6, 2A8, and 2E2 which are clones from the partial Sau3AI libraries. (SstI-S). The location and orientation of eight classes of repeat sequences found using the NIH Sequin program are depicted by triangles. Promotor sequences as detected by GRAIL (filled arrows) or Prestridge (Prestige, D. S. *J. Mol. Biol.* 249, 923–932 (1995) (filled block) programs and CpG islands (unfilled arrows) are shown as arrows or blocks above the bar.

Our genetic and mapping analysis of SMA has led to the identification of the 154 kb insert of PAC125D9 as the likely site of the SMA gene. We report here the complete DNA sequence of the 131 kb portion of the PAC125D9 insert which contains both NAIP and SMN$^{tel}$ as well as the 3' end of a copy of the Basic Transcription Factor gene BTF2p44. PAC125D9 insert digested with a variety of restriction enzymes was used to generate nine libraries. Shotgun sequencing of clones from the Sau3A1 library was hampered by the Alu rich nature of the area, sequencing was therefore conducted by a modified transposon based approach yielding the configuration depicted in the figure. The NAIP and SMN$^{tel}$ genes, separated by 15.5 kb, are in a tail to tail (5'--22 3':3'>-- 5') orientation, spanning 56 kb, and 28 kb of genomic DNA, respectively. The gene BTF2p44 exists in a number of copies on 5q13.1; exons 11–16 of one BTF2P44 copy occupy the most 5' eleven kb of the PAC insert followed by an 11 kb interval before NAIP exon 2. The first NAIP exon as originally reported is not present in this PAC and may have been a heteronuclear artifact. An approximately 3 kb section of the 15.5 kb interval between NAIP and SMN (CCA, FIG. 4) is transcribed but contains no protein coding sequence. Indeed, no coding sequence in addition to BTF2P44, NAIP, and SMN was identified throughout the entire interval.

CpG islands were identified in the 5' region of both SMN and NAIP genes. One hundred and forty five Alu sequences were identified in the 131 kb sequence, with five clusters of high density seen (figure legend). Such Alu density associated with L1 paucity (five copies) is in keeping with previous findings for light Giemsa staining (or reverse) chromosomal bands. Copies of other repeats (e.g., MIR2, MST, and MER) as detected by Sequin program are also as depicted. The polymorphic microsatellite loci previously mapped to the SMA region; (CMS1, CATT, C161, C171, C272, or AG-1) as well as unusual single and di-nucleotide repeats are as shown.

The full length NAIP cDNA (6228 bp with an ORF of 4212 bp) was also elucidated by cDNA sequencing and comparison with PAC sequence, comprising 17 exons encoding a predicted 156 kDa protein of 1403 amino acids (data not shown). A novel NAIP exon 14 between the original exon 14 and 15 was identified. The original exon 17 has been replaced by a novel exon, which contains the stop codon, a 1.6 kb 3'UTR region, and the polyadenylation consensus site (AATAAA) identified by 3' RACE. No new protein domains are found in the NAIP gene.

A rigorous definition of how far deletions extend on type 1 SMA chromosomes is central to our understanding of disease pathogenesis. If the genotype most frequently observed on type 1 SMA chromosomes (i.e. absence of NAIP exons 4 and 5 as well as $SMN^{tel}$ exons 7 and 8) are the result of a single event, then our sequencing suggests a minimal deletion size of 60 kb. The high deletion frequency on type 1 SMA chromosomes of the CATT-40G1, (which maps between NAIP exon 7 and 8) is consistent with such a deletion.

Southern blots containing genomic DNA probed with NAIP cDNA reveal a diversity of bands, a result of the polymorphic number of variant forms of this locus mapping to 5q13.1. In contrast, the same blots probed with SMN cDNA reveals only the bands associated with the intact SMN locus, for SMA and non-SMA individuals alike. Thus, there is no evidence of truncated or partially deleted SMN genes such as seen with the NAIP gene. The absence of any detectable SMN junction fragment in SMA patients strongly suggests that the $SMN^{tel}$ exon 7 and 8 deletion detected in the significant majority of SMA cases incorporates the entire $SMN^{tel}$ gene, thus extending the putative minimal SMA type 1 deletion to approximately 100 kb. This is in keeping with the high deletion frequency of C272 (or AG-1) microsatellite (which maps to SMN exon 1) on type 1 SMA chromosomes. A 15% deletion frequency of one copy of BTF2P44 is observed in all SMA cases irrespective of clinical severity, suggesting that this mutation may not be an extension of the putative SMN-NAIP deletion. Clarification of this issue must await details of which copy of p44 is deleted.

Our sequencing of PAC125D9 maps the intact NAIP locus and clinically relevant $SMN^{tel}$ to a 100 kb region which contains those microsatellite polymorphisms that are preferentially deleted on the significant majority of type 1 SMA chromosomes (i.e. CATT-40G1, C272, or AG-1). The absence of any protein coding sequence, other than NAIP and SMN in this interval, focuses attention on these two genes as the key modulators of type 1 SMA. One potential pathogenic model is that $SMN^{tel}$ absence acts as the primary neurotoxic insult with NAIP depletion/absence leading to an attenuated apoptotic resistance, exacerbating motor neuron attrition. Presence of additional $SMN^{cen}$ may also act to modulate the course of the disease. In addition to aiding in our comprehension of the molecular pathology of acute SMA, the sequence presented here should help in the study of transcriptional control elements for both genes, possibly facilitating the formulation of genetic therapies for this devastating neuromuscular disease.

DNA Sequencing.

Partial Sau3A1 (selected for 3–5kb) BamHI, EcoRI, HindIII, PstI, SstI, XbaI, and EcoRV libraries) were made from the PAC125D9 insert and sequenced using a transposon-based methodology (TN1000 Gold Biotechnology). Subcloning of a large number of inserts into the commercially supplied pMOB plasmid was found to be problematic, therefore pUC18 and pBLUESCRIPT (cloning vector) SK were used. In general, fewer than 10% of clones had transposons in the vector region. E. coli lysate was employed as sequencing template using our modified heat soaked protocol. Sequencing was from the TN1000 transposon randomly inserted into the target DNA, using primers of opposite orientation (5'-ATA TAA ACA ACGAAT TAT CTC C-3' (SEQ ID NO: 26); 5'-GTA TTA TAA TCA ATA AGTTAT ACC-3') (SEQ ID NO: 27), generating approximately 1 kb of sequence with a 5 bp overlap, easily spanning 300 bp Alu repeats. Our approach permitted sequencing of inserts as large as 14 kb.

As the SMA region is known to be unstable, special care to ensure an intact, unaltered PAC insert was undertaken primarily by comparison of PAC125D9 insert and genomic DNA hybridization patterns on Southern blots.

Raw DNA sequence data generated by our automated sequencers (ABI 373 and ABI 373A) were processed and assembled in parallel by the Sequencher 3.0 program (Gene Codes Inc.); and the GAP4 program from the Staden package. The edited results were automatically converted into GCG file formats and placed in a separate database for searches by outside users using our e-mail server at smafasta@mgcheo.med.uottawa.ca. GRAIL and Blast searches were employed to screen for protein coding sequence and the PROSITE Protein database was used to search for protein domains.

Example 5

NAIP Expression Vectors

Using the identified NAIP sequence information, a full length 3.7 kb NAIP construct tagged with the myc epitope (I) MTG-SP3.7, a 2.5 kb Bsu36I/SalI fragment of NAIP cloned into BLUESCRIPT (cloning vector) and (ii) Bsu36I/XhoI cut MTG-SEI.7, the expression vector pcDNA3 containing a 300 bp myc epitope and a 1.7 kb fragment of NAIP were ligated. HeLa, CHO, and Rat-1 cells were transfected by lipofection (Gibco BRL) with 8 µg DNA and G418 resistant transformants were selected by maintaining the cells in 250 µg/ml, 400 µg/ml, and 800 µg/ml G418 respectively.

Figure 1B:
Figure 1C:
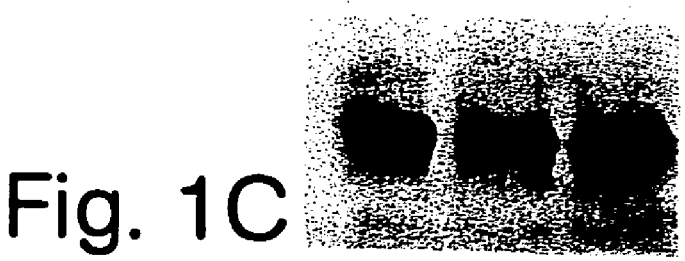
Figure 1D:
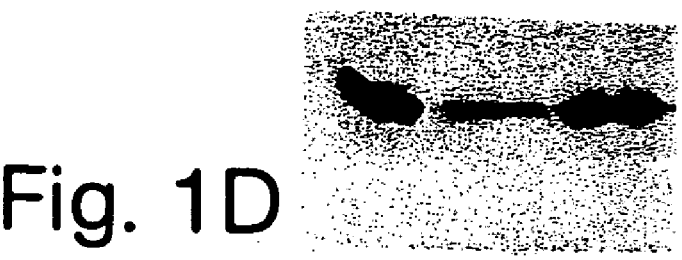
Figure 1E:
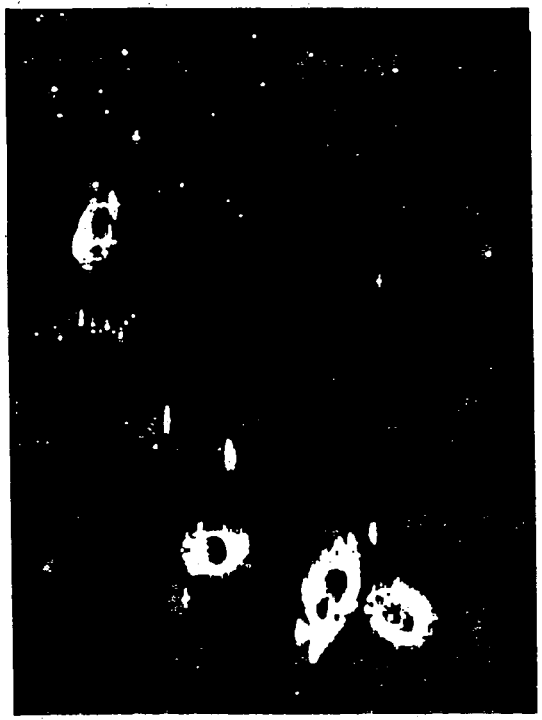
Figure 1F:
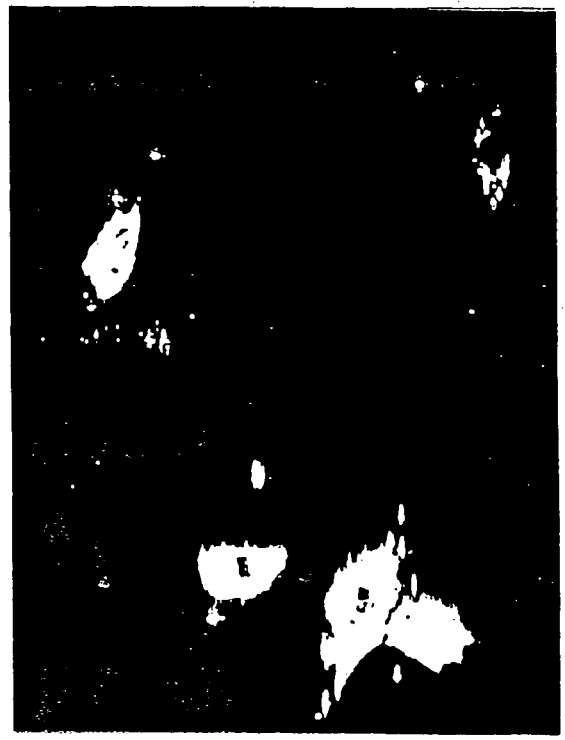
Figure 2A:
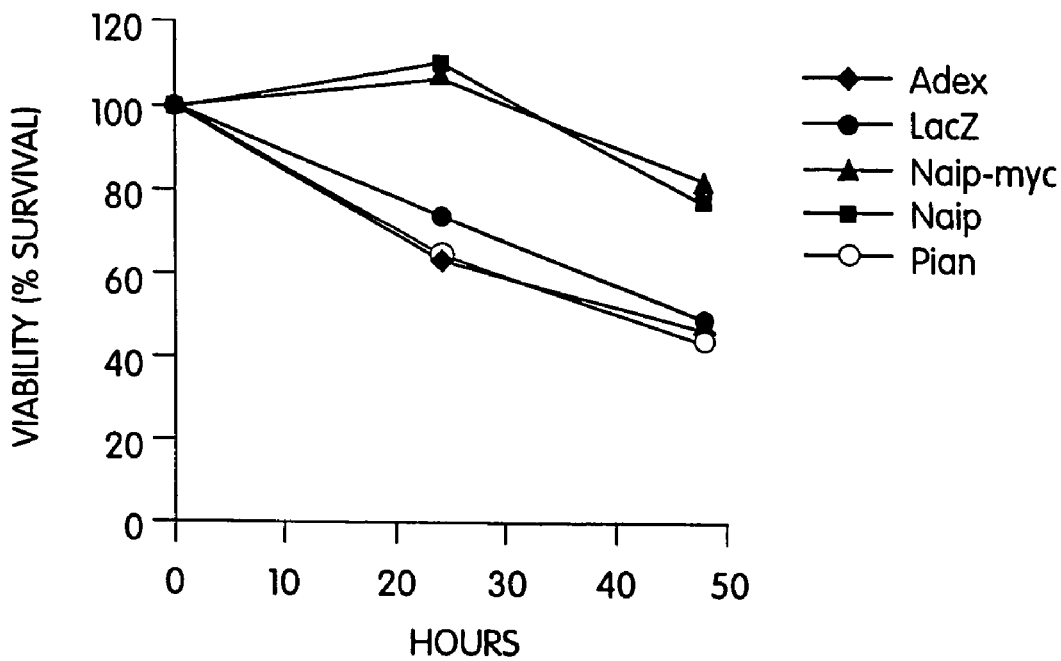
FIGS. 2A–J show the effect of NAIP on cell death induced by serum deprivation, menadione and TNF-α.
Figure 2B:
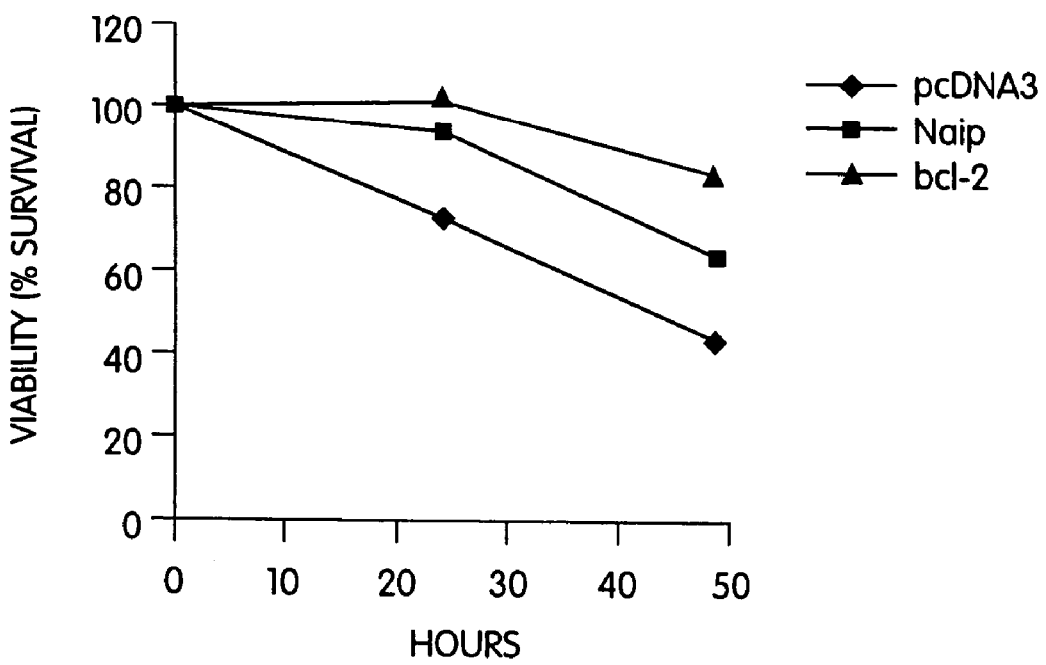
Figure 2C:
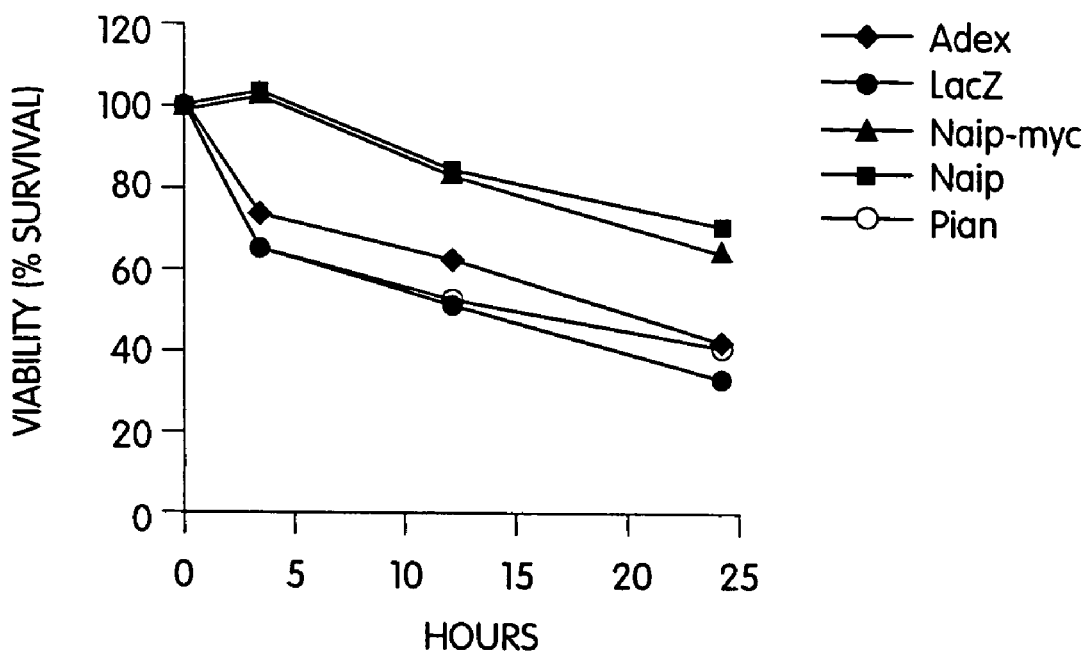
Figure 2D:
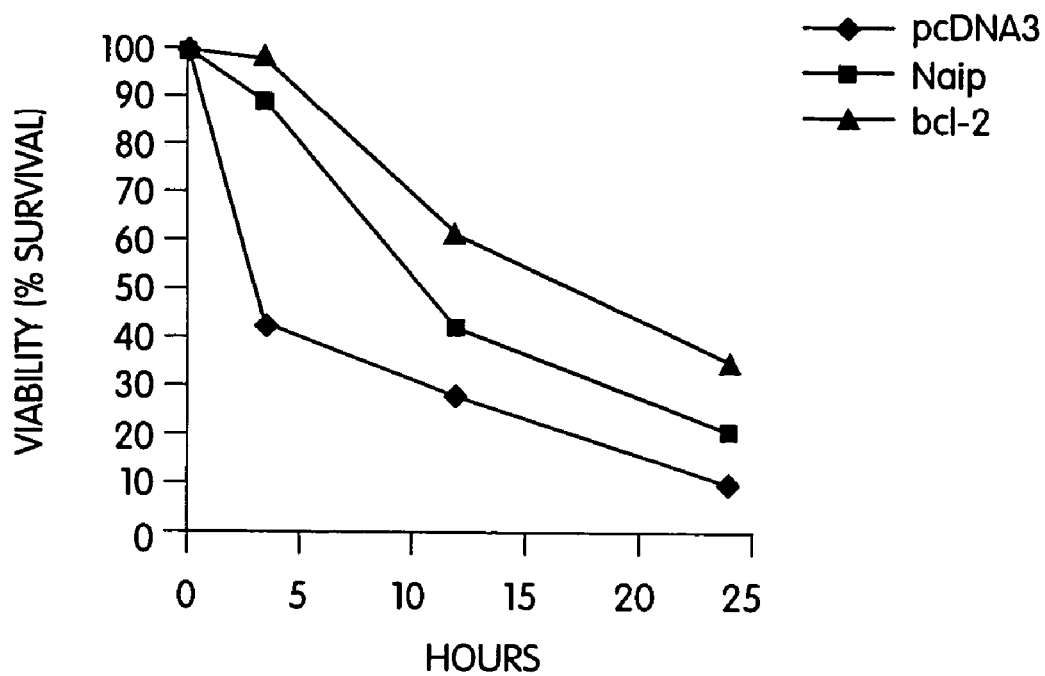
Figure 2E:
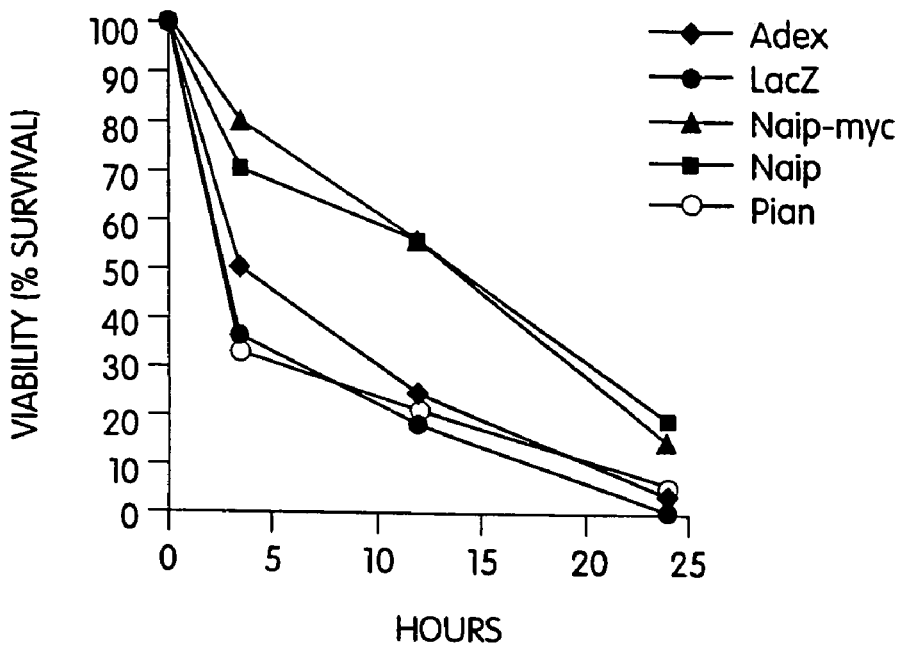
Figure 2F:
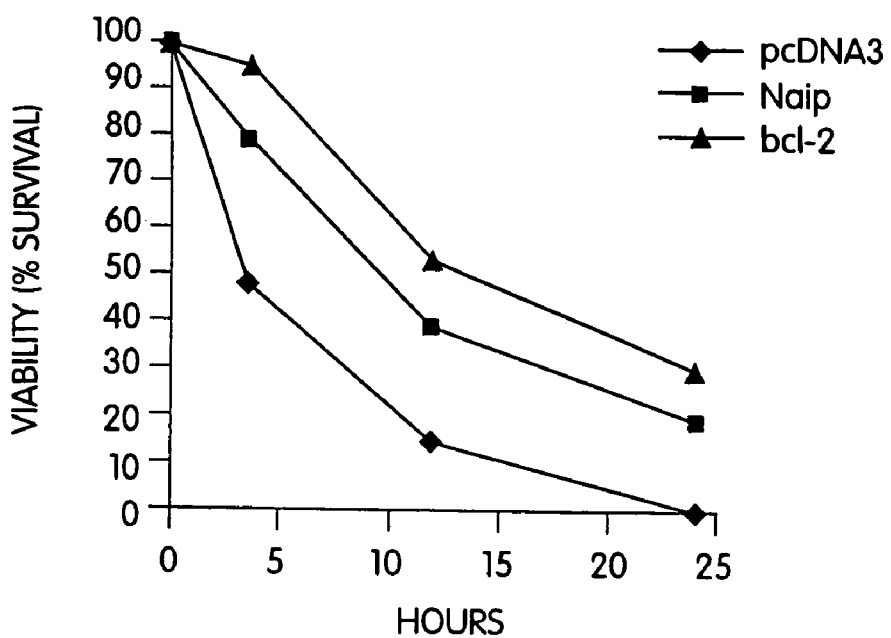
Figure 2G:
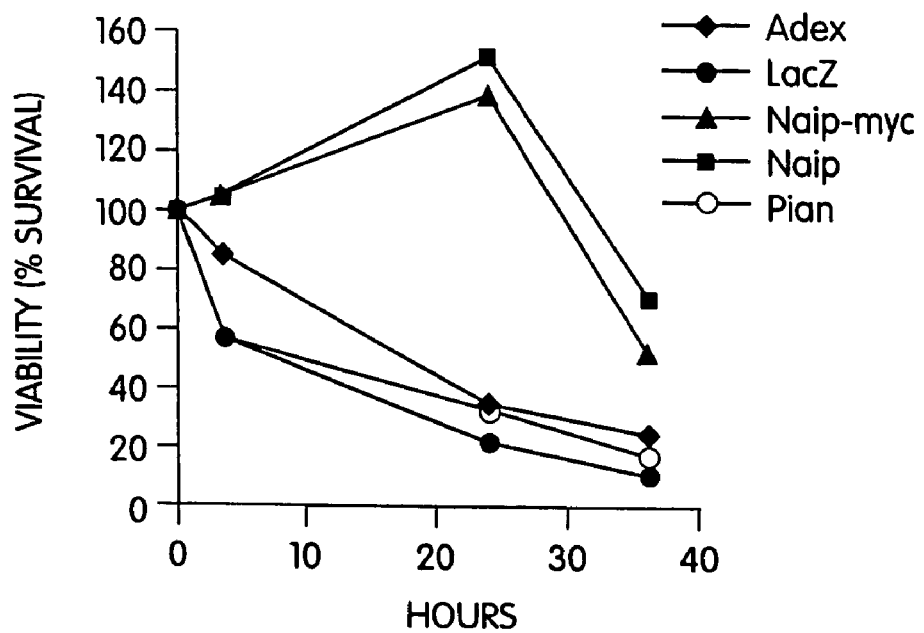
Figure 2H:
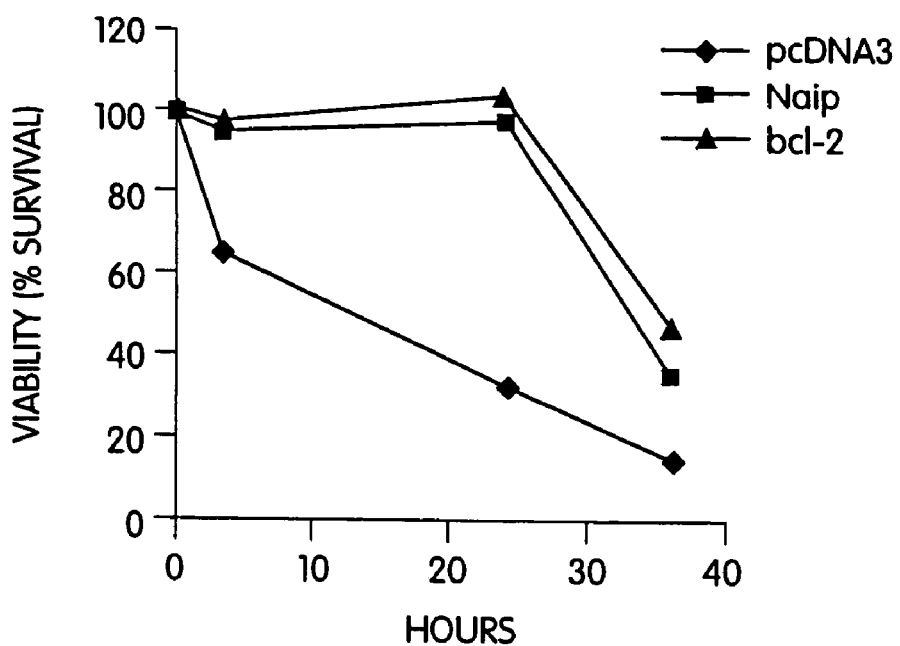
Figure 2I:
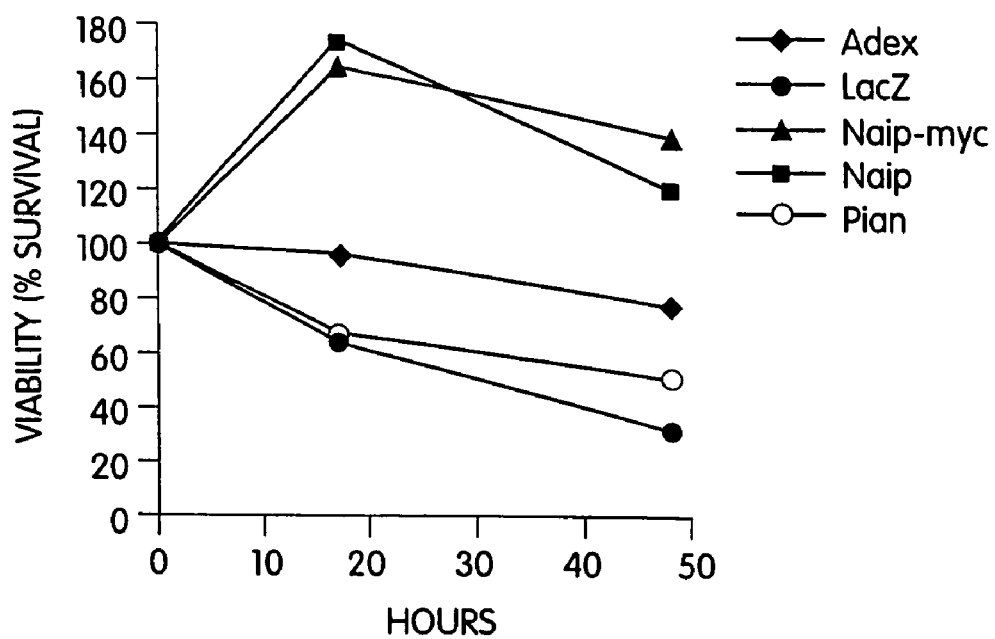
Figure 2J:
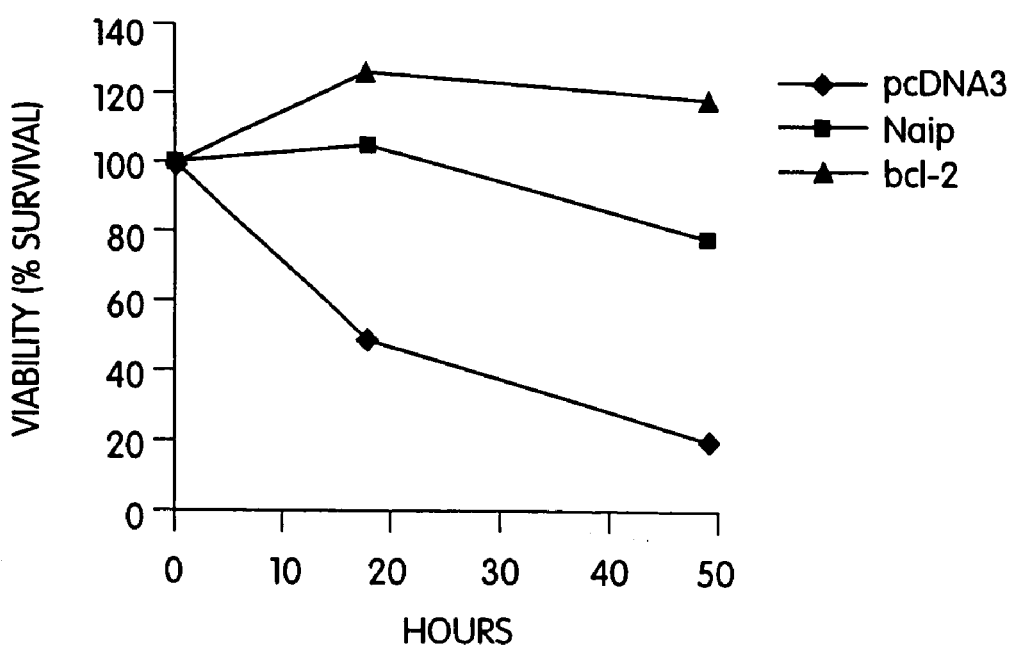

In a second approach, cells were infected with adenovirus alone or adenovirus expressing NAIP, antisense NAIP, or LacZ. For construction of the adenovirus, a 3.7 kb BamHI fragment of NAIP was cloned into the SwaI site of the adenovirus expression cosmid pAdex1CAwt. The antisense NAIP RNA contains a sequence complementary to the region of an mRNA containing an initiator codon. Expression of NAIP was confirmed in both procedures by Western blot analysis and immunofluorescence. Following infection with the recombinant adenoviruses, CHO cells were induced to undergo apoptosis by serum deprivation with survival rates of 48% (no insert), 51% (LacZ), and 45% (antisense NAIP) at 48 hours (FIG. 1A). In contrast, CHO cells infected with adenovirus expressing NAIP demonstrate 78–83% survival. NAIP also induced survival in stably transfected CHO pools, albeit slightly less than that seen in adenovirus infected cells: 44% of the vector transfectants and 65% of the NAIP transfectants survived at 48 hours (FIG. 1B). Next, overexpression of NAIP in CHO cells treated with 20 µM menadione (a potent inducer of free radicals) resulted in 20–30% enhancement of survival compared with controls after 24 hours (FIGS. 1C–D). Overexpression of NAIP also protected menadione treated Rat-1 fibroblasts from undergoing cell death (FIGS. 1E–F and 1G–H). Only 15% of cells infected with LacZ expressing adenovirus were viable at 12 hours in contrast to 80% of NAIP infected cells, an effect also detected with the pooled Rat-1 NAIP transfectants. Even greater survival was induced by NAIP overexpression at a lower menadione concentration (5 µM), with 98% of pooled NAIP transfectants and 33% of control transfectants viable at 24 hours (FIGS. 1G–H). Also assessed was the protective effect of NAIP on cells exposed to the cytokine TNF-$\alpha$. HeLa cells treated with TNF-$\alpha$ and cyclohexamide were protected from apoptosis when infected with adenovirus expressing high levels of NAIP (139%) at 48 hours, an effect not observed with antisense NAIP (52%) (FIGS. 1I–J). A similar effect was observed in pooled HeLa transformants.

To confirm that cells surviving the apoptotic agents expressed NAIP, immunofluorescence with anti-NAIP antisera was performed on a number of the cell death assays. Immunofluorescence is a technique that localizes proteins within a cell by light microscopy by the use of antibodies specific for a desired protein and a fluorescence microscope. Dyes can be chemically coupled to antibodies directed against purified antibodies specific for a desired protein. This fluorescent dye-antibody complex when added to permeabilized cells or tissue sections binds to the desired antigen-antibody, which lights up when illuminated by the exciting wavelength. Fluorescent antibodies may also be microinjected into cultured cells for visualization. Using immunofluorescence, CY-3, a dye which emits red light, was coupled to a secondary antibody used to detect the bound anti-NAIP antibodies. A dramatic enrichment of NAIP expressing cells was observed, with no alteration noted in the cytoplasmic distribution of NAIP. These data offer strong support for the apoptotic suppression activity of NAIP.

Example 6

Cellular Distribution of NAIP using NAIP Antibodies

It was previously demonstrated (Roy, et al. "The gene for NAIP, a novel protein with homology to baculoviral inhibitor of apoptosis, is partially deleted in individuals with spinal muscle atrophy," Cell 80: 167–178 (1995)) by reverse transcriptase PCR analysis that the NAIP transcript is present in human spinal cord. To define more precisely the cellular distribution of NAIP, a polyclonal antiserum was raised against NAIP. The NAIP antibodies were then used in both immunocytochemistry and immunofluorescence techniques to visualize the protein directly in cells and tissues in order to establish the subcellular location and tissue specificity of the protein.

Figure 3A:
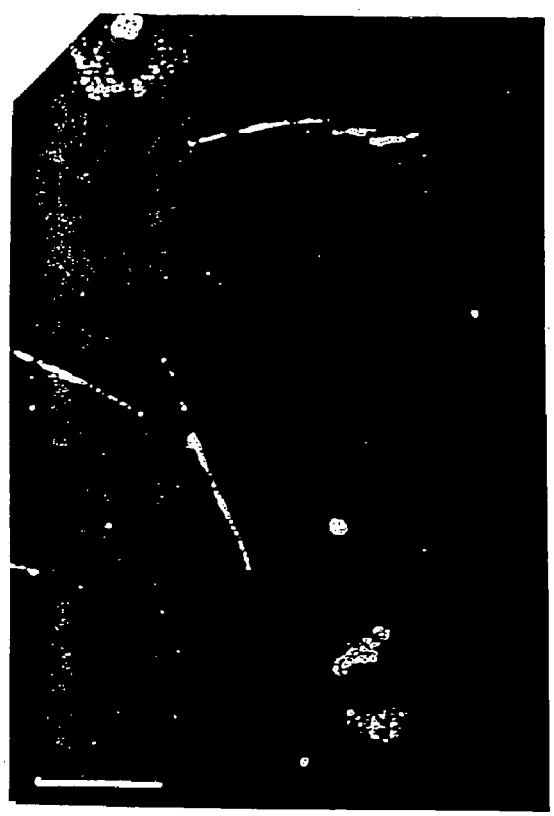
FIGS. 3A–D show immunofluorescence analysis of human spinal cord tissue.
Figure 3B:
Figure 3C:
Figure 3D:
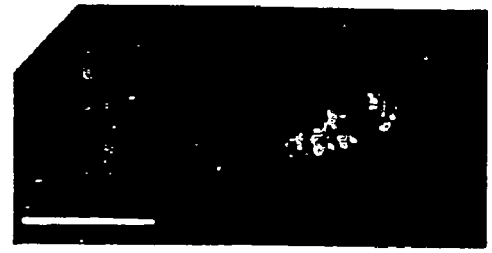

The ability of the polyclonal antibody to detect NAIP was confirmed by immunofluorescence of cells transfected with myc tagged NAIP employed both the anti-NAIP and anti-Myc antibodies, as well as western blot analysis on protein extracts of these cells (FIGS. 1A–F). In the Western blotting technique, proteins are run on polyacrylamide gel and then transferred onto nitrocellulose membranes. These membranes are then incubated in the presence of the antibody (primary), then following washing are incubated to a secondary antibody which is used for detection of the protein-primary antibody complex. Following repeated washing, the entire complex is visualized using calorimetric or chemiluminescent methods. A protein of the expected molecular weight was detected by both antibodies in western blots and their cellular co-localization demonstrated by immunofluorescence. Sections of human spinal cord stained with anti-NAIP showed strong immunoreactivity in the cytoplasm of the anterior horn cells and intermediolateral neurons (FIGS. 3A–B). Consistent with the motor neuron staining, NAIP reactivity was observed in the ventral roots which contain motor axons but not the dorsal roots comprised of sensory axons (FIGS. 3C–D). The observation of motor neuron staining correlates well with a role for the protein in the pathogenesis of SMA. However, the presence of NAIP in intermediolateral neurons which are not reported to be affected in SMA, implies heterogeneity in the apoptotic pathways between the two classes of neurons.

OTHER EMBODIMENTS

In other embodiments, the invention includes any protein which is substantially identical to a mammalian NAIP polypeptides provided in FIGS. 6A–I and 7A–L, SEQ ID NOs: 22 and 24); such homologs include other substantially pure naturally-occurring mammalian NAIP proteins as well as allelic variants; natural mutants; induced mutants; DNA sequences which encode proteins and also hybridize to the NAIP DNA sequences of FIGS. 6A–I and 7A–L, (SEQ ID NOs: 21 and 23) under high stringency conditions, or less preferably, under low stringency conditions (e.g., washing at 2×SSC at 40° C. with a probe length of at least 40 nucleotides); and proteins specifically bound by antisera directed to a NAIP polypeptide. The term also includes chimeric polypeptides that include a NAIP portion. The sequence of SEQ ID NO: 1 and the IAP proteins are specifically excluded.

The invention further includes analogs of any naturally occurring NAIP polypeptide. Analogs can differ from the naturally occurring NAIP protein by amino acid sequence differences, by post-translational modifications, or by both. Analogs of the invention will generally exhibit at least 85%, more preferably 90%, and most preferably 95% or even 99% identity with all or part of a naturally occurring NAIP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring NAIP polypeptide by alterations in primary sequence. These include genetic variants, both natural and induced (e.g., resulting from random mutagenesis by irradiation or exposure to ethanemethylsulfate or by site-specific mutagenesis as described in Sambrook, Fritsch, and Maniatis, Molecular Cloning: A Laboratory Manual (2nd Ed.), CSH Press, 1989, or Ausubel et al., supra). Also included are cyclized peptides, molecules, and analogs that contain residues other than L-amino acids, e.g., D-amino acids or non-naturally occurring or synthetic amino acids, e.g., B or y amino acids. In addition to full-length polypeptides, the invention also includes NAIP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of NAIP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those that facilitate specific detection of a NAIP nucleic acid or amino acid sequence in a sample to be diagnosed.

What is claimed is:

1. A method of detecting the expression of NAIP in a cell or tissue sample comprising:
   (a) providing a cell sample or tissue sample;
   (b) incubating said cell or tissue sample with a purified antibody or an antigen binding fragment thereof that binds specifically to a portion of human NAIP protein, wherein said human NAIP protein is encoded by SEQ ID NO: 23 and wherein said antibody binds specifically to a portion of said human NAIP protein, said portion is encoded by nucleotides 3838–3990 of SEQ ID NO: 23 or nucleotides 4243–4605 of SEQ ID NO: 23; and
   (c) detecting binding of said antibody to said cell or tissue sample.

2. The method of claim 1, wherein said antibody is a polyclonal or monoclonal antibody.

3. The method of claim 1, wherein said antibody is an antigen binding genetically engineered antibody, humanized antibody, or a fragment thereof.

4. The method of claim 3, wherein said fragment is an F(ab')$_2$, Fab', Fv, or sFv fragment.

5. A method of detecting a NAIP polypeptide in a cell sample or tissue sample comprising:
   (a) providing a cell or tissue sample;
   (b) incubating said cell or tissue sample with a purified antibody that binds specifically to a portion of human NAIP protein, said portion encoded by nucleotides 3838–3990 of SEQ ID NO: 23 or nucleotides 4243–4605 of SEQ ID NO: 23; and
   (c) detecting binding of said antibody to said cell or tissue sample.

6. The method of claim 5, wherein said antibody is a polyclonal or monoclonal antibody.

7. The method of claim 5, wherein said antibody is an antigen binding genetically engineered antibody, humanized antibody, or a fragment thereof.

8. The method of claim 7, wherein said fragment is an F(ab')$_2$, Fab', Fv, or sFv fragment.

* * * * *

SEQUENCE LISTING

<160> NUMBER OF SEQ ID NOS: 27

<210> SEQ ID NO 1
<211> LENGTH: 5504
<212> TYPE: DNA
<213> ORGANISM: Homo sapiens

<400> SEQUENCE: 1

```
ttccggctgg acgttgccct gtgtacctct tcgactgcct gttcatctac gacgaacccc      60
gggtattgac cccagacaac aatgccactt catattgcat gaagacaaaa ggtcctgtgc     120
tcacctggga cccttctgga cgttgccctg tgttcctctt cgcctgcctg ttcatctacg     180
acgaaccccg ggtattgacc ccagacaaca atgccactta atattgggga cttcgtctgg     240
gattccaagg tgcattcatt gcaaagttcc ttaaatattt tctcactgct tcctactaaa     300
ggacggacag agcatttgtt cttcagccac atactttcct tccactggcc agcattctcc     360
tctattagac tagaactgtg gataaacctc agaaaatggc cacccagcag aaagcctctg     420
acgagaggat ctcccagttt gatcacaatt tgctgccaga gctgtctgct cttctgggcc     480
tagatgcagt tcagttggca aaggaactag aagaagagga gcagaaggag cgagcaaaaa     540
tgcagaaagg ctacaactct caaatgcgca gtgaagcaaa aaggttaaag acttttgtga     600
cttatgagcc gtacagctca tggataccac aggagatggc ggccgctggg ttttacttca     660
ctggggtaaa atctgggatt cagtgcttct gctgtagcct aatcctcttt ggtgccggcc     720
tcacgagact ccccatagaa gaccacaaga ggtttcatcc agattgtggg ttccttttga     780
acaaggatgt tggtaacatt gccaagtacg acataagggg gaagaatctg aagagcaggc     840
tgagaggagg taaaatgagg taccaagaag aggaggctag acttgcatcc ttcaggaact     900 ggccattta tgtccaaggg atatcccctt gtgtgctctc agaggctggc tttgtcttta     960
caggtaaaca ggacacggta cagtgttttt cctgtggtgg atgtttagga aattgggaag    1020
aaggagatga tccttggaag gaacatgcca aatggttccc caaatgtgaa tttcttcgga    1080
gtaagaaatc ctcagaggaa attacccagt atattcaaag ctacaaggga tttgttgaca    1140
taacgggaga acattttgtg aattcctggg tccagagaga attacctatg gcatcagctt    1200
attgcaatga cagcatcttt gcttacgaag aactacggct ggactctttt aaggactggc    1260
cccgggaatc agctgtggga gttgcagcac tggccaaagc aggtctttc tacacaggta    1320 taaaggacat cgtccagtgc ttttcctgtg gagggtgttt agagaaatgg caggaaggtg    1380
atgacccatt agacgatcac accagatgtt tcccaattg tccatttctc caaaatatga    1440
agtcctctgc ggaagtgact ccagaccttc agagccgtgt tgaactttgt gaattactgg    1500
aaaccacaag tgaaagcaat cttgaagatt caatagcagt tggtcctata gtgccagaaa    1560
```

-continued

```
tggcacaggg tgaagcccag tggtttcaag aggcaaagaa tctgaatgag cagctgagag   1620
cagcttatac cagcgccagt ttccgccaca tgtctttgct tgatatctct tccgatctgg   1680
ccacggacca cttgctgggc tgtgatctgt ctattgcttc aaaacacatc agcaaacctg   1740
tgcaagaacc tctggtgctg cctgaggtct ttggcaactt gaactctgtc atgtgtgtgg   1800
agggtgaagc tggaagtgga aagacggtcc tcctgaagaa aatagctttt ctgtgggcat   1860
ctggatgctg tccctgtta aacaggttcc agctggtttt ctacctctcc cttagttcca   1920
ccagaccaga cgaggggctg gccagtatca tctgtgacca gctcctagag aaagaaggat   1980
ctgttactga aatgtgcatg aggaacatta tccagcagtt aaagaatcag gtcttattcc   2040
ttttagatga ctacaaagaa atatgttcaa tccctcaagt cataggaaaa ctgattcaaa   2100
aaaaccactt atcccggacc tgcctattga ttgctgtccg tacaaacagg gccagggaca   2160
tccgccgata cctagagacc attctagaga tccaagcatt tcccttttat aatactgtct   2220
gtatattacg gaagctcttt tcacataata tgactcgtct gcgaaagttt atggtttact   2280
ttggaaagaa ccaaagtttg cagaagatac agaaaactcc tctctttgtg gcggcgatct   2340
gtgctcattg gtttcagtat ccttttgacc catcctttga tgatgtggct gttttcaagt   2400
cctatatgga acgcctttcc ttaaggaaca aagcgacagc tgaaattctc aaagcaactg   2460
tgtcctcctg tggtgagctg gccttgaaag ggtttttttc atgttgcttt gagtttaatg   2520
atgatgatct cgcagaagca ggggttgatg aagatgaaga tctaaccatg tgcttgatga   2580
gcaaatttac agcccagaga ctaagaccat tctaccggtt tttaagtcct gccttccaag   2640
aatttcttgc ggggatgagg ctgattgaac tcctggattc agataggcag gaacatcaag   2700
atttgggact gtatcatttg aaacaaatca actcacccat gatgactgta agcgcctaca   2760 acaattttt gaactatgtc tccagcctcc cttcaacaaa gcagggccc aaaattgtgt   2820 ctcatttgct ccattagtg gataacaaag agtcattgga gaatatatct gaaaatgatg   2880
actacttaaa gcaccagcca gaaatttcac tgcagatgca gttacttagg ggattgtggc   2940
aaatttgtcc acaagcttac ttttcaatgg tttcagaaca tttactgtt cttgccctga   3000 aaactgctta tcaaagcaac actgttgctg cgtgttctcc atttgttttg caattccttc   3060
aagggagaac actgactttg ggtgcgctta acttacagta ctttttcgac cacccagaaa   3120
gcttgtcatt gttgaggagc atccacttct caatacgagg aaataagaca tcacccagag   3180 cacattttc agttctggaa acatgttttg acaaatcaca ggtgccaact atagatcagg   3240
actatgcttc tgcctttgaa cctatgaatg aatgggagcg aaatttagct gaaaaagagg   3300
ataatgtaaa gagctatatg gatatgcagc gcagggcatc accagacctt agtactggct   3360 attggaaaact ttctccaaag cagtacaaga ttccctgtct agaagtcgat gtgaatgata   3420
ttgatgttgt aggccaggat atgcttgaga ttctaatgac agttttctca gcttcacagc   3480
gcatcgaact ccatttaaac cacagcagag gctttatga aagcatccgc ccagctcttg   3540
agctgtctaa ggcctctgtc accaagtgct ccataagcaa gttggaactc agcgcagccg   3600
aacaggaact gcttctcacc ctgccttccc tggaatctct tgaagtctca gggacaatcc   3660
agtcacaaga ccaaatcttt cctaatctgg ataagttcct gtgcctgaaa gaactgtctg   3720
tggatctgga gggcaatata atgtttttt cagtcattcc tgaagaattt ccaaacttcc   3780
accatatgga gaaattattg atccaaattt cagctgagta tgatccttcc aaactagtaa   3840
tgccagtttg ccaaattta tttctctgaa gatattaaat cttgaaggcc agcaatttcc   3900
tgatgaggaa acatcagaaa aatttgccta cattttaggt tctcttagta acctggaaga   3960
```

```
attgatcctt cctactgggg atggaattta tcgagtggcc aaactgatca tccagcagtg   4020
tcagcagctt cattgtctcc gagtcctctc atttttcaag actttgaatg atgacagcgt   4080
ggtggaaatt ggttaaaaat gtgtctgcag gcacacagga cgtgccttca cccccatctg   4140
actatgtgga aagagttgac agtcccatgg catactcttc caatggcaaa gtgaatgaca   4200
agcggtttta tccagagtct tcctataaat ccacgccggt tcctgaagtg gttcaggagc   4260
ttccattaac ttcgcctgtg gatgacttca ggcagcctcg ttacagcagc ggtggtaact   4320
ttgagacacc ttcaaaaaga gcacctgcaa agggaagagc aggaaggtca aagagaacag   4380
agcaagatca ctatgagaca gactacacaa ctggcggcga gtcctgtgat gagctggagg   4440
aggactggat cagggaatat ccacctatca cttcagatca acaaagacaa ctgtacaaga   4500
ggaattttga cactggccta caggaataca agagcttaca atcagaactt gatgagatca   4560
ataaagaact ctcccgtttg gataaagaat tggatgacta tagagaagaa agtgaagagt   4620
acatggctgc tgctgatgaa tacaatagac tgaagcaagt gaagggatct gcagattaca   4680
aaagtaagaa gaatcattgc aagcagttaa acagcaaatt gtcacacatc aagaagatgg   4740
ttggagacta tgatagacag aaaacataga aggctgatgc caagttgttt gagaaattaa   4800
gtatctgaca tctctgcaat cttctcagaa ggcaaatgac tttggaccat aaccccggaa   4860
gccaaacctc tgtgagcatc acagttttgg ttgctttaat atcatcagta ttgaagcatt   4920
ttataaatcg cttttgataa tcaactgggc tgaacactcc aattaaggat tttatgcttt   4980
aaacattggt tcttgtatta agaatgaaat actgtttgag gttttttaagc cttaaaggaa   5040 ggttctggtg tgaactaaac tttcacaccc cagacgatgt cttcatacct acatgtattt   5100
gtttgcatag gtgatctcat ttaatcctct caaccacctt tcagataact gttatttata   5160
atcacttttt tccacataag gaaactgggt tcctgcaatg aagtctctga agtgaaactg   5220
cttgtttcct agcacacact tttggttaag tctgtttat gacttcatta ataataaatt   5280
ccggcatcat acagctactc ctccctaccg ccacctccac agacaccact tcctggttc   5340 catctcctct gctgcttcta gctccctgct ctggcttcaa ggtgcgcagg acctgcttcc   5400
ttggtgatcc tctgtagtct cccacacccc acattatcta caaactgatg actcctaatt   5460
tacatctcca gctcagacct ctccatcaat cccaacgcat acac             5504

<210> SEQ ID NO 2
<211> LENGTH: 6133
<212> TYPE: DNA
<213> ORGANISM: Homo sapiens

<400> SEQUENCE: 2
tgcatgaaga caaaaggtcc tgtgctcacc tgggacccctt ctggacgttg ccctgtgtac     60
ctcttcgact gcctgttcat ctacgacgaa ccccgggtat tgaccccaga caacaatgcc    120
acttcatatt ggggacttcg tctgggattc caaggtgcat tcattgcaaa gttccttaaa    180
tattttctca ctgcttccta ctaaaggacg gacagagcat tgttcttca gccacatact    240 ttccttccac tggccagcat tctcctctat tagactagaa ctgtggataa acctcagaaa    300
atggccaccc agcagaaagc ctctgacgag aggatctccc agtttgatca caatttgctg    360
ccagagctgt ctgctcttct gggcctagat gcagttcagt tggcaaagga actagaagaa    420
gaggagcaga aggagcgagc aaaaatgcag aaaggctaca actctcaaat gcgcagtgaa    480
gcaaaaaggt taaagacttt tgtgacttat gagccgtaca gctcatggat accacaggag    540
atggcggccg ctgggttttta cttcactggg gtaaaatctg ggattcagtg cttctgctgt    600
```

```
agcctaatcc tctttggtgc cggcctcacg agactcccca tagaagacca caagaggttt    660
catccagatt gtgggttcct tttgaacaag gatgttggta acattgccaa gtacgacata    720
agggtgaaga atctgaagag caggctgaga ggaggtaaaa tgaggtacca agaagaggag    780
gctagacttg cgtccttcag gaactggcca ttttatgtcc aagggatatc cccttgtgtg    840
ctctcagagg ctggctttgt ctttacaggt aaacaggaca cggtacagtg ttttttcctgt    900 ggtggatgtt taggaaattg ggaagaagga gatgatcctt ggaaggaaca tgccaaatgg    960
ttccccaaat gtgaatttct tcggagtaag aaatcctcag aggaaattac ccagtatatt   1020
caaagctaca agggatttgt tgacataacg ggagaacatt ttgtgaattc ctgggtccag   1080
agagaattac ctatggcatc agcttattgc aatgacagca tctttgctta cgaagaacta   1140
cggctggact cttttaagga ctggccccgg gaatcagctg tgggagttgc agcactggcc   1200
aaagcaggtc ttttctacac aggtataaag gacatcgtcc agtgcttttc ctgtggaggg   1260
tgtttagaga atggcagga aggtgatgac ccattagacg atcacaccag atgttttccc   1320
aattgtccat ttctccaaaa tatgaagtcc tctgcggaag tgactccaga ccttcagagc   1380
cgtggtgaac tttgtgaatt actggaaacc acaagtgaaa gcaatcttga agattcaata   1440
gcagttggtc ctatagtgcc agaaatggca cagggtgaag cccagtggtt tcaagaggca   1500
aagaatctga atgagcagct gagagcagct tataccagcg ccagtttccg ccacatgtct   1560
ttgcttgata tctcttccga tctggccacg gaccacttgc tgggctgtga tctgtctatt   1620
gcttcaaaac acatcagcaa acctgtgcaa gaacctctgg tgctgcctga ggtctttggc   1680
aacttgaact ctgtcatgtg tgtggagggt gaagctggaa gtggaaagac ggtcctcctg   1740
aagaaaatag ctttctctgtg ggcatctgga tgctgtcccc tgttaaacag gttccagctg   1800
gttttctacc tctcccttag ttccaccaga ccagacgagg ggctggccag tatcatctgt   1860
gaccagctcc tagagaaaga aggatctgtt actgaaatgt gcatgaggaa cattatccag   1920
cagttaaaga atcaggtctt attccttttta gatgactaca agaaaatatg ttcaatccct   1980
caagtcatag gaaaactgat tcaaaaaaac cacttatccc ggacctgcct attgattgct   2040
gtccgtacaa acagggccag ggacatccgc cgatacctag agaccattct agagatcaaa   2100
gcatttccct tttataatac tgtctgtata ttacggaagc tcttttcaca taatatgact   2160
cgtctgcgaa agtttatggt ttactttgga aagaaccaaa gtttgcagaa gatacagaaa   2220
actcctctct ttgtggcggc gatctgtgct cattggtttc agtatccttt tgacccatcc   2280
tttgatgatg tggctgtttt caagtccat atggaacgcc tttccttaag gaacaaagcg   2340
acagctgaaa ttctcaaagc aactgtgtcc tcctgtggtg agctggcctt gaaagggttt   2400
ttttcatgtt gctttgagtt taatgatgat gatctcgcag aagcagggt tgatgaagat   2460 gaagatctaa ccatgtgctt gatgagcaaa tttacagccc agagactaag accattctac   2520
cggtttttaa gtcctgcctt ccaagaattt cttgcgggga tgaggctgat tgaactcctg   2580
gattcagata ggcaggaaca tcaagatttg ggactgtatc atttgaaaca aatcaactca   2640
cccatgatga ctgtaagcgc ctacaacaat ttttttgaact atgtctccag cctcccttca   2700
acaaaagcag ggcccaaaat tgtgtctcat ttgctccatt tagtggataa caaagagtca   2760
ttggagaata tatctgaaaa tgatgactac ttaaagcacc agccagaaat ttcactgcag   2820
atgcagttac ttaggggatt gtggcaaatt tgtccacaag cttactttttc aatggtttca   2880 gaacatttac tggttcttgc cctgaaaact gcttatcaaa gcaacactgt tgctgcgtgt   2940
tctccatttg ttttgcaatt ccttcaaggg agaacactga ctttgggtgc gcttaactta   3000
```

```
cagtactttt tcgaccaccc agaaagcttg tcattgttga ggagcatcca cttcccaata    3060
cgaggaaata agacatcacc cagagcacat ttttcagttc tggaaacatg ttttgacaaa    3120
tcacaggtgc caactataga tcaggactat gcttctgcct ttgaacctat gaatgaatgg    3180
gagcgaaatt tagctgaaaa agaggataat gtaaagagct atatggatat gcagcgcagg    3240
gcatcaccag accttagtac tggctattgg aaactttctc caaagcagta caagattccc    3300
tgtctagaag tcgatgtgaa tgatattgat gttgtaggcc aggatatgct tgagattcta    3360
atgacagttt tctcagcttc acagcgcatc gaactccatt taaaccacag cagaggcttt    3420
atagaaagca tccgcccagc tcttgagctg tctaaggcct ctgtcaccaa gtgctccata    3480
agcaagttgg aactcagcgc agccgaacag gaactgcttc tcaccctgcc ttccctggaa    3540
tctcttgaag tctcagggac aatccagtca caagaccaaa tctttcctaa tctgataag     3600 ttcctgtgcc tgaaagaact gtctgtggat ctggagggca atataaatgt ttttcagtc     3660 attcctgaag aatttccaaa cttccaccat atggagaaat tattgatcca aatttcagct    3720
gagtatgatc cttccaaact agtaaaatta attcaaaatt ctccaaacct tcatgttttc    3780
catctgaagt gtaacttctt ttcggatttt gggtctctca tgactatgct tgtttcctgt    3840
aagaaactca cagaaattaa gttttcggat tcatttttc aagccgtccc atttgttgcc     3900
agtttgccaa attttatttc tctgaagata ttaaatcttg aaggccagca atttcctgat    3960
gaggaaacat cagaaaaatt tgcctacatt ttaggttctc ttagtaaccct ggaagaattg    4020 atccttccta ctgggatgg aatttatcga gtggccaaac tgatcatcca gcagtgtcag    4080
cagcttcatt gtctccgagt cctctcattt ttcaagactt tgaatgatga cagcgtggtg    4140
gaaattgcca agtagcaat cagtggaggt ttccagaaac ttgagaacct aaagctttca     4200
atcaatcaca agattacaga ggaaggatac agaaatttct ttcaagcact ggacaacatg    4260
ccaaacttgc aggagttgga catctccagg catttcacag agtgtatcaa agctcaggcc    4320
acaacagtca agtctttgag tcaatgtgtg ttacgactac caaggctcat tagactgaac    4380
atgttaagtt ggctcttgga tgcagatgat attgcattgc ttaatgtcat gaaagaaaga    4440
catcctcaat ctaagtactt aactattctc cagaaatgga tactgccgtt ctctccaatc    4500
attcagaaat aaaagattca gctaaaaact gctgaatcaa taatttgtct tggggcatat    4560
tgaggatgta aaaaagttg ttgattaatg ctaaaaacca aattatccaa aattatttta     4620
ttaaatattg catacaaaag aaaatgtgta aggcttgcta aaaaacaaaa caaaacaaaa    4680
cacagtcctg catactcacc accaagctca agaaataaat catcaccaat acctttgagg    4740
tccctgagta atccacccca gctaaaggca aaccttcaa tcaagtttat acagcaaacc     4800
ctccattgtc catggtcaac agggaagggg ttggggacag gtctgccaat ctatctaaaa    4860
gccacaatat ggaagaagta ttcaatttat ataataaatg gctaacttaa cggttgaatc    4920
actttcatac atggatgaaa cgggtttaac acaggatcca catgaatctt ctgtgggcca    4980
agagatgttc cttaatcctt gtagaacctg ttttctatat tgaactagct ttggtacagt    5040
agagttaact tactttccat ttatccactg ccaatataaa gaggaaacag gggttaggga    5100
aaaatgactt cattccagag gcttctcaga gttcaacata tgctataatt tagaatttc     5160 ttatgaatcc actctacttg ggtagaaaat attttatctc tagtgattgc atattatttc    5220
catatcatag tatttcatag tattatattt gatatgagtg tctatatcaa tgtcagtgtc    5280
cagaatttcg ttcctaccag ttaagtagtt ttctgaacgg ccagaagacc attcgaaatt    5340
catgatacta ctataagttg gtaaacaacc atactttat cctcattttt attctcacta     5400
```

-continued

| | |
|---|---|
| agaaaaaagt caactcccct cccctttgccc aagtatgaaa tatagggaca gtatgtatgg | 5460 |
| tgtggtctca tttgtttaga aaaccactta tgactgggtg cggtggctca cacctgtaat | 5520 |
| cccagcactt tgggaggctg aggcgggcga atcatttgag gtgaggaatt cgagaccagc | 5580 |
| ctggccagca tggtgaaacc ccatctctac taaaaataca aaaattagcc aggtgtggtg | 5640 |
| gcacatgcct gtagtcccag ccactagggc ggctgagacg caagacttgc ttgaacccgg | 5700 |
| gaggcagagg ttgcagtgag ccaagatggc gccactgcat tccagcctgg gcaacagagc | 5760 |
| aagaccctgt ctgtctcaaa acaaaaaaca aaaccactta tattgctagc tacattaaga | 5820 |
| atttctgaat atgttactga gcttgcttgt ggtaaccatt tataatatca gaaagtatat | 5880 |
| gtacaccaaa acatgttgaa catccatgtt gtacaactga aatataaata attttgtcaa | 5940 |
| ttatacctaa ataaaactgg aaaaaaattt ctggaagttt atatctaaaa atgttaatag | 6000 |
| tgcgtacctc taggaagtgg gcctggaagc cattcttact tttcagtctc tcccattctg | 6060 |
| tactgttttt tgttttactt tcgtgcctgc attattttc tatttaaaac aaaaataaat | 6120 |
| ctagtttagc act | 6133 |

```
<210> SEQ ID NO 3
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 3
atgcttggat ctctagaatg g                                         21

<210> SEQ ID NO 4
<211> LENGTH: 20
<212> TYPE: DNA
<213> ORGANISM: Artificial Sequence
<220> FEATURE:
<223> OTHER INFORMATION: Synthetic primer based on Homo sapiens

<400> SEQUENCE: 4
agcaaagaca tgtggcggaa                                           20

<210> SEQ ID NO 5
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 5
ccagctccta gagaaagaag ga                                        22

<210> SEQ ID NO 6
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 6
gaactacggc tggactcttt t                                         21

<210> SEQ ID NO 7
<211> LENGTH: 21
<212> TYPE: DNA
<213> ORGANISM: Artificial Sequence
```

```
<220> FEATURE:
<223> OTHER INFORMATION: Synthetic primer based on Homo sapiens

<400> SEQUENCE: 7
ctctcagcct gctcttcaga t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 8
aaagcctctg acgagaggat c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 9
cgactgcctg ttcatctacg a                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 10
tttgttctcc agccacatac t                                              21

<210> SEQ ID NO 11
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 11
catttggcat gttccttcca ag                                             22

<210> SEQ ID NO 12
<211> LENGTH: 27
<212> TYPE: DNA
<213> ORGANISM: Artificial Sequence
<220> FEATURE:
<223> OTHER INFORMATION: Syntehtic primer based on Homo sapiens

<400> SEQUENCE: 12
gtagatgaat actgatgttt cataatt                                        27

<210> SEQ ID NO 13
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 13
tgccactgcc aggcaatcta a                                              21
```

<210> SEQ ID NO 14
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 14
taaacaggac acggtacagt g                                    21

<210> SEQ ID NO 15
<211> LENGTH: 24
<212> TYPE: DNA
<213> ORGANISM: Artificial Sequence
<220> FEATURE:
<223> OTHER INFORMATION: Synthetic primer based on Homo sapiens

<400> SEQUENCE: 15
catgttttaa gtctcggtgc tctg                                 24

<210> SEQ ID NO 16
<211> LENGTH: 23
<212> TYPE: DNA
<213> ORGANISM: Artificial Sequence
<220> FEATURE:
<223> OTHER INFORMATION: Synthetic primer based on Homo sapiens

<400> SEQUENCE: 16
ttagccagat gtgttggcac atg                                  23

<210> SEQ ID NO 17
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 17
gattctatgt gataggcagc ca                                   22

<210> SEQ ID NO 18
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 18
gccactgctc ccgatggatt a                                    21

<210> SEQ ID NO 19
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 19
gctctcagct gctcattcag at                                   22

<210> SEQ ID NO 20
<211> LENGTH: 21
<212> TYPE: DNA
<213> ORGANISM: Artificial Sequence
<220> FEATURE:
<223> OTHER INFORMATION: Synthetic primer based on Homo sapiens

```
<400> SEQUENCE: 20
acaaagttca ccacggctct g                                              21

<210> SEQ ID NO 21
<211> LENGTH: 6124
<212> TYPE: DNA
<213> ORGANISM: Homo sapiens

<400> SEQUENCE: 21
acaaaaggtc ctgtgctcac ctgggaccct tctggacgtt gccctgtgta cctcttcgac    60
tgcctgttca tctacgacga accccgggta ttgaccccag acaacaatgc cacttcatat   120
tggggacttc gtctgggatt ccaaggtgca ttcattgcaa agttccttaa atattttctc   180
actgcttcct actaaaggac ggacagagca tttgttcttc agccacatac tttccttcca   240
ctggccagca ttctcctcta ttagactaga actgtggata aacctcagaa aatggccacc   300
cagcagaaag cctctgacga gaggatctcc cagtttgatc acaatttgct gccagagctg   360
tctgctcttc tgggcctaga tgcagttcag ttggcaaagg aactagaaga agaggagcag   420
aaggagcgag caaaaatgca gaaaggctac aactctcaaa tgcgcagtga agcaaaaagg   480
ttaaagactt ttgtgactta tgagccgtac agctcatgga taccacagga gatggcggcc   540
gctgggtttt acttcactgg ggtaaaatct gggattcagt gcttctgctg tagcctaatc   600
ctctttggtg ccggcctcac gagactcccc atagaagacc acaagaggtt tcatccagat   660
tgtgggttcc ttttgaacaa ggatgttggt aacattgcca agtacgacat aagggtgaag   720
aatctgaaga gcaggctgag aggaggtaaa atgaggtacc aagaagagga ggctagactt   780
gcgtccttca ggaactggcc attttatgtc caagggatat ccccttgtgt gctctcagag   840
gctggctttg tctttacagg taaacaggac acggtacagt gttttcctg tggtggatgt    900 ttaggaaatt gggaagaagg agatgatcct tggaaggaac atgccaaatg gttccccaaa   960
tgtgaatttc ttcggagtaa gaaatcctca gaggaaatta cccagtatat tcaaagctac  1020
aagggatttg ttgacataac gggagaacat tttgtgaatt cctgggtcca gagagaatta  1080
cctatggcat cagcttattg caatgacagc atctttgctt acgaagaact acggctggac  1140
tcttttaagg actggccccg ggaatcagct gtgggagttg cagcactggc caaagcaggt  1200
cttttctaca caggtataaa ggacatcgtc cagtgctttt cctgtggagg gtgtttagag  1260
aaatggcagg aaggtgatga cccattagac gatcacacca gatgttttcc caattgtcca  1320
tttctccaaa atatgaagtc ctctgcggaa gtgactccag accttcagag ccgtggtgaa  1380
ctttgtgaat tactgaaaac cacaagtgaa agcaatcttg aagattcaat agcagttggt  1440
cctatagtgc cagaaatggc acagggtgaa gcccagtggt tcaagagggc aaagaatctg  1500
aatgagcagc tgagagcagc ttataccagc gccagtttcc gccacatgtc tttgcttgat  1560
atctcttccg atctggccac ggaccacttg ctgggctgtg atctgtctat tgcttcaaaa  1620
cacatcagca aacctgtgca agaacctctg gtgctgcctg aggtctttgg caacttgaac  1680
tctgtcatgt gtgtgaggg tgaagctgga agtggaaaga cggtcctcct gaagaaaata  1740
gcttttctgt gggcatctgg atgctgtccc ctgttaaaca ggttccagct ggttttctac  1800
ctctccctta gttccaccag accagacgag gggctggcca gtatcatctg tgaccagctc  1860
ctagagaaag aaggatctgt tactgaaatg tgcatgagga acattatcca gcagttaaag  1920
aatcaggtct tattccttttt agatgactac aaagaaatat gttcaatccc tcaagtcata  1980
ggaaaactga ttcaaaaaaa ccacttatcc cggacctgcc tattgattgc tgtccgtaca  2040
```

-continued

```
aacagggcca gggacatccg ccgatacccta gagaccattc tagagatcaa agcatttccc    2100
ttttataata ctgtctgtat attacggaag ctctttttcac ataatatgac tcgtctgcga    2160
aagtttatgg tttactttgg aaagaaccaa agtttgcaga agatacagaa aactcctctc    2220
tttgtggcgg cgatctgtgc tcattggttt cagtatcctt ttgacccatc ctttgatgat    2280
gtggctgttt tcaagtccta tatggaacgc ctttccttaa ggaacaaagc gacagctgaa    2340
attctcaaag caactgtgtc ctcctgtggt gagctggcct tgaaagggtt tttttcatgt    2400
tgctttgagt ttaatgatga tgatctcgca gaagcagggg ttgatgaaga tgaagatcta    2460
accatgtgct tgatgagcaa atttacagcc cagagactaa gaccattcta ccggttttta    2520
agtcctgcct tccaagaatt tcttgcgggg atgaggctga ttgaactcct ggattcagat    2580
aggcaggaac atcaagattt gggactgtat catttgaaac aaatcaactc acccatgatg    2640
actgtaagcg cctacaacaa ttttttgaac tatgtctcca gcctcccttc aacaaaagca    2700
gggcccaaaa ttgtgtctca tttgctccat ttagtggata acaaagagtc attggagaat    2760
atatctgaaa atgatgacta cttaaagcac cagccagaaa tttcactgca gatgcagtta    2820
cttaggggat tgtggcaaat ttgtccacaa gcttactttt caatggtttc agaacattta    2880
ctggttcttg ccctgaaaac tgcttatcaa agcaacactg ttgctgcgtg ttctccattt    2940
gttttgcaat tccttcaagg gagaacactg actttgggtg cgcttaactt acagtacttt    3000
ttcgaccacc cagaaagctt gtcattgttg aggagcatcc acttcccaat acgaggaaat    3060
aagcatcac ccagagcaca tttttcagtt ctggaaacat gttttgacaa atcacagtg    3120
ccaactatag atcaggacta tgcttctgcc tttgaaccta tgaatgaatg ggagcgaaat    3180
ttagctgaaa aagaggataa tgtaaagagc tatatggata tgcagcgcag ggcatcacca    3240
gaccttagta ctggctattg gaaactttct ccaaagcagt acaagattcc ctgtctagaa    3300
gtcgatgtga atgatattga tgttgtaggc caggatatgc ttgagattct aatgacagtt    3360
ttctcagctt cacagcgcat cgaactccat ttaaaccaca gcagaggctt tatagaaagc    3420
atccgcccag ctcttgagct gtctaaggcc tctgtcacca agtgctccat aagcaagttg    3480
gaactcagcg cagccgaaca ggaactgctt ctcaccctgc cttccctgga atctcttgaa    3540
gtctcaggga caatccagtc acaagaccaa atctttccta atctggataa gttcctgtgc    3600
ctgaaagaac tgtctgtgga tctggagggc aatataaatg tttttttcagt cattcctgaa    3660
gaatttccaa acttccacca tatggagaaa ttattgatcc aaatttcagc tgagtatgat    3720
ccttccaaac tagtaaaatt aattcaaaat tctccaaacc ttcatgtttt ccatctgaag    3780
tgtaacttct tttcggattt tgggtctctc atgactatgc ttgtttcctg taagaaactc    3840
acagaaatta agttttcgga ttcattttt caagccgtcc catttgttgc cagtttgcca    3900
aatttttattt ctctgaagat attaaatctt gaaggccagc aatttcctga tgaggaaaca    3960
tcagaaaaat ttgcctacat tttaggttct cttagtaacc tggaagaatt gatccttcct    4020
actggggatg gaatttatcg agtggccaaa ctgatcatcc agcagtgtca gcagcttcat    4080
tgtctccgag tcctctcatt tttcaagact ttgaatgatg acagcgtggt ggaaattgcc    4140
aaagtagcaa tcagtggagg tttccagaaa cttgagaacc taaagctttc aatcaatcac    4200
aagattacag aggaaggata cagaaattttc tttcaagcac tggacaacat gccaaacttg    4260
caggagttgg acatctccag gcatttcaca gagtgtatca agctcaggc cacaacagtc    4320
aagtctttga gtcaatgtgt gttacgacta ccaaggctca ttagactgaa catgttaagt    4380
tggctcttgg atgcagatga tattgcattg cttaatgtca tgaaagaaag acatcctcaa    4440
```

-continued

```
tctaagtact taactattct ccagaaatgg atactgccgt tctctccaat cattcagaaa    4500
taaaagattc agctaaaaac tgctgaatca ataatttgtc ttggggcata ttgaggatgt    4560
aaaaaaagtt gttgattaat gctaaaaacc aaattatcca aaattatttt attaaatatt    4620
gcatacaaaa gaaatgtgt aaggcttgct aaaaaacaaa acaaaacaaa acacagtcct    4680
gcatactcac caccaagctc aagaaataaa tcatcaccaa tacctttgag gtccctgagt    4740
aatccacccc agctaaaggc aaaccettca atcaagtttta tacagcaaac cctccattgt    4800
ccatggtcaa cagggaaggg gttggggaca ggtctgccaa tctatctaaa agccacaata    4860
tggaagaagt attcaattta tataataaat ggctaactta acggttgaat cactttcata    4920
catggatgaa acgggtttaa cacaggatcc acatgaatct tctgtgggcc aagagatgtt    4980
ccttaatcct tgtagaacct gttttctata ttgaactagc tttggtacag tagagttaac    5040
ttactttcca tttatccact gccaatataa agaggaaaca ggggttaggg aaaaatgact    5100
tcattccaga ggcttctcag agttcaacat atgctataat ttagaatttt cttatgaatc    5160
cactctactt gggtagaaaa tattttatct ctagtgattg catattattt ccatatcata    5220
gtatttcata gtattatatt tgatatgagt gtctatatca atgtcagtgt ccagaatttc    5280
gttcctacca gttaagtagt tttctgaacg gccagaagac cattcgaaat tcatgatact    5340
actataagtt ggtaaacaac catactttta tcctcatttt tattctcact aagaaaaaag    5400
tcaactcccc tccccttgcc caagtatgaa atatagggac agtatgtatg gtgtggtctc    5460
atttgtttag aaaaccactt atgactgggt gcggtggctc acacctgtaa tcccagcact    5520
ttgggaggct gaggcgggcg aatcatttga ggtgaggaat tcgagaccag cctggccagc    5580
atggtgaaac cccatctcta ctaaaaatac aaaaattagc caggtgtggt ggcacatgcc    5640
tgtagtccca gccactaggg cggctgagac gcaagacttg cttgaacccg ggaggcagag    5700
gttgcagtga gccaagatgg cgccactgca ttccagcctg ggcaacagag caagaccctg    5760
tctgtctcaa aacaaaaaac aaaaccactt atattgctag ctacattaag aatttctgaa    5820
tatgttactg agcttgcttg tggtaaccat ttataatatc agaaagtata tgtacaccaa    5880
aacatgttga acatccatgt tgtacaactg aaatataaat aattttgtca attataccta    5940
aataaaactg gaaaaaaatt tctggaagtt tatatctaaa aatgttaata gtgcgtacct    6000
ctaggaagtg ggcctggaag ccattcttac ttttcagtct ctcccattct gtactgtttt    6060
ttgttttact ttcgtgcctg cattattttt ctatttaaaa caaaaataaa tctagtttag    6120
cact                                                                6124
```

<210> SEQ ID NO 22
<211> LENGTH: 1403
<212> TYPE: PRT
<213> ORGANISM: Homo sapiens

<400> SEQUENCE: 22

```
Met Ala Thr Gln Gln Lys Ala Ser Asp Glu Arg Ile Ser Gln Phe Asp
 1               5                   10                  15

His Asn Leu Leu Pro Glu Leu Ser Ala Leu Leu Gly Leu Asp Ala Val
             20                  25                  30

Gln Leu Ala Lys Glu Leu Glu Glu Glu Gln Lys Glu Arg Ala Lys
         35                  40                  45

Met Gln Lys Gly Tyr Asn Ser Gln Met Arg Ser Glu Ala Lys Arg Leu
     50                  55                  60
```

```
Lys Thr Phe Val Thr Tyr Glu Pro Tyr Ser Ser Trp Ile Pro Gln Glu
 65                  70                  75                  80

Met Ala Ala Gly Phe Tyr Phe Thr Gly Val Lys Ser Gly Ile Gln
                 85                  90                  95

Cys Phe Cys Ser Leu Ile Leu Phe Gly Ala Gly Leu Thr Arg Leu
            100                 105                 110

Pro Ile Glu Asp His Lys Arg Phe His Pro Asp Cys Gly Phe Leu Leu
            115                 120                 125

Asn Lys Asp Val Gly Asn Ile Ala Lys Tyr Asp Ile Arg Val Lys Asn
130                 135                 140

Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
            195                 200                 205

Glu Gly Asp Asp Pro Trp Lys Glu His Ala Lys Trp Phe Pro Lys Cys
    210                 215                 220

Glu Phe Leu Arg Ser Lys Lys Ser Glu Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
        275                 280                 285

Pro Arg Glu Ser Ala Val Gly Val Ala Ala Leu Ala Lys Ala Gly Leu
    290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp His Thr
                325                 330                 335

Arg Cys Phe Pro Asn Cys Pro Phe Leu Gln Asn Met Lys Ser Ser Ala
            340                 345                 350

Glu Val Thr Pro Asp Leu Gln Ser Arg Gly Glu Leu Cys Glu Leu Leu
            355                 360                 365

Glu Thr Thr Ser Glu Ser Asn Leu Glu Asp Ser Ile Ala Val Gly Pro
370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415

Arg His Met Ser Leu Leu Asp Ile Ser Ser Asp Leu Ala Thr Asp His
            420                 425                 430

Leu Leu Gly Cys Asp Leu Ser Ile Ala Ser Lys His Ile Ser Lys Pro
            435                 440                 445

Val Gln Glu Pro Leu Val Leu Pro Glu Val Phe Gly Asn Leu Asn Ser
    450                 455                 460

Val Met Cys Val Glu Gly Glu Ala Gly Ser Gly Lys Thr Val Leu Leu
465                 470                 475                 480
```

```
Lys Lys Ile Ala Phe Leu Trp Ala Ser Gly Cys Cys Pro Leu Leu Asn
            485                 490                 495

Arg Phe Gln Leu Val Phe Tyr Leu Ser Leu Ser Ser Thr Arg Pro Asp
            500                 505                 510

Glu Gly Leu Ala Ser Ile Ile Cys Asp Gln Leu Leu Glu Lys Glu Gly
            515                 520                 525

Ser Val Thr Glu Met Cys Met Arg Asn Ile Ile Gln Gln Leu Lys Asn
        530                 535                 540

Gln Val Leu Phe Leu Leu Asp Asp Tyr Lys Glu Ile Cys Ser Ile Pro
545                 550                 555                 560

Gln Val Ile Gly Lys Leu Ile Gln Lys Asn His Leu Ser Arg Thr Cys
            565                 570                 575

Leu Leu Ile Ala Val Arg Thr Asn Arg Ala Arg Asp Ile Arg Arg Tyr
            580                 585                 590

Leu Glu Thr Ile Leu Glu Ile Lys Ala Phe Pro Phe Tyr Asn Thr Val
            595                 600                 605

Cys Ile Leu Arg Lys Leu Phe Ser His Asn Met Thr Arg Leu Arg Lys
            610                 615                 620

Phe Met Val Tyr Phe Gly Lys Asn Gln Ser Leu Gln Lys Ile Gln Lys
625                 630                 635                 640

Thr Pro Leu Phe Val Ala Ala Ile Cys Ala His Trp Phe Gln Tyr Pro
            645                 650                 655

Phe Asp Pro Ser Phe Asp Asp Val Ala Val Phe Lys Ser Tyr Met Glu
            660                 665                 670

Arg Leu Ser Leu Arg Asn Lys Ala Thr Ala Glu Ile Leu Lys Ala Thr
            675                 680                 685

Val Ser Ser Cys Gly Glu Leu Ala Leu Lys Gly Phe Phe Ser Cys Cys
            690                 695                 700

Phe Glu Phe Asn Asp Asp Leu Ala Glu Ala Gly Val Asp Glu Asp
705                 710                 715                 720

Glu Asp Leu Thr Met Cys Leu Met Ser Lys Phe Thr Ala Gln Arg Leu
            725                 730                 735

Arg Pro Phe Tyr Arg Phe Leu Ser Pro Ala Phe Gln Glu Phe Leu Ala
            740                 745                 750

Gly Met Arg Leu Ile Glu Leu Leu Asp Ser Asp Arg Gln Glu His Gln
            755                 760                 765

Asp Leu Gly Leu Tyr His Leu Lys Gln Ile Asn Ser Pro Met Met Thr
            770                 775                 780

Val Ser Ala Tyr Asn Asn Phe Leu Asn Tyr Val Ser Ser Leu Pro Ser
785                 790                 795                 800

Thr Lys Ala Gly Pro Lys Ile Val Ser His Leu Leu His Leu Val Asp
            805                 810                 815

Asn Lys Glu Ser Leu Glu Asn Ile Ser Glu Asn Asp Asp Tyr Leu Lys
            820                 825                 830

His Gln Pro Glu Ile Ser Leu Gln Met Gln Leu Leu Arg Gly Leu Trp
            835                 840                 845

Gln Ile Cys Pro Gln Ala Tyr Phe Ser Met Val Ser Glu His Leu Leu
            850                 855                 860

Val Leu Ala Leu Lys Thr Ala Tyr Gln Ser Asn Thr Val Ala Ala Cys
865                 870                 875                 880

Ser Pro Phe Val Leu Gln Phe Leu Gln Gly Arg Thr Leu Thr Leu Gly
            885                 890                 895
```

```
Ala Leu Asn Leu Gln Tyr Phe Phe Asp His Pro Glu Ser Leu Ser Leu
            900                 905                 910

Leu Arg Ser Ile His Phe Pro Ile Arg Gly Asn Lys Thr Ser Pro Arg
            915                 920                 925

Ala His Phe Ser Val Leu Glu Thr Cys Phe Asp Lys Ser Gln Val Pro
            930                 935                 940

Thr Ile Asp Gln Asp Tyr Ala Ser Ala Phe Glu Pro Met Asn Glu Trp
945                 950                 955                 960

Glu Arg Asn Leu Ala Glu Lys Glu Asp Asn Val Lys Ser Tyr Met Asp
            965                 970                 975

Met Gln Arg Arg Ala Ser Pro Asp Leu Ser Thr Gly Tyr Trp Lys Leu
            980                 985                 990

Ser Pro Lys Gln Tyr Lys Ile Pro Cys Leu Glu Val Asp Val Asn Asp
            995                1000                1005

Ile Asp Val Val Gly Gln Asp Met Leu Glu Ile Leu Met Thr Val Phe
           1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
           1045                1050                1055

Lys Cys Ser Ile Ser Lys Leu Glu Leu Ser Ala Ala Glu Gln Glu Leu
           1060                1065                1070

Leu Leu Thr Leu Pro Ser Leu Glu Ser Leu Glu Val Ser Gly Thr Ile
           1075                1080                1085

Gln Ser Gln Asp Gln Ile Phe Pro Asn Leu Asp Lys Phe Leu Cys Leu
           1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
           1125                1130                1135

Gln Ile Ser Ala Glu Tyr Asp Pro Ser Lys Leu Val Lys Leu Ile Gln
           1140                1145                1150

Asn Ser Pro Asn Leu His Val Phe His Leu Lys Cys Asn Phe Phe Ser
           1155                1160                1165

Asp Phe Gly Ser Leu Met Thr Met Leu Val Ser Cys Lys Lys Leu Thr
1170                1175                1180

Glu Ile Lys Phe Ser Asp Ser Phe Phe Gln Ala Val Pro Phe Val Ala
1185                1190                1195                1200

Ser Leu Pro Asn Phe Ile Ser Leu Lys Ile Leu Asn Leu Glu Gly Gln
           1205                1210                1215

Gln Phe Pro Asp Glu Glu Thr Ser Glu Lys Phe Ala Tyr Ile Leu Gly
           1220                1225                1230

Ser Leu Ser Asn Leu Glu Glu Leu Ile Leu Pro Thr Gly Asp Gly Ile
           1235                1240                1245

Tyr Arg Val Ala Lys Leu Ile Ile Gln Gln Cys Gln Gln Leu His Cys
1250                1255                1260

Leu Arg Val Leu Ser Phe Phe Lys Thr Leu Asn Asp Asp Ser Val Val
1265                1270                1275                1280

Glu Ile Ala Lys Val Ala Ile Ser Gly Gly Phe Gln Lys Leu Glu Asn
1285                1290                1295

Leu Lys Leu Ser Ile Asn His Lys Ile Thr Glu Glu Gly Tyr Arg Asn
           1300                1305                1310
```

-continued

```
Phe Phe Gln Ala Leu Asp Asn Met Pro Asn Leu Gln Glu Leu Asp Ile
    1315                1320                1325
Ser Arg His Phe Thr Glu Cys Ile Lys Ala Gln Ala Thr Thr Val Lys
    1330                1335                1340
Ser Leu Ser Gln Cys Val Leu Arg Leu Pro Arg Leu Ile Arg Leu Asn
1345                1350                1355                1360
Met Leu Ser Trp Leu Leu Asp Ala Asp Asp Ile Ala Leu Leu Asn Val
            1365                1370                1375
Met Lys Glu Arg His Pro Gln Ser Lys Tyr Leu Thr Ile Leu Gln Lys
        1380                1385                1390
Trp Ile Leu Pro Phe Ser Pro Ile Ile Gln Lys
        1395                1400

<210> SEQ ID NO 23
<211> LENGTH: 6228
<212> TYPE: DNA
<213> ORGANISM: Homo sapiens

<400> SEQUENCE: 23
ttccggctgg acgttgccct gtgtacctct tcgactgcct gttcatctac gacgaacccc      60
gggtattgac cccagacaac aatgccactt catattgcat gaagacaaaa ggtcctgtgc     120
tcacctggga cccttctgga cgttgccctg tgtacctctt cgactgcctg ttcatctacg     180
acgaaccccg ggtattgacc ccagacaaca atgccacttc atattgggga cttcgtctgg     240
gattccaagg tgcattcatt gcaaagttcc ttaaatattt tctcactgct tcctactaaa     300
ggacggacag agcatttgtt cttcagccac atactttcct tccactggcc agcattctcc     360
tctattagac tagaactgtg gataaacctc agaaaatggc cacccagcag aaagcctctg     420
acgagaggat ctcccagttt gatcacaatt tgctgccaga gctgtctgct cttctgggcc     480
tagatgcagt tcagttggca aaggaactag aagaagagga gcagaaggag cgagcaaaaa     540
tgcagaaagg ctacaactct caaatgcgca gtgaagcaaa aaggttaaag acttttgtga     600
cttatgagcc gtacagctca tggataccac aggagatggc ggccgctggg tttacttca      660 ctggggtaaa atctgggatt cagtgcttct gctgtagcct aatcctcttt ggtgccggcc     720
tcacgagact ccccatagaa gaccacaaga ggtttcatcc agattgtggg ttcctttga      780 acaaggatgt tggtaacatt gccaagtacg acataagggt gaagaatctg aagagcaggc     840
tgagaggagg taaaatgagg taccaagaag aggaggctag acttgcgtcc ttcaggaact     900 ggccattta tgtccaaggg atatcccctt gtgtgctctc agaggctggc tttgtctta      960 caggtaaaca ggacacggta cagtgttttt cctgtggtgg atgtttagga aattgggaag    1020
aaggagatga tccttggaag gaacatgcca atggttccc caaatgtgaa tttcttcgga    1080
gtaagaaatc ctcagaggaa attacccagt atattcaaag ctacaaggga tttgttgaca    1140
taacgggaga acattttgtg aattcctggg tccagagaga attacctatg gcatcagctt    1200
attgcaatga cagcatcttt gcttacgaag aactacggct ggactctttt aaggactggc    1260
cccgggaatc agctgtggga gttgcagcac tggccaaagc aggtcttttc tacacaggta    1320
taaaggacat cgtccagtgc ttttcctgtg gagggtgttt agagaaatgg cagggaaggtg    1380 atgacccatt agacgatcac accagatgtt tcccaattg tccatttctc caaaatatga    1440
agtcctctgc ggaagtgact ccagaccttc agagccgtgg tgaactttgt gaattactgg    1500
aaaccacaag tgaaagcaat cttgaagatt caatagcagt tggtcctata gtgccagaaa    1560
tggcacaggg tgaagcccag tggtttcaag aggcaaagaa tctgaatgag cagctgagag    1620
```

-continued

```
cagcttatac cagcgccagt ttccgccaca tgtctttgct tgatatctct tccgatctgg    1680
ccacggacca cttgctgggc tgtgatctgt ctattgcttc aaaacacatc agcaaacctg    1740
tgcaagaacc tctggtgctg cctgaggtct tggcaactt gaactctgtc atgtgtgtgg     1800
agggtgaagc tggaagtgga aagacggtcc tcctgaagaa aatagctttt ctgtgggcat    1860
ctggatgctg tccctgtta aacaggttcc agctggtttt ctacctctcc cttagttcca    1920
ccagaccaga cgagggctg ccagtatca tctgtgacca gctcctagag aaagaaggat      1980
ctgttactga aatgtgcatg aggaacatta ccagcagtt aaagaatcag gtcttattcc     2040
ttttagatga ctacaaagaa atatgttcaa tccctcaagt cataggaaaa ctgattcaaa    2100
aaaaccactt atcccggacc tgcctattga ttgctgtccg tacaaacagg gccagggaca    2160
tccgccgata cctagagacc attctagaga tccaagcatt tcccttttat aatactgtct    2220
gtatattacg gaagctcttt tcacataata tgactcgtct gcgaaagttt atggtttact    2280
ttggaaagaa ccaagtttg cagaagatac agaaaactcc tctctttgtg gcggcgatct     2340
gtgctcattg gtttcagtat cctttgacc catcctttga tgatgtggct gttttcaagt     2400
cctatatgga acgcctttcc ttaaggaaca aagcgcacagc tgaaattctc aaagcaactg   2460
tgtcctcctg tggtgagctg gccttgaaag gttttttttc atgttgcttt gagtttaatg    2520
atgatgatct cgcagaagca ggggttgatg aagatgaaga tctaaccatg tgcttgatga    2580
gcaaatttac agcccagaga ctaagaccat tctaccggtt tttaagtcct gccttccaag    2640
aatttcttgc gggatgagg ctgattgaac tcctggattc agataggcag gaacatcaag      2700
atttgggact gtatcatttg aaacaaatca actcacccat gatgactgta agcgcctaca    2760
acaatttttt gaactatgtc tccagcctcc cttcaacaaa agcagggccc aaaattgtgt    2820
ctcatttgct ccatttagtg gataacaaag agtcattgga gaatatatct gaaaatgatg    2880
actacttaaa gcaccagcca gaaatttcac tgcagatgca gttacttagg ggattgtggc    2940
aaatttgtcc acaagcttac ttttcaatgg tttcagaaca tttactggtt cttgccctga    3000
aaactgctta tcaaagcaac actgttgctg cgtgttctcc atttgttttg caattccttc    3060
aagggagaac actgactttg ggtgcgctta acttacagta ctttttcgac cacccagaaa    3120
gcttgtcatt gttgaggagc atccacttcc aatacgagg aaataagaca tcacccagag     3180 cacattttc agttctggaa acatgttttg acaaatcaca ggtgccaact atagatcagg      3240
actatgcttc tgcctttgaa cctatgaatg aatgggagcg aaatttagct gaaaagagg     3300 ataatgtaaa gagctatatg gatatgcagc gcagggcatc accagacctt agtactggct    3360
attggaaact ttctccaaag cagtacaaga ttccctgtct agaagtcgat gtgaatgata    3420
ttgatgttgt aggccaggat atgcttgaga ttctaatgac agtttctca gcttcacagc     3480 gcatcgaact ccatttaaac cacagcagag gctttataga aagcatccgc ccagctcttg    3540
agctgtctaa ggcctctgtc accaagtgct ccataagcaa gttggaactc agcgcagccg    3600
aacaggaact gcttctcacc ctgccttccc tggaatctct tgaagtctca gggacaatcc    3660
agtcacaaga ccaaatcttt cctaatctgg ataagttcct gtgcctgaaa gaactgtctg    3720
tggatctgga gggcaatata aatgttttt cagtcattcc tgaagaattt ccaaacttcc     3780
accatatgga gaaattattg atccaaattt cagctgagta tgatccttcc aaactagtaa    3840
aattaattca aaattctcca aaccttcatg ttttccatct gaagtgtaac ttcttttcgg    3900
atttagggtc tctcatgact atgcttgttt cctgtaagaa actcacagaa attaagttttt   3960 cggattcatt ttttcaagcc gtcccatttg ttgccagttt gccaaatttt atttctctga    4020
```

```
agatattaaa tcttgaaggc cagcaatttc ctgatgagga acatcagaaa aaatttgcct    4080
acatttagg ttctcttagt aacctggaag aattgatcct tcctactggg gatggaattt    4140
atcgagtggc caaactgatc atccagcagt gtcagcagct tcattgtctc cgagtcctct    4200
cattttcaa gactttgaat gatgacagcg tggtggaaat tgccaaagta gcaatcagtg    4260
gaggtttcca gaaacttgag aacctaaagc tttcaatcaa tcacaagatt acagaggaag    4320
gatacagaaa tttctttcaa gcactggaca acatgccaaa cttgcaggag ttggacatct    4380
ccaggcattt cacagagtgt atcaaagctc aggccacaac agtcaagtct ttgagtcaat    4440
gtgtgttacg actaccaagg ctcattagac tgaacatgtt aagttggctc ttggatgcag    4500
atgatattgc attgcttaat gtcatgaaag aaagacatcc tcaatctaag tacttaacta    4560
ttctccagaa atggatactg ccgttctctc caatcattca gaaataaaag attcagctaa    4620
aaactgctga atcaataatt tgtcttgggg catattgagg atgtaaaaaa agttgttgat    4680
taatgctaaa aaccaaatta tccaaaatta ttttattaaa tattgcatac aaagaaaat     4740
gtgtaaggct tgctaaaaaa caaaacaaaa caaaacacag tcctgcatac tcaccaccaa    4800
gctcaagaaa taaatcatca ccaataccttt gaggtccct gagtaatcca ccccagctaa    4860
aggcaaaccc ttcaatcaag tttatacagc aaaccctcca ttgtccatgg tcaacaggga    4920
aggggttggg gacaggtctg ccaatctatc taaaagccac aatatggaag aagtattcaa    4980
tttatataat aaatggctaa cttaacggtt gaatcacttt catacatgga tgaaacgggt    5040
ttaacacagg atccacatga atcttctgtg ggccaagaga tgttccttaa tccttgtaga    5100
acctgttttc tatattgaac tagctttggt acagtagagt taacttactt tccatttatc    5160
cactgccaat ataagagga aacagggggtt agggaaaaat gacttcattc cagaggcttc    5220
tcagagttca acatatgcta taatttagaa ttttcttatg aatccactct acttgggtag    5280
aaaatatttt atctctagtg attgcatatt atttccatat catagtattt catagtatta    5340
tatttgatat gagtgtctat atcaatgtca gtgtccagaa tttcgttcct accagttaag    5400
tagttttctg aacggccaga agaccattcg aaattcatga tactactata agttggtaaa    5460
caaccatact tttatcctca ttttttattct cactaagaaa aaagtcaact cccctcccct   5520
tgcccaagta tgaaatatag ggacagtatg tatggtgtgg tctcatttgt ttagaaaacc    5580
acttatgact gggtgcggtg gctcacacct gtaatcccag cactttggga ggctgaggcg    5640
ggcgaatcat ttgaggtgag gaattcgaga ccagcctggc cagcatggtg aaaccccatc    5700
tctactaaaa atacaaaaat tagccaggtg tggtggcaca tgcctgtagt cccagccact    5760
agggcggctg agacgcaaga cttgcttgaa cccgggaggc agaggttgca gtgagccaag    5820
atggcgccac tgcattccag cctgggcaac agagcaagac cctgtctgtc tcaaaacaaa    5880
aaacaaaacc acttatattg ctagctacat taagaatttc tgaatatgtt actgagcttg    5940
cttgtggtaa ccatttataa tatcagaaag tatatgtaca ccaaaacatg ttgaacatcc    6000
atgttgtaca actgaaatat aaataatttt gtcaattata cctaaataaa actggaaaaa    6060
aatttctgga agtttatatc taaaaatgtt aatagtgcgt acctctagga agtgggcctg    6120
gaagccattc ttactttca gtctctccca ttctgtactg tttttttgttt tactttcgtg    6180
cctgcattat ttttctattt aaaacaaaaa taaatctagt ttagcact                6228
```

<210> SEQ ID NO 24
<211> LENGTH: 1403
<212> TYPE: PRT
<213> ORGANISM: Homo sapiens

<400> SEQUENCE: 24

```
Met Ala Thr Gln Gln Lys Ala Ser Asp Glu Arg Ile Ser Gln Phe Asp
1               5                   10                  15

His Asn Leu Leu Pro Glu Leu Ser Ala Leu Leu Gly Leu Asp Ala Val
            20                  25                  30

Gln Leu Ala Lys Glu Leu Glu Glu Glu Gln Lys Glu Arg Ala Lys
        35                  40                  45

Met Gln Lys Gly Tyr Asn Ser Gln Met Arg Ser Glu Ala Lys Arg Leu
    50                  55                  60

Lys Thr Phe Val Thr Tyr Glu Pro Tyr Ser Ser Trp Ile Pro Gln Glu
65                  70                  75                  80

Met Ala Ala Gly Phe Tyr Phe Thr Gly Val Lys Ser Gly Ile Gln
                85                  90                  95

Cys Phe Cys Cys Ser Leu Ile Leu Phe Gly Ala Gly Leu Thr Arg Leu
                100                 105                 110

Pro Ile Glu Asp His Lys Arg Phe His Pro Asp Cys Gly Phe Leu Leu
            115                 120                 125

Asn Lys Asp Val Gly Asn Ile Ala Lys Tyr Asp Ile Arg Val Lys Asn
130                 135                 140

Leu Lys Ser Arg Leu Arg Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
            195                 200                 205

Glu Gly Asp Asp Pro Trp Lys Glu His Ala Lys Trp Phe Pro Lys Cys
210                 215                 220

Glu Phe Leu Arg Ser Lys Lys Ser Ser Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
        275                 280                 285

Pro Arg Glu Ser Ala Val Gly Val Ala Ala Leu Ala Lys Ala Gly Leu
    290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335

Arg Cys Phe Pro Asn Cys Pro Phe Leu Gln Asn Met Lys Ser Ser Ala
            340                 345                 350

Glu Val Thr Pro Asp Leu Gln Ser Arg Gly Glu Leu Cys Glu Leu Leu
        355                 360                 365

Glu Thr Thr Ser Glu Ser Asn Leu Glu Asp Ser Ile Ala Val Gly Pro
    370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415
```

-continued

```
Arg His Met Ser Leu Leu Asp Ile Ser Ser Asp Leu Ala Thr Asp His
            420                 425                 430
Leu Leu Gly Cys Asp Leu Ser Ile Ala Ser Lys His Ile Ser Lys Pro
            435                 440                 445
Val Gln Glu Pro Leu Val Leu Pro Glu Val Phe Gly Asn Leu Asn Ser
            450                 455                 460
Val Met Cys Val Glu Gly Glu Ala Gly Ser Gly Lys Thr Val Leu Leu
465                 470                 475                 480
Lys Lys Ile Ala Phe Leu Trp Ala Ser Gly Cys Cys Pro Leu Leu Asn
            485                 490                 495
Arg Phe Gln Leu Val Phe Tyr Leu Ser Leu Ser Ser Thr Arg Pro Asp
            500                 505                 510
Glu Gly Leu Ala Ser Ile Ile Cys Asp Gln Leu Leu Glu Lys Glu Gly
            515                 520                 525
Ser Val Thr Glu Met Cys Met Arg Asn Ile Ile Gln Gln Leu Lys Asn
            530                 535                 540
Gln Val Leu Phe Leu Leu Asp Asp Tyr Lys Glu Ile Cys Ser Ile Pro
545                 550                 555                 560
Gln Val Ile Gly Lys Leu Ile Gln Lys Asn His Leu Ser Arg Thr Cys
            565                 570                 575
Leu Leu Ile Ala Val Arg Thr Asn Arg Ala Arg Asp Ile Arg Arg Tyr
            580                 585                 590
Leu Glu Thr Ile Leu Glu Ile Lys Ala Phe Pro Phe Tyr Asn Thr Val
            595                 600                 605
Cys Ile Leu Arg Lys Leu Phe Ser His Asn Met Thr Arg Leu Arg Lys
            610                 615                 620
Phe Met Val Tyr Phe Gly Lys Asn Gln Ser Leu Gln Lys Ile Gln Lys
625                 630                 635                 640
Thr Pro Leu Phe Val Ala Ala Ile Cys Ala His Trp Phe Gln Tyr Pro
            645                 650                 655
Phe Asp Pro Ser Phe Asp Asp Val Ala Val Phe Lys Ser Tyr Met Glu
            660                 665                 670
Arg Leu Ser Leu Arg Asn Lys Ala Thr Ala Glu Ile Leu Lys Ala Thr
            675                 680                 685
Val Ser Ser Cys Gly Glu Leu Ala Leu Lys Gly Phe Ser Cys Cys
            690                 695                 700
Phe Glu Phe Asn Asp Asp Asp Leu Ala Glu Ala Gly Val Asp Glu Asp
705                 710                 715                 720
Glu Asp Leu Thr Met Cys Leu Met Ser Lys Phe Thr Ala Gln Arg Leu
            725                 730                 735
Arg Pro Phe Tyr Arg Phe Leu Ser Pro Ala Phe Gln Glu Phe Leu Ala
            740                 745                 750
Gly Met Arg Leu Ile Glu Leu Leu Asp Ser Asp Arg Gln Glu His Gln
            755                 760                 765
Asp Leu Gly Leu Tyr His Leu Lys Gln Ile Asn Ser Pro Met Met Thr
            770                 775                 780
Val Ser Ala Tyr Asn Asn Phe Leu Asn Tyr Val Ser Ser Leu Pro Ser
785                 790                 795                 800
Thr Lys Ala Gly Pro Lys Ile Val Ser His Leu Leu His Leu Val Asp
            805                 810                 815
Asn Lys Glu Ser Leu Glu Asn Ile Ser Glu Asn Asp Asp Tyr Leu Lys
            820                 825                 830
```

```
His Gln Pro Glu Ile Ser Leu Gln Met Gln Leu Leu Arg Gly Leu Trp
        835                 840                 845

Gln Ile Cys Pro Gln Ala Tyr Phe Ser Met Val Ser Glu His Leu Leu
850                 855                 860

Val Leu Ala Leu Lys Thr Ala Tyr Gln Ser Asn Thr Val Ala Ala Cys
865                 870                 875                 880

Ser Pro Phe Val Leu Gln Phe Leu Gln Gly Arg Thr Leu Thr Leu Gly
                885                 890                 895

Ala Leu Asn Leu Gln Tyr Phe Phe Asp His Pro Glu Ser Leu Ser Leu
            900                 905                 910

Leu Arg Ser Ile His Phe Pro Ile Arg Gly Asn Lys Thr Ser Pro Arg
        915                 920                 925

Ala His Phe Ser Val Leu Glu Thr Cys Phe Asp Lys Ser Gln Val Pro
    930                 935                 940

Thr Ile Asp Gln Asp Tyr Ala Ser Ala Phe Glu Pro Met Asn Glu Trp
945                 950                 955                 960

Glu Arg Asn Leu Ala Glu Lys Glu Asp Asn Val Lys Ser Tyr Met Asp
                965                 970                 975

Met Gln Arg Arg Ala Ser Pro Asp Leu Ser Thr Gly Tyr Trp Lys Leu
            980                 985                 990

Ser Pro Lys Gln Tyr Lys Ile Pro Cys Leu Glu Val Asp Val Asn Asp
        995                 1000                1005

Ile Asp Val Val Gly Gln Asp Met Leu Glu Ile Leu Met Thr Val Phe
    1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
                1045                1050                1055

Lys Cys Ser Ile Ser Lys Leu Glu Leu Ser Ala Ala Glu Gln Glu Leu
            1060                1065                1070

Leu Leu Thr Leu Pro Ser Leu Glu Ser Leu Glu Val Ser Gly Thr Ile
        1075                1080                1085

Gln Ser Gln Asp Gln Ile Phe Pro Asn Leu Asp Lys Phe Leu Cys Leu
    1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
                1125                1130                1135

Gln Ile Ser Ala Glu Tyr Asp Pro Ser Lys Leu Val Lys Leu Ile Gln
            1140                1145                1150

Asn Ser Pro Asn Leu His Val Phe His Leu Lys Cys Asn Phe Phe Ser
        1155                1160                1165

Asp Phe Gly Ser Leu Met Thr Met Leu Val Ser Cys Lys Lys Leu Thr
    1170                1175                1180

Glu Ile Lys Phe Ser Asp Ser Phe Phe Gln Ala Val Pro Phe Val Ala
1185                1190                1195                1200

Ser Leu Pro Asn Phe Ile Ser Leu Lys Ile Leu Asn Leu Glu Gly Gln
                1205                1210                1215

Gln Phe Pro Asp Glu Glu Thr Ser Glu Lys Phe Ala Tyr Ile Leu Gly
            1220                1225                1230

Ser Leu Ser Asn Leu Glu Glu Leu Ile Leu Pro Thr Gly Asp Gly Ile
        1235                1240                1245
```

```
Tyr Arg Val Ala Lys Leu Ile Ile Gln Gln Cys Gln Gln Leu His Cys
    1250                1255                1260

Leu Arg Val Leu Ser Phe Phe Lys Thr Leu Asn Asp Asp Ser Val Val
1265                1270                1275                1280

Glu Ile Ala Lys Val Ala Ile Ser Gly Gly Phe Gln Lys Leu Glu Asn
                1285                1290                1295

Leu Lys Leu Ser Ile Asn His Lys Ile Thr Glu Glu Gly Tyr Arg Asn
                1300                1305                1310

Phe Phe Gln Ala Leu Asp Asn Met Pro Asn Leu Gln Glu Leu Asp Ile
            1315                1320                1325

Ser Arg His Phe Thr Glu Cys Ile Lys Ala Gln Ala Thr Thr Val Lys
    1330                1335                1340

Ser Leu Ser Gln Cys Val Leu Arg Leu Pro Arg Leu Ile Arg Leu Asn
1345                1350                1355                1360

Met Leu Ser Trp Leu Leu Asp Ala Asp Asp Ile Ala Leu Leu Asn Val
                1365                1370                1375

Met Lys Glu Arg His Pro Gln Ser Lys Tyr Leu Thr Ile Leu Gln Lys
                1380                1385                1390

Trp Ile Leu Pro Phe Ser Pro Ile Ile Gln Lys
            1395                1400

<210> SEQ ID NO 25
<211> LENGTH: 24
<212> TYPE: DNA
<213> ORGANISM: Artificial Sequence
<220> FEATURE:
<223> OTHER INFORMATION: Synthetic primer based on Homo sapiens

<400> SEQUENCE: 25
gtgaactgca ctgtgacaag ctgc                                              24

<210> SEQ ID NO 26
<211> LENGTH: 22
<212> TYPE: DNA
<213> ORGANISM: Artificial Sequence
<220> FEATURE:
<223> OTHER INFORMATION: Synthetic primer based on Homo sapiens

<400> SEQUENCE: 26
atataaacaa cgaattatct cc                                                22

<210> SEQ ID NO 27
<211> LENGTH: 24
<212> TYPE: DNA
<213> ORGANISM: Artificial Sequence
<220> FEATURE:
<223> OTHER INFORMATION: Synthetic primer based on Homo sapiens

<400> SEQUENCE: 27
gtattataat caataagtta tacc                                              24
```